United States Patent
Rao et al.

(10) Patent No.: US 10,220,053 B2
(45) Date of Patent: Mar. 5, 2019

(54) METHODS AND COMPOSITIONS FOR MODULATING CANCER STEM CELLS

(71) Applicant: University of Canberra, Bruce (AU)

(72) Inventors: Sudha Rao, McKellar (AU); Anjum Zafar, Bruce (AU)

(73) Assignee: University of Canberra, Bruce, Australian, Capital Territory (AU)

( * ) Notice: Subject to any disclaimer, the term of this patent is extended or adjusted under 35 U.S.C. 154(b) by 0 days.

(21) Appl. No.: 14/899,549

(22) PCT Filed: Jun. 17, 2014

(86) PCT No.: PCT/AU2014/050073
§ 371 (c)(1),
(2) Date: Dec. 17, 2015

(87) PCT Pub. No.: WO2014/205511
PCT Pub. Date: Dec. 31, 2014

(65) Prior Publication Data
US 2016/0143938 A1    May 26, 2016

(30) Foreign Application Priority Data

Jun. 25, 2013 (AU) ................................ 2013902309
Mar. 19, 2014 (AU) ................................ 2014900953

(51) Int. Cl.
| | | |
|---|---|---|
| C12Q 1/68 | (2018.01) |
| G01N 33/50 | (2006.01) |
| G01N 33/68 | (2006.01) |
| C12N 15/113 | (2010.01) |
| A61K 31/713 | (2006.01) |
| A61K 45/06 | (2006.01) |
| A61K 31/131 | (2006.01) |
| A61K 31/135 | (2006.01) |
| A61K 31/15 | (2006.01) |
| C12Q 1/26 | (2006.01) |
| G01N 33/574 | (2006.01) |

(52) U.S. Cl.
CPC .......... *A61K 31/713* (2013.01); *A61K 31/131* (2013.01); *A61K 31/135* (2013.01); *A61K 31/15* (2013.01); *A61K 45/06* (2013.01); *C12N 15/1137* (2013.01); *C12Q 1/26* (2013.01); *G01N 33/5011* (2013.01); *G01N 33/57484* (2013.01); *G01N 2500/02* (2013.01)

(58) Field of Classification Search
None
See application file for complete search history.

(56) References Cited

U.S. PATENT DOCUMENTS

2012/0142784 A1    6/2012 Schule et al.

FOREIGN PATENT DOCUMENTS

| WO | WO 2012/009475 | * | 1/2012 |
| WO | 2014194280 A2 | | 12/2014 |

OTHER PUBLICATIONS

Tsunoda et al (Oncology 81:336-344, 2011).*
Ugolkov et al (The Prostate 71:18-25 (2011)).*
Maier et al (FEBS Lett 583:3966-3973, 2009).*
Ghuwalewala Stem Cell Res. 16:405-417, 2016).*
Sterlacci et al ((J Thorac Oncol. 2014;9: 41-49).*
Chen et al (Biomaterials 33 (2012) 1437e1444).*
Leis et al (Oncogene (2012) 31, 1354-1365).*
Azzam et al (EMBO Mol. Med. 5:1502-1522, 2013) (Year: 2013).*
Han H., et al. "Synergistic re-activation of epigenetically silenced genes by combinatorial inhibition of DNMTs and LSD1 in cancer cells", PLoS One, published Sep. 6, 2013, vol. 8, Issue 9, e75136, pp. 1-10.
Huang Y., et al. "Inhibitors of histone demethylation and histone deacetylation cooperate in regulating gene expression and inhibiting growth in human breast cancer cells", Breast Cancer Research and Treatment, 2012, vol. 131, pp. 777-789.
International Search Report for International Application No. PCT/AU2014/050073, Applicant University of Canberra, dated Sep. 1, 2014; pp. 3.
Wang J., et al, "Novel histone demethylase LSD1 inhibitors selectively target cancer cells with pluripotent stem cell properties", Cancer Research, 2011, vol. 71, pp. 7238-7249.
Zheng Y-C., et al, "Triazole-dithiocarbamate based, selective LSD1 inactivators inhibit gastric cancer cell growth, invasion and migration", Journal of Medicinal Chemistry, Nov. 14, 2013, vol. 56, pp. 8543-8560.
Wojcieszynska, D. et al., Int J. Mol. Sci., 13: 16751-16768 (2012).
Hwang, S., Efforts to Elucidate the Binding Interaction between Lysine-Specific Demethylase 1, 1-278 (2012).
Willmann, D., Int. J. of Cancer, 131: 2704-2709 (2012).
Lim, S. et al., Carcinogenesis, 31: 512-520 (2010).
Al-Hajj, M. et al., Proceedings of the National Academy of Sciences, 100: 3983-3988 (2003).
Ikushima, H. et al., Journal of Biochemistry, 286: 41434-41441 (2011).
Yu et al., Science, 318: 1917-1920 (2007).
Ling et al., Oncology Letters, 4: 1264-1268 (2012).
Wang et al., Int. Urol. Nephrol., 47: 485-490 (2015).
Wang et al., Biochemical and Biophysical Research Communications, 467: 310-315 (2015).
Scheel et al., Seminars in Cancer Biology, 22: 396-403 (2012).
Hino et al., Cancer Sci., 107(9): 1187-1192 (2016).
Kosumi et al., Int. J. Cancer, 138: 428-439 (2016).
Stavropoulos et al., Expert Opin. Ther. Targets, 11(6): 809-820 (2007).

(Continued)

*Primary Examiner* — Richard A Schnizer
(74) *Attorney, Agent, or Firm* — Edell, Shapiro & Finnan, LLC

(57) ABSTRACT

Disclosed are compositions and methods that use lysine demethylase inhibitors for inhibiting the growth of cancer stem cells or tumor initiating cells, for enhancing the biological effects of chemotherapeutic drugs or irradiation on cancer cells and/or for preventing cancer recurrence.

17 Claims, 9 Drawing Sheets

(56) References Cited

OTHER PUBLICATIONS

Hayami et al., Int. J. Cancer, 128: 574-586 (2010).
Zheng et al., Medicinal Research Reviews, 35(5): 1032-1071 (2015).
Ambrosio et al., BBA—Gene Regulatory Mechanisms, 1860: 905-910 (2017).
Abubaker et al., Molecular Cancer, 12:24 (2013).
Tang et al., Chin. J. Cancer, 30(6): 426-432 (2011).
Hamilton et al., J. Bioanal. Biomed., S9:003 (2013).
Lin et al., Clin. Cancer Res., 18(17): 4691-4701 (2012).
Alsaqer et al., Oncotarget, 8(43): 73372-73386 (2017).
Huang et al., Cancer Letters, 398:12-21 (2017).
Lan et al., Medical Hypotheses, 81: 823-825 (2013).
Stewart et al., Cancer Cell, 28:4-6 (2015).

\* cited by examiner

NS – Control cells
ST – Cancer Cell population

A

B

C

METHODS AND COMPOSITIONS FOR MODULATING CANCER STEM CELLS

RELATED APPLICATIONS

This application claims priority to Australian Provisional Application No. 2013902309 entitled "Stem cell modulation", filed on 25 Jun. 2013, and to Australian Provisional Application No. 2014900953 entitled "Stem cell modulation I", filed on 19 Mar. 2014, the subject matter of each of which is hereby incorporated herein by reference in its entirety.

FIELD OF THE INVENTION

This invention relates generally to lysine demethylase inhibitors in methods and composition for inhibiting the growth of cancer stem cells or tumor initiating cells, for enhancing the biological effects of chemotherapeutic drugs or irradiation on cancer cells and/or for preventing cancer recurrence.

BACKGROUND OF THE INVENTION

Cancer stem cells (CSCs), or 'precursor' metastatic cells, initiate tumors and drive malignant progression by generating and supporting replication of more differentiated non-stem cell progeny (see, for example, Kleffel et al., 2013. *Adv Exp Med Biol.* 734:145-79; Chen et al., 2013. *Acta Pharmacologica Sinica* 34:732-740; Páez et al., 2012, *Clin Cancer Res.* 18(3):645-53). CSCs have been demonstrated to be fundamentally responsible for tumorigenesis, cancer metastasis, tumor relapse, drug resistance, and chemo- and radio-therapy failure. Unfortunately, the mechanisms by which CSCs cause tumor formation and growth and the potential role of CSC-specific differentiation plasticity in tumorigenicity are currently unknown.

Of interest, CSCs share many similar traits with normal stem cells. For example, CSCs have self-renewal capacity, namely, the ability to give rise to additional tumorigenic cancer stem cells, typically at a slower rate than other dividing tumor cells, as opposed to a limited number of divisions. CSCs also have the ability to differentiate into multiple cell types (i.e., they are multipotent), which would explain histological evidence that not only many tumors contain multiple cell types native to the host organ, but also that heterogeneity is commonly retained in tumor metastases.

CSCs express certain cell surface markers as listed for example in Table 1

Normal somatic stem cells are naturally resistant to chemotherapeutic agents—they have various pumps (such as multi-drug resistance (MDR) proteins) that pump out drugs, and efficient DNA repair mechanisms. Further, they also have a slow rate of cell turnover while chemotherapeutic agents target rapidly replicating cells. CSCs, being the mutated counterparts of normal stem cells, may also have similar mechanisms that allow them to survive drug therapies and radiation treatment. In other words, conventional chemotherapies and radiotherapies kill differentiated or differentiating cells, which form the bulk of the tumor that are unable to regenerate tumors. The population of CSCs that gave rise to the differentiated and differentiating cells, on the other hand, could remain untouched and cause a relapse of the disease. A further danger for the conventional anti-cancer therapy is the possibility that the treatment of, for instance, chemotherapy, leaves only chemotherapy-resistant CSCs, and the ensuing recurrent tumor will likely also be resistant to chemotherapy.

Consequently, there is a pressing need for the identification of novel approaches that target cytotoxic drug-resistant, tumor-initiating CSCs for preventing and/or treating disease recurrence and distant metastatic spread.

SUMMARY OF THE INVENTION

The present invention is based in part on the determination that histone demethylases, including lysine specific demethylases (LSDs) (e.g., LSD1 and LSD2), are overexpressed in breast CSCs and that inhibition of these enzymes results in specific cell death of the breast CSCs. Based on the determination that LSDs are overexpressed in prostate, lung and bladder CSCs, the present inventors propose that other CSCs can also be treated with LSD inhibitors to reduce or inhibit their proliferation and/or to stimulate their death.

Accordingly, in one aspect, the present invention provides methods for inhibiting the proliferation, survival or viability of a CSC. These methods generally comprise, consist or consist essentially of contacting the CSC with a proliferation-, survival- or viability-inhibiting amount of a LSD inhibitor. In some embodiments, the CSC is selected from breast, prostate, lung, bladder, pancreatic, colon, melanoma, liver or glioma CSCs.

In specific embodiments, the CSC is a breast cancer CSC. Suitably, the CSC has impaired or abrogated expression of the pluripotent stem cell markers Oct4 or Sox2 or expresses one or both of those markers at a level or functional activity that is less than about $1/5$, $1/10$, $1/20$, $1/50$, $10^{-1}$, $10^{-2}$, $10^{-3}$, $10^{-4}$,

TABLE 1

CSC markers for distinct solid tumor types

| Breast | Colon | Glioma | Liver | Lung | Melanoma | Ovarian | Pancreatic | Prostate |
|---|---|---|---|---|---|---|---|---|
| ALDH1 | ABCB5 ALDH1 | | | | | | ABCG2 | |
| CD24 | β-catenin activity | CD15 | CD13 | ALDH1 | ABCB5 | | ALDH1 | ALDH1 |
| CD44 | CD24 | CD90 | CD24 | ABCG2 | ALDH1 | CD24 | CD24 | CD44 |
| CD90 | CD26 | CD133 | CD44 | CD90 | CD20 | CD44 | CD44 | CD133 |
| CD133 | CD29 | $\alpha_6$ integrin | CD90 | CD117 | CD133 | CD117 | CD133 | $\alpha_2 \beta_1$ integrin |
| Hedgehog-Gli activity | CD44 | Nestin | CD133 | CD133 | CD271 | CD133 | c-Met | $\alpha_6$ integrin |
| $\alpha_6$ integrin | CD133 CD166 LGR5 | | | | | | CXCR4 Nestin Nodal-Activin | Trop2 |

$10^{-5}$, $10^{-6}$, $10^{-7}$, $10^{-8}$, $10^{-9}$, $10^{-10}$, $10^{-11}$, $10^{-12}$, $10^{-13}$, $10^{-14}$ or about $10^{-15}$ of the level or functional activity of those markers on a pluripotent stem cell.

Suitably, the CSC expresses one or more (e.g., 1, 2, 3, 4, 5, 6, 7, 8 or more) CSC markers selected from ABCB5, ALDH1, ABCG2, $\alpha_6$ integrin, $\sigma_2$ $\beta_1$ integrin, β-catenin activity, CD15, CD13, CD20, CD24, CD26, CD29, CD44, CD90, CD133, CD166, CD271, c-Met, Hedgehog-Gli, Nestin, CXCR4, LGR5, Trop2 and Nodal-Activin. In some embodiments, the CSC expresses one or more (e.g., 1, 2, 3, 4, 5, 6, 7, 8 or more) CSC markers selected from ALDH1, CD24, CD44, CD90, CD133, Hedgehog-Gli, $\alpha_6$ integrin. In illustrative examples of this type, the CSC expresses CD24 and CD44 (e.g., $CD44^{high}$, $CD24^{low}$.

Non-limiting examples of suitable LSD inhibitors include nucleic acids, peptides, polypeptides, peptidomimetics, carbohydrates, lipids or other organic (carbon containing) or inorganic molecules. In specific embodiments, the LSD inhibitor is selected from small molecule inhibitors and nucleic acid molecules (e.g., ones that inhibit the transcription or translation of a LSD gene (e.g., LSD1 or LSD2) or that mediate RNA interference). In some embodiments, the LSD inhibitor reduces the expression of the LSD gene or the level or functional activity (e.g., reduces the level of a LSD polypeptide or reduces LSD-mediated demethylation) of a LSD inhibitor expression product to less than about $9/10$, $4/5$, $7/10$, $3/5$, $1/2$, $2/5$, $3/10$, $1/5$, $1/10$, $1/20$, $1/50$, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$ or about $10^{-15}$ of the expression of the LSD gene, or the level or functional activity of a corresponding LSD expression product in the absence of the inhibitor. In some embodiments, the LSD inhibitor is a selective LSD inhibitor (e.g., a selective LSD1 inhibitor or a selective LSD2 inhibitor). In other embodiments, the LSD inhibitor is a Pan-LSD inhibitor. In still other embodiments, the LSD inhibitor is a non-selective LSD inhibitor.

In some embodiments, the methods for inhibiting the proliferation, survival or viability of the CSC further comprise detecting overexpression of a LSD gene (e.g., LSD1 or LSD2) in the CSC prior to contacting the CSC with the LSD inhibitor.

Suitably, the methods for inhibiting the proliferation, survival or viability of the CSC further comprise detecting that the CSC expresses one or more CSC markers as broadly described above.

In another aspect, the present invention provides methods for treating or preventing a cancer (e.g., a metastatic cancer) in a subject, wherein the cancer comprises CSCs and non-CSC tumor cells. These methods generally comprise, consist or consist essentially of administering to the subject a LSD inhibitor in an effective amount to inhibit the proliferation, survival or viability of the CSCs. In advantageous embodiments, the methods further comprise identifying that the subject has or is at risk of developing a cancer comprising CSCs and non-CSC tumor cells prior to the administration of the LSD inhibitor. In some embodiments, the cancer is selected from breast, prostate, lung, bladder, pancreatic, colon, melanoma, liver or glioma cancer. Suitably, the CSCs give rise to non-CSC tumor cells that are hormone-resistant. In illustrative examples of this type, the non-CSC tumor cells have reduced or abrogated expression of one or more (e.g., 1 or 2) hormone receptors selected from an estrogen receptor (ER) and a progesterone receptor (PR). Suitably, the cancer is selected from breast, prostate, lung, bladder, pancreatic, colon, melanoma, liver or brain cancer. In specific embodiments, the cancer is breast cancer.

In some embodiments, the methods for treating or preventing a cancer further comprise detecting overexpression of a LSD gene (e.g., LSD1 or LSD2) in a tumor sample obtained from the subject, wherein the tumor sample comprises the CSCs, prior to administering the LSD inhibitor to the subject.

In some embodiments, the methods for treating or preventing a cancer further comprise detecting expression of one or more CSC markers as broadly described above in a tumor sample obtained from the subject, wherein the tumor sample comprises the CSCs, prior to administering the LSD inhibitor to the subject.

Yet another aspect of the present invention provides methods for treating or preventing a cancer (e.g., a metastatic cancer) in a subject, wherein the cancer comprises CSCs and non-CSC tumor cells. These methods generally comprise, consist or consist essentially of concurrently administering to the subject a LSD inhibitor in an effective amount to inhibit the proliferation, survival or viability of the CSCs and a cancer therapy or agent that inhibits the proliferation, survival or viability of the non-CSC tumor cells, to thereby treat or prevent the cancer. In some embodiments, the cancer therapy or agent is selected from radiotherapy, surgery, chemotherapy, hormone ablation therapy, pro-apoptosis therapy and immunotherapy. In illustrative examples of this type, the cancer therapy or agent targets rapidly dividing cells or disrupts the cell cycle or cell division. Suitably, the methods further comprise identifying that the subject has or is at risk of developing a cancer comprising CSCs and non-CSC tumor cells prior to the co-administration. In some embodiments, the cancer is selected from breast, prostate, lung, bladder, pancreatic, colon, melanoma, liver or glioma cancer. Suitably, the non-CSC tumor cells are hormone-resistant. In illustrative examples of this type, the non-CSC tumor cells have reduced or abrogated expression of one or more (e.g., 1 or 2) hormone receptors selected from an estrogen receptor (ER) and a progesterone receptor (PR). Suitably, the cancer is selected from breast, prostate, lung, bladder, pancreatic, colon, melanoma, liver or brain cancer. In specific embodiments, the cancer is breast cancer.

In some embodiments, the methods for treating or preventing a cancer further comprise detecting overexpression of a LSD gene (e.g., LSD1 or LSD2) in a tumor sample obtained from the subject, wherein the tumor sample comprises the CSCs and optionally the non-CSC tumor cells, prior to administering the LSD inhibitor to the subject.

In some embodiments, the methods for treating or preventing a cancer further comprise detecting that the CSCs express one or more CSC markers as broadly described above prior to administering the LSD inhibitor to the subject.

Suitably, the LSD inhibitor and the cancer therapy agent are administered in synergistically effective amounts.

Typically, one or both of the LSD inhibitor and the cancer therapy or agent are administered on a routine schedule, for example, every day, at least twice a week, at least three times a week, at least four times a week, at least five times a week, at least six times a week, every week, every other week, every third week, every fourth week, every month, every two months, every three months, every four months, and every six months.

In some embodiments, the cancer therapy is likely to expose the subject to a higher risk of infection. Accordingly, in these embodiments, the methods may further comprise administering simultaneously, sequentially or separately with the LSD inhibitor and/or the cancer therapy/agent at least one anti-infective agent that is effective against an infection that develops or that has an increased risk of developing by administration of the cancer therapy, wherein the anti-infective agent is selected from antimicrobials, antibiotics, antivirals, antifungals, anthelmintics, antiprotozoals and nematocides.

In yet another aspect, the invention provides methods for identifying agents that are useful for inhibiting proliferation, survival or viability of a CSC or for treating or preventing a cancer in a subject, wherein the cancer comprises CSCs. These methods generally comprise contacting a preparation with a test agent, wherein the preparation comprises (i) a polypeptide comprising an amino acid sequence corresponding to at least a biologically active fragment of a LSD (e.g., LSD1 or LSD2), or to a variant or derivative thereof; or (ii) a polynucleotide comprising a nucleotide sequence from which a transcript of a LSD gene (e.g., LSD1 or LSD2) or portion thereof is producible, or (iii) a polynucleotide comprising at least a portion of a genetic sequence (e.g., a transcriptional element) that regulates the expression of a LSD gene (e.g., LSD1 or LSD2), which is operably linked to a reporter gene. A detected reduction in the level and/or functional activity of the polypeptide, transcript or transcript portion or an expression product of the reporter gene, relative to a normal or reference level and/or functional activity in the absence of the test agent, indicates that the agent is useful for inhibiting proliferation, survival or viability of a CSC or for treating or preventing the cancer.

Still another aspect of the present invention provides methods of producing an agent for inhibiting proliferation, survival or viability of a CSC or for treating or preventing a cancer that comprises CSCs, as broadly described above. These methods generally comprise: testing an agent suspected of inhibiting a LSD (e.g., LSD1 or LSD2) as broadly described above; and synthesizing the agent on the basis that it tests positive for the inhibition. Suitably, the method further comprises derivatizing the agent, and optionally formulating the derivatized agent with a pharmaceutically acceptable carrier and/or diluent, to improve the efficacy of the agent for inhibiting proliferation, survival or viability of a CSC or for treating or preventing a cancer that comprises CSCs.

Another aspect of the present invention provides pharmaceutical compositions for inhibiting proliferation, survival or viability of a CSC or for treating or preventing a cancer that comprises CSCs and non-CSC tumor cells, as broadly described above. These compositions generally comprise, consist or consist essentially of a LSD inhibitor (e.g., LSD1 or LSD2 inhibitor) and an agent that inhibits the proliferation, survival or viability of the non-CSC tumor cells.

In a further aspect, the present invention provides the use of a LSD inhibitor (e.g., LSD1 or LSD2 inhibitor) for inhibiting proliferation, survival or viability of a CSC or for treating or preventing a cancer comprising CSCs, as broadly described above.

Still another aspect of the present invention provides the use of a LSD inhibitor (e.g., LSD1 or LSD2 inhibitor) for enhancing the efficacy of a cancer therapy or agent that inhibits the proliferation, survival or viability of the non-CSC tumor cells.

In yet another aspect, the present invention provides the use of LSD inhibitor (e.g., LSD1 or LSD2 inhibitor) and a cancer therapy or agent that inhibits the proliferation, survival or viability of the non-CSC tumor cells for treating or preventing a cancer that comprises CSCs and non-CSC tumor cells, as broadly described above. In some embodiments, the LSD inhibitor and optionally the cancer therapy or agent are prepared or manufactured as medicaments for this purpose.

The present inventors have also found that it is possible to inhibit EMT of LSD-overexpressing non-CSC breast tumor cells and to induce mesenchymal-to-epithelial cell transition (MET) of breast CSCs by inhibiting the activity of LSDs (e.g., LSD1 and LSD2). Accordingly, it is proposed that LSD inhibitors are broadly useful for reducing or inhibiting the proliferation and EMT of LSD-overexpressing non-CSC tumor cells, and for inhibiting the proliferation, stimulating the death, and/or inducing MET of CSCs.

Thus, in another aspect, the present invention provides methods for altering at least one of: (i) formation; (ii) proliferation; (iii) survival; (iv) viability; (v) maintenance; (vi) EMT; or (vii) MET of a LSD (e.g., LSD1 or LSD2)-overexpressing cell. These methods generally comprise, consist or consist essentially of contacting the LSD-overexpressing cell with a formation-, proliferation-, survival-, viability-, maintenance-; EMT- or MET-modulating amount of a LSD (e.g., LSD1 or LSD2) inhibitor. Suitably, the LSD-overexpressing cell is selected from a CSC and a non-CSC tumor cell, illustrative examples of which include breast, prostate, lung, bladder, pancreatic, colon, melanoma, liver or glioma CSC and non-CSC tumor cells. In some embodiments, the CSC is a breast CSC (e.g., a breast epithelial CSC, including a breast ductal epithelial CSC). In some embodiments, the non-CSC tumor cell is a breast non-CSC tumor cell (e.g., a breast epithelial non-CSC tumor cell, including a breast ductal epithelial non-CSC tumor cell). Suitably, the LSD-overexpressing cell is contacted with one or more of a LSD-overexpressing cell formation-inhibiting, proliferation-inhibiting, survival-inhibiting, viability-inhibiting, maintenance-inhibiting, EMT-inhibiting amount or MET-stimulating/inducing amount of the LSD inhibitor.

In some embodiments in which the LSD-overexpressing cell is a CSC, the CSC expresses one or more (e.g., 1, 2, 3, 4, 5, 6, 7, 8 or more) CSC markers selected from ABCB5, ALDH1, ABCG2, $\alpha_6$ integrin, $\alpha_2 \beta_1$ integrin, β-catenin activity, CD15, CD13, CD20, CD24, CD26, CD29, CD44, CD90, CD133, CD166, CD271, c-Met, Hedgehog-Gli, Nestin, CXCR4, LGR5, Trop2 and Nodal-Activin. In some embodiments, the CSC expresses one or more (e.g., 1, 2, 3, 4, 5, 6, 7, 8 or more) CSC markers selected from ALDH1, CD24, CD44, CD90, CD133, Hedgehog-Gli, $\alpha_6$ integrin. In illustrative examples of this type, the CSC expresses CD24 and CD44 (e.g., $CD44^{high}$, $CD24^{low}$).

In some embodiments, the methods for altering at least one of: (i) formation; (ii) proliferation; (iii) survival; (iv) viability; (v) maintenance; (vi) EMT; or (vii) MET of the LSD-overexpressing cell further comprise detecting overexpression of a LSD gene (e.g., LSD1 or LSD2) (e.g., relative to the expression of the LSD gene in a normal cell (e.g., a normal breast cell)) in the LSD-overexpressing cell prior to contacting the LSD-overexpressing cell with the LSD inhibitor. In non-limiting examples of this type, the methods comprise detecting overexpression of the LSD gene in a CSC. In other non-limiting examples, the methods comprise detecting overexpression of the LSD gene in a non-CSC tumor cell. In still other non-limiting examples, the methods comprise detecting overexpression of the LSD gene in a CSC and a non-CSC tumor cell.

Suitably, the methods for altering at least one of: (i) formation; (ii) proliferation; (iii) survival; (iv) viability; (v) maintenance; (vi) EMT; or (vii) MET of the LSD-overexpressing cell further comprise detecting that the LSD-overexpressing cell expresses one or more CSC markers as broadly described above.

In another aspect, the present invention provides methods for treating or preventing a cancer (e.g., a metastatic cancer) in a subject, wherein the cancer comprises at least one LSD-overexpressing cell (e.g., a LSD1 or LSD2-overexpressing cell). These methods generally comprise, consist or consist essentially of administering to the subject a LSD inhibitor in an effective amount to alter at least one of: (i) formation; (ii) proliferation; (iii) survival; (iv) viability; (v) maintenance; (vi) EMT; or (vii) MET of the at least one LSD-overexpressing cell. Suitably, the LSD inhibitor is administered to the subject in an effective amount to inhibit (i) formation, (ii) proliferation, (iii) survival, (iv) viability, (v) maintenance, or (vi) EMT of the at least one LSD-overexpressing cell, or to stimulate or induce (vii) MET of the at least one LSD-overexpressing cell. In some embodiments, the LSD inhibitor is a selective LSD inhibitor. In other embodiments, the LSD inhibitor is a non-selective LSD inhibitor. Suitably, the at least one LSD-overexpressing cell is selected from a CSC and a non-CSC tumor cell.

In some embodiments, the cancer is selected from breast, prostate, lung, bladder, pancreatic, colon, melanoma, liver or glioma cancer. Suitably, the cancer is breast cancer. In some embodiments, the CSCs give rise to non-CSC tumor cells that are hormone-resistant.

In some embodiments, the methods for treating or preventing a cancer further comprise detecting overexpression of a LSD gene in a tumor sample obtained from the subject, wherein the tumor sample comprises the at least one LSD-overexpressing cell (e.g., a CSC and/or a non-CSC tumor cell), prior to administering the LSD inhibitor to the subject.

In some embodiments, the methods for treating or preventing a cancer further comprise detecting expression of one or more CSC markers as broadly described above in a tumor sample obtained from the subject, wherein the tumor sample comprises the at least one LSD-overexpressing cell, prior to administering the LSD inhibitor to the subject.

Yet another aspect of the present invention provides methods for treating or preventing a cancer (e.g., a metastatic cancer) in a subject, wherein the cancer comprises a CSC and a non-CSC tumor cell. These methods generally comprise, consist or consist essentially of concurrently administering to the subject (1) a LSD inhibitor in an effective amount to inhibit at least one of: (i) formation, (ii) proliferation, (iii) survival, (iv) viability, or (v) maintenance of the CSC and/or the non-CSC tumor cell; and/or to inhibit (vi) EMT of the CSC; and/or to stimulate or induce (vii) MET of the CSC, and (2) a cancer therapy or agent that inhibits the proliferation, survival or viability of the non-CSC tumor cell, to thereby treat or prevent the cancer. Suitably, the LSD inhibitor is administered to the subject in an effective amount to inhibit (i) formation, (ii) proliferation, (iii) survival, (iv) viability, or (v) maintenance of the CSC and/or non-CSC tumor cell, and/or to inhibit (vi) EMT of the CSC, and/or to stimulate or induce (vii) MET of the CSC. In some embodiments, the LSD inhibitor is a selective LSD inhibitor. In other embodiments, the LSD inhibitor is a non-selective LSD inhibitor. In some embodiments, the cancer therapy or agent is selected from radiotherapy, surgery, chemotherapy, hormone ablation therapy, pro-apoptosis therapy and immunotherapy. In illustrative examples of this type, the cancer therapy or agent targets rapidly dividing cells or disrupts the cell cycle or cell division.

Suitably, the methods further comprise identifying that the subject has or is at risk of developing a cancer comprising the CSC and the non-CSC tumor cell prior to the co-administration. In some embodiments, the cancer is selected from breast, prostate, lung, bladder, pancreatic, colon, melanoma, liver or glioma cancer. Suitably, the cancer is selected from breast, prostate, lung, bladder, pancreatic, colon, melanoma, liver or brain cancer.

In some embodiments, the methods for treating or preventing a cancer further comprise detecting overexpression of a LSD gene (e.g., relative to the expression of LSD in a normal cell (e.g., a normal breast cell)) in a tumor sample obtained from the subject, wherein the tumor sample comprises the CSC or the non-CSC tumor cell or both, prior to administering the LSD inhibitor to the subject.

In some embodiments, the methods for treating or preventing a cancer further comprise detecting that the CSC expresses one or more CSC markers as broadly described above prior to administering the LSD inhibitor to the subject.

Suitably, the LSD inhibitor and the cancer therapy agent are administered in synergistically effective amounts.

Typically, one or both of the LSD inhibitor and the cancer therapy or agent are administered on a routine schedule, for example, every day, at least twice a week, at least three times a week, at least four times a week, at least five times a week, at least six times a week, every week, every other week, every third week, every fourth week, every month, every two months, every three months, every four months, and every six months.

In yet another aspect, the invention provides methods for identifying agents that are useful for inhibiting (i) formation, (ii) proliferation, (iii) survival, (iv) viability, or (v) maintenance of a LSD (e.g., LSD1 or LSD2)-overexpressing cell (e.g., a CSC and/or a non-CSC tumor cell), or for inhibiting (vi) EMT of a LSD-overexpressing cell (e.g., a CSC), or for stimulating or inducing (vii) MET of a LSD-overexpressing cell (e.g., a CSC), or for treating or preventing a cancer in a subject, wherein the cancer comprises a LSD-overexpressing cell (e.g., a CSC and/or a non-CSC tumor cell). These methods generally comprise contacting a preparation with a test agent, wherein the preparation comprises (i) a polypeptide comprising an amino acid sequence corresponding to at least a biologically active fragment of a LSD, or to a variant or derivative thereof; or (ii) a polynucleotide comprising a nucleotide sequence from which a transcript of a LSD gene or portion thereof is producible, or (iii) a polynucleotide comprising at least a portion of a genetic sequence (e.g., a transcriptional element) that regulates the expression of a LSD gene, which is operably linked to a reporter gene. A detected reduction in the level and/or functional activity (e.g., as broadly described above) of the polypeptide, transcript or transcript portion or an expression product of the reporter gene, relative to a normal or reference level and/or functional activity in the absence of the test agent, indicates that the agent is useful for inhibiting (i) formation, (ii) proliferation, (iii) survival, (iv) viability, or (v) maintenance of a LSD-overexpressing cell (e.g., a CSC and/or a non-CSC tumor cell), or for inhibiting (vi) EMT of a LSD-overexpressing cell (e.g., a CSC), or for stimulating or inducing (vii) MET of a LSD-overexpressing cell (e.g., a CSC), or for treating or preventing a cancer.

Still another aspect of the present invention provides methods of producing an agent for inhibiting at least one of: (i) formation, (ii) proliferation, (iii) survival, (iv) viability, or (v) maintenance of a LSD (e.g., LSD1 or LSD2)-overexpressing cell (e.g., a CSC and/or a non-CSC tumor cell), or for inhibiting (vi) EMT of a LSD-overexpressing cell (e.g., a CSC), or for stimulating or inducing (vii) MET of a LSD-overexpressing cell (e.g., a CSC), or for treating or preventing a cancer in a subject, wherein the cancer comprises a LSD-overexpressing cell (e.g., a CSC and/or a non-CSC tumor cell), as broadly described above. These methods generally comprise: testing an agent suspected of inhibiting a LSD as broadly described above; and synthesizing the agent on the basis that it tests positive for the inhibition. Suitably, the method further comprises derivatizing the agent, and optionally formulating the derivatized agent with a pharmaceutically acceptable carrier and/or diluent, to improve the efficacy of the agent for inhibiting (i) formation, (ii) proliferation, (iii) survival, (iv) viability, or (v) maintenance of a LSD-overexpressing cell (e.g., a CSC and/or a non-CSC tumor cell), or for inhibiting (vi) EMT of a LSD-overexpressing cell (e.g., a CSC), or for stimulating or inducing (vii) MET of a LSD-overexpressing cell (e.g., a CSC), or for treating or preventing a cancer in a subject, wherein the cancer comprises a LSD-overexpressing cell (e.g., a CSC and/or a non-CSC tumor cell).

Another aspect of the present invention provides pharmaceutical compositions for inhibiting at least one of: (i) formation, (ii) proliferation, (iii) survival, (iv) viability, or (v) maintenance of a CSC and/or a non-CSC tumor cell; and/or for inhibiting (vi) EMT of a CSC; and/or for stimulating (vii) MET of a CSC; and/or for treating or preventing a cancer that comprises a CSC and/or a non-CSC tumor cell, as broadly described above. These compositions generally comprise, consist or consist essentially of a LSD inhibitor and a second/auxiliary agent that inhibits the proliferation, survival or viability of the non-CSC tumor cell. In some embodiments, the LSD inhibitor is a selective LSD inhibitor. In other embodiments, the LSD inhibitor is a non-selective LSD inhibitor.

In a further aspect, the present invention provides the use of a LSD (e.g., LSD1 or LSD2) inhibitor for altering at least one of: (i) formation; (ii) proliferation; (iii) survival; (iv) viability; (v) maintenance; (vi) EMT; or (vii) MET of a LSD-overexpressing cell or for treating or preventing a cancer that comprises a LSD-overexpressing cell (e.g., a CSC or a non-CSC tumor cell), as broadly described above.

DETAILED DESCRIPTION OF THE INVENTION

1. Definitions

Figure 1:
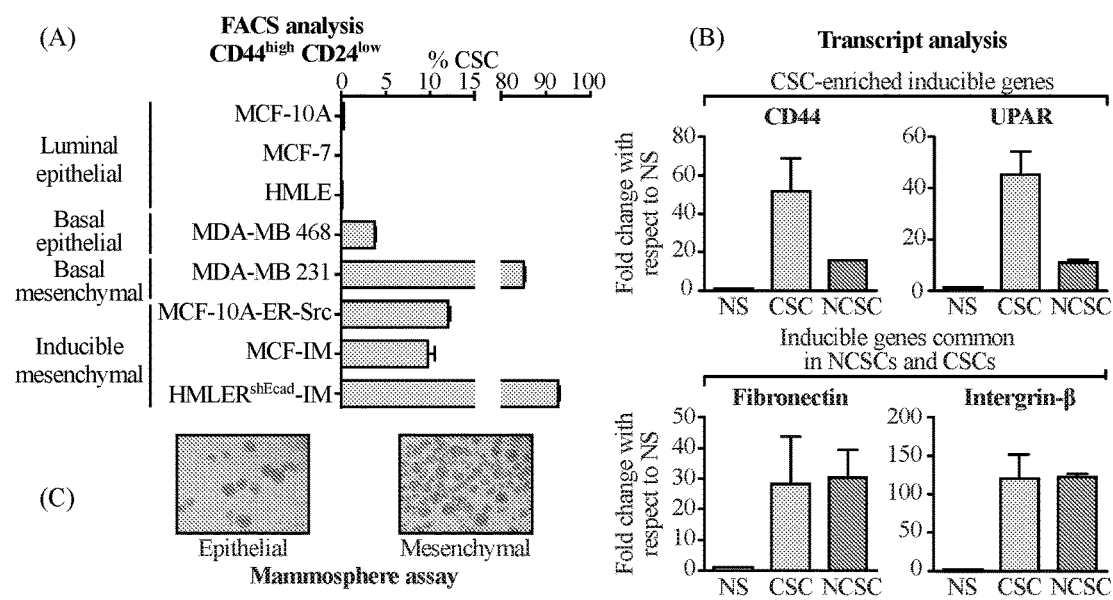
FIG. 1 is a graphical and photographic representation showing in vitro measurement of (A) key surface markers of human breast CSCs; (B) CSC-inducible genes in human breast CSCs; and (C) mammospheres in cell culture.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" or "modulatory agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative according to the invention to produce an antigenic or immunogenic response in an animal, suitably a mammal, to which it is administered, wherein the response includes the production of elements which specifically bind the polypeptide or fragment thereof.

As used herein, the term "alkyl" refers to a straight chain, branched or cyclic saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl, decyl, cyclopropyl, cyclobutyl, cyclopentyl, cyclohexyl and cycloheptyl.

As used herein, the term "alkenyl" refers to a straight-chain, branched or cyclic hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl, decenyl, cyclopentenyl, cyclohexenyl and cyclohexadienyl.

"Aralkyl" means alkyl as defined above which is substituted with an aryl group as defined above, e.g., —CH₂phenyl, —(CH₂)₂phenyl, —(CH₂)₃phenyl, —H₂CH(CH₃)CH₂phenyl, and the like and derivatives thereof.

As used herein, "aromatic" or "aryl" is intended to mean any stable monocyclic or bicyclic carbon ring of up to 7 atoms in each ring, wherein at least one ring is aromatic.

Examples of such aryl elements include, but are not limited to, phenyl, naphthyl, tetrahydronaphthyl, indanyl, biphenyl, phenanthryl, anthryl or acenaphthyl.

In certain instances, substituents may be defined with a range of carbons that includes zero, such as $(C_0-C_6)$alkylene-aryl. If aryl is taken to be phenyl, this definition would include phenyl itself as well as, for example, —$CH_2$Ph, —$CH_2CH_2$Ph, $CH(CH_3)CH_2CH(CH_3)$Ph.

It will also be recognized that the compounds described herein may possess asymmetric centers and are therefore capable of existing in more than one stereoisomeric form. The invention thus also relates to compounds in substantially pure isomeric form at one or more asymmetric centers e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

As used herein, the term "binds specifically," "specifically immuno-interactive" and the like when referring to an antigen-binding molecule refers to a binding reaction which is determinative of the presence of an antigen in the presence of a heterogeneous population of proteins and other biologics. Thus, under designated immunoassay conditions, the specified antigen-binding molecules bind to a particular antigen and do not bind in a significant amount to other proteins or antigens present in the sample. Specific binding to an antigen under such conditions may require an antigen-binding molecule that is selected for its specificity for a particular antigen. For example, antigen-binding molecules can be raised to a selected protein antigen, which bind to that antigen but not to other proteins present in a sample. A variety of immunoassay formats may be used to select antigen-binding molecules specifically immuno-interactive with a particular protein. For example, solid-phase ELISA immunoassays are routinely used to select monoclonal antibodies specifically immuno-interactive with a protein. See Harlow and Lane (1988) Antibodies, A Laboratory Manual, Cold Spring Harbor Publications, New York, for a description of immunoassay formats and conditions that can be used to determine specific immunoreactivity.

The term "cancer stem cell" or CSC refers to a cell that has tumor-initiating and tumor-sustaining capacity, including the ability to extensively proliferate, form new tumors and maintain cancer development, i.e., cells with indefinite proliferative potential that drive the formation and growth of tumors. CSCs are biologically distinct from the bulk tumor cells and possess characteristics associated with stem cells, specifically the ability to self renew and to propagate and give rise to all cell types found in a particular cancer sample. The term "cancer stem cell" or CSC includes both gene alteration in stem cells (SCs) and gene alteration in a cell which becomes a CSC. In specific embodiments, the CSCs breast CSCs, which are suitably $CD24^+$ $CD44^+$, illustrative examples of which include $CD44^{high}$ $CD24^{low}$.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "corresponds to" or "corresponding to" is meant a nucleic acid sequence that displays substantial sequence identity to a reference nucleic acid sequence (e.g., at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

The term "derivatize," "derivatizing" and the like refer to producing or obtaining a compound from another substance by chemical reaction, e.g., by adding one or more reactive groups to the compound by reacting the compound with a functional group-adding reagent, etc.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions or deletions that provide for functional equivalent molecules.

The term "differentiation" of cancer stem cells as used herein refers to both the change of cancer stem cells into pluripotent tumor progenitors and the change of pluripotent tumor progenitors into unipotent tumor progenitors and/or terminally differentiated tumor cells.

By "effective amount", in the context of treating or preventing a condition is meant the administration of an amount of an agent or composition to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

As used herein, the term "epithelial-to-mesenchymal transition" (EMT) refers to the conversion from an epithelial to a mesenchymal phenotype, which is a normal process of embryonic development. EMT is also the process whereby injured epithelial cells that function as ion and fluid transporters become matrix remodeling mesenchymal cells. In carcinomas, this transformation typically results in altered cell morphology, the expression of mesenchymal proteins and increased invasiveness. The criteria for defining EMT in vitro involve the loss of epithelial cell polarity, the separation into individual cells and subsequent dispersion after the acquisition of cell motility (see, Vincent-Salomon et al., Breast Cancer Res. 2003; 5(2): 101-106). Classes of molecules that change in expression, distribution, and/or function during EMT, and that are causally involved, include growth factors (e.g., transforming growth factor (TGF)-β, wnts), transcription factors (e.g., Snail, SMAD, LEF, and nuclear β-catenin), molecules of the cell-to-cell adhesion axis (cadherins, catenins), cytoskeletal modulators (Rho family), and extracellular proteases (matrix metalloproteinases, plasminogen activators) (see, Thompson et al., Cancer Research 65, 5991-5995, Jul. 15, 2005).

As used herein, the term "epithelium" refers to the covering of internal and external surfaces of the body, including the lining of vessels and other small cavities. It consists of a collection of epithelial cells forming a relatively thin sheet or layer due to the constituent cells being mutually and extensively adherent laterally by cell-to-cell junctions. The layer is polarized and has apical and basal sides. Despite the tight regimentation of the epithelial cells the epithelium does have some plasticity and cells in an epithelial layer can alter shape, such as change from flat to columnar, or pinch in at one end and expand at the other. However, these tend to occur in cell groups rather than individually (see, Thompson et al., 2005, supra).

The term "expression" refers the biosynthesis of a gene product. For example, in the case of a coding sequence, expression involves transcription of the coding sequence into mRNA and translation of mRNA into one or more polypeptides. Conversely, expression of a non-coding sequence involves transcription of the non-coding sequence into a transcript only.

By "expression vector" is meant any genetic element capable of directing the transcription of a polynucleotide contained within the vector and suitably the synthesis of a peptide or polypeptide encoded by the polynucleotide. Such expression vectors are known to practitioners in the art.

As used herein, the term "function" refers to a biological, enzymatic, or therapeutic function.

The term "gene" as used herein refers to any and all discrete coding regions of the cell's genome, as well as associated non-coding and regulatory regions. The term is intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The term "group" as applied to chemical species refers to a set of atoms that forms a portion of a molecule. In some instances, a group can include two or more atoms that are bonded to one another to form a portion of a molecule. A group can be monovalent or polyvalent (e.g., bivalent) to allow bonding to one or more additional groups of a molecule. For example, a monovalent group can be envisioned as a molecule with one of its hydrogen atoms removed to allow bonding to another group of a molecule. A group can be positively or negatively charged. For example, a positively charged group can be envisioned as a neutral group with one or more protons (i.e., $H^+$) added, and a negatively charged group can be envisioned as a neutral group with one or more protons removed. Non-limiting examples of groups include, but are not limited to, alkyl groups, alkylene groups, alkenyl groups, alkenylene groups, alkynyl groups, alkynylene groups, aryl groups, arylene groups, iminyl groups, iminylene groups, hydride groups, halo groups, hydroxy groups, alkoxy groups, carboxy groups, thio groups, alkylthio groups, disulfide groups, cyano groups, nitro groups, amino groups, alkylamino groups, dialkylamino groups, silyl groups, and siloxy groups. Groups such as alkyl, alkenyl, alkynyl, aryl, and heterocyclyl, whether used alone or in a compound word or in the definition of a group may be optionally substituted by one or more substituents. "Optionally substituted," as used herein, refers to a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, phenylamino, diphenylamino, benzylamino, dibenzylamino, hydrazino, acyl, acylamino, diacylamino, acyloxy, heterocyclyl, heterocycloxy, heterocyclamino, haloheterocyclyl, carboxy ester, carboxy, carboxy amide, mercapto, alkylthio, benzylthio, acylthio and phosphorus-containing groups. As used herein, the term "optionally substituted" may also refer to the replacement of a $CH_2$ group with a carbonyl (C=O) group. Non-limiting examples of optional substituents include alkyl, preferably $C_{1-8}$ alkyl (e.g., $C_{1-6}$ alkyl such as methyl, ethyl, propyl, butyl, cyclopropyl, cyclobutyl, cyclopentyl or cyclohexyl), hydroxy $C_{1-8}$ alkyl (e.g., hydroxymethyl, hydroxyethyl, hydroxypropyl), alkoxyalkyl (e.g., methoxymethyl, methoxyethyl, methoxypropyl, ethoxymethyl, ethoxyethyl, ethoxypropyl etc.) $C_{1-8}$ alkoxy, (e.g., $C_{1-6}$ alkoxy such as methoxy, ethoxy, propoxy, butoxy, cyclopropoxy, cyclobutoxy), halo (fluoro, chloro, bromo, iodo), monofluoromethyl, monochloromethyl, monobromomethyl, difluoromethyl, dichloromethyl, dibromomethyl, trifluoromethyl, trichloromethyl, tribromomethyl, hydroxy, phenyl (which itself may be further substituted, by an optional substituent as described herein, e.g., hydroxy, halo, methyl, ethyl, propyl, butyl, methoxy, ethoxy, acetoxy, amino), benzyl (wherein the $CH_2$ and/or phenyl group may be further substituted as described herein), phenoxy (wherein the $CH_2$ and/or phenyl group may be further substituted as described herein), benzyloxy (wherein the $CH_2$ and/or phenyl group may be further substituted as described herein), amino, $C_{1-8}$ alkylamino (e.g., $C_{1-6}$ alkyl, such as methylamino, ethylamino, propylamino), di $C_{1-8}$ alkylamino (e.g., $C_{1-6}$ alkyl, such as dimethylamino, diethylamino, dipropylamino), acylamino (e.g., $NHC(O)CH_3$), phenylamino (wherein phenyl itself may be further substituted as described herein), nitro, formyl, —C(O)—$C_{1-8}$ alkyl (e.g., $C_{1-6}$ alkyl, such as acetyl), O—C(O)-alkyl (e.g., $C_{1-6}$ alkyl, such as acetyloxy), benzoyl (wherein the $CH_2$ and/or phenyl group itself may be further substituted), replacement of $CH_2$ with C=O, $CO_2H$, $CO_2$ $C_{1-8}$ alkyl (e.g., $C_{1-6}$ alkyl such as methyl ester, ethyl ester, propyl ester, butyl ester), $CO_2$phenyl (wherein phenyl itself may be further substituted), $CONH_2$, CONHphenyl (wherein phenyl itself may be further substituted as described herein), CONHbenzyl (wherein the $CH_2$ and/or phenyl group may be further substituted as described herein), CONH $C_{1-8}$ alkyl (e.g., $C_{1-6}$ alkyl such as methyl amide, ethyl amide, propyl amide, butyl amide), CONH $C_{1-8}$ alkylamine (e.g., $C_{1-6}$ alkyl such as aminomethyl amide, aminoethyl amide, aminopropyl amide, aminobutyl amide), —C(O)heterocyclyl (e.g., —C(O)-1-piperidine, —C(O)-1-piperazine, —C(O)-4-morpholine), —C(O)heteroaryl (e.g., —C(O)-1-pyridine, —C(O)-1-pyridazine, —C(O)-1-pyrimidine, —C(O)-1-pyrazine), CONHdi $C_{1-8}$ alkyl (e.g., $C_{1-6}$alkyl).

"Heteroaralkyl" group means alkyl as defined above which is substituted with a heteroaryl group, e.g., —CH$_2$pyridinyl, —(CH$_2$)$_2$pyrimidinyl, —(CH$_2$)$_3$imidazolyl, and the like, and derivatives thereof.

The term "heteroaryl" or "heteroaromatic", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl.

Further examples of "heterocyclyl" and "heteroaryl" include, but are not limited to, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazoyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As used herein, "heteroarylene" refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-imidazolylene.

The term "heterocycle", "heteroaliphatic" or "heterocyclyl" as used herein is intended to mean a 5- to 10-membered nonaromatic heterocycle containing from 1 to 4 heteroatoms selected from the group consisting of O, N and S, and includes bicyclic groups.

"Heterocyclylalkyl" group means alkyl as defined above which is substituted with a heterocycle group, e.g., —CH$_2$pyrrolidin-1-yl, —(CH$_2$)$_2$piperidin-1-yl, and the like, and derivatives thereof.

The term "high," as used herein, refers to a measure that is greater than normal, greater than a standard such as a predetermined measure or a subgroup measure or that is relatively greater than another subgroup measure. For example, $CD44^{high}$ refers to a measure of CD44 that is greater than a normal CD44 measure. Consequently, "$CD44^{high}$" always corresponds to, at the least, detectable CD44 in a relevant part of a subject's body or a relevant sample from a subject's body. A normal measure may be determined according to any method available to one skilled in the art. The term "high" may also refer to a measure that is equal to or greater than a predetermined measure, such as a predetermined cutoff. If a subject is not "high" for a particular marker, it is "low" for that marker. In general, the cut-off used for determining whether a subject is "high" or "low" should be selected such that the division becomes clinically relevant.

"Homolog" is used herein to denote a gene or its product, which is related to another gene or product by decent from a common ancestral DNA sequence.

The term "hormone receptor negative (HR−) tumor" means a tumor that does not express a receptor for a hormone that stimulates the proliferation, survival or viability of the tumor above a certain threshold as determined by standard methods (e.g., immunohistochemical staining of nuclei in the patients biological samples. The threshold may be measured, for example, using an Allred score or gene expression. See, e.g., Harvey et al. (1999. *J Clin Oncol* 17:1474-1481) and Badve et al. (2008. *J Clin Oncol* 26(15): 2473-2481). In some embodiments, the tumor does not express an estrogen receptor (ER−) and/or a progesterone receptor (PR−).

The term "hormone receptor positive (HR+) tumor" means a tumor that expresses a receptor for a hormone that stimulates the proliferation, survival or viability of the tumor above a certain threshold as determined by standard methods (e.g., immunohistochemical staining of nuclei in the patients biological samples. The threshold may be measured, for example, using an Allred score or gene expression. See, e.g., Harvey et al. (1999. *J Clin Oncol* 17:1474-1481) and Badve et al. (2008. *J Clin Oncol* 26(15):2473-2481). a tumor expressing either estrogen receptor (ER) or progesterone receptor (PR) as determined by standard methods (e.g., immunohistochemical staining of nuclei in the patients biological samples).

The term "hormone-resistant cancer" as used herein refers to a cancer that has a decreased or eliminated response to a hormone therapy or endocrine therapy when compared to a non-hormone-resistant cancer. From a biological and clinical standpoint, several patterns of resistance can be distinguished: A) tumors that are inherently insensitive to endocrine receptor (e.g., estrogen receptor) targeting despite endocrine receptor expression (pan-endocrine therapy resistance or de novo resistance); B) tumors that are hormone dependent but resistant to one or more specific endocrine therapies (agent-selective resistance; for example responded to tamoxifen but not aromatase inhibitor); and C) tumors that initially respond to endocrine therapy but subsequently progress (acquired resistance). All types of resistance are included herein. In some embodiments, the hormone-resistant cancer is a cancer that is hormone-resistant prior to the administration of a hormone or endocrine therapy (i.e., it is de novo hormone-resistant). In other embodiments, the hormone-resistant cancer is a cancer that is initially not hormone-resistant, but becomes hormone-resistant after at least one treatment of a hormone or endocrine therapy.

The term "hormone therapy" or "endocrine therapy" as used herein is defined as a treatment pertaining to blocking or removing hormones. The treatment may remove the gland that synthesizes the hormone or the prohormone, block or inhibit hormone synthesis, or prevent or inhibit the hormone from binding to its receptor, or down-regulate or degrade the hormone receptor.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances as known to those of skill in the art.

The phrase "hybridizing specifically to" and the like refer to the binding, duplexing, or hybridizing of a molecule only to a particular nucleotide sequence under stringent conditions when that sequence is present in a complex mixture (e.g., total cellular) DNA or RNA.

The term "hydrocarbyl" as used herein includes any radical containing carbon and hydrogen including saturated, unsaturated, aromatic, straight or branched chain or cyclic including polycyclic groups. Hydrocarbyl includes but is not limited to $C_1$-$C_8$alkyl, $C_2$-$C_8$alkenyl, $C_2$-$C_8$alkynyl, $C_3$-$C_{10}$cycloalkyl, aryl such as phenyl and naphthyl, Ar($C_1$-$C_8$)alkyl such as benzyl, any of which may be optionally substituted.

Reference herein to "immuno-interactive" includes reference to any interaction, reaction, or other form of association between molecules and in particular where one of the molecules is, or mimics, a component of the immune system.

As used herein, the term "inhibitor" means an agent that decreases or inhibits the function or biological activity of a LSD polypeptide (e.g., LSD1—also known as lysine-specific histone demethylase 1A; lysine (K)-specific demethylase 1 (KDM1); lysine (K)-specific demethylase 1A (KDM1A); BRAF35-HDAC complex protein BHC110; FAD-binding protein BRAF35-HDAC complex, 110 kDa subunit; amine oxidase (flavin containing) domain 2 (AOF2); lysine-specific histone demethylase 1; RP1-184J9.1—and LSD2—also known as lysine-specific histone demethylase 1B (KDM1B); amine oxidase flavin-containing 1 (AOF1); amine oxidase (flavin-containing) domain 1; flavin-containing amine oxidase domain-containing protein 1; lysine-specific histone demethylase 2; or the expression of a LSD gene (e.g., LSD1—also known as KDM1A; AOF2; BHC110; KDM1—and LSD2—also known as KDM1B; AOF1; bA204B7.3; C6orf193; dJ298J15.2).

The term "low," as used herein, refers to a measure that is lower than normal, lower than a standard such as a predetermined measure or a subgroup measure or that is relatively lower than another subgroup measure. For example, $CD24^{low}$ refers to a measure of CD24 that is lower than a normal CD24 measure. A normal measure may be determined according to any method available to one skilled in the art. The term "low" may also refer to a measure that is equal to or lower than a predetermined measure, such as a predetermined cutoff.

The term "lower alkyl" refers to straight and branched chain alkyl groups having from 1 to 6 carbon atoms, such as methyl, ethyl, n-propyl, iso-propyl, n-butyl, tert-butyl, sec-butyl, n-pentyl, n-hexyl, 2-methylpentyl, and the like. In some embodiments, the lower alkyl group is methyl or ethyl.

The term "lower alkoxy" refers to straight and branched chain alkoxy groups having from 1 to 6 carbon atoms, such as methoxy, ethoxy, n-propoxy, iso-propoxy, n-butoxy, tert-butoxy, sec-butoxy, n-pentoxy, n-hexoxy, 2-methyl-pentoxy, and the like. Usually, the lower alkoxy group is methoxy or ethoxy.

As used herein, the term "mesenchyme" refers to the part of the embryonic mesoderm, consisting of loosely packed, unspecialized cells set in a gelatinous ground substance, from which connective tissue, bone, cartilage, and the circulatory and lymphatic systems develop. Mesenchyme is a collection of cells which form a relatively diffuse tissue network. Mesenchyme is not a complete cellular layer and the cells typically have only points on their surface engaged in adhesion to their neighbors. These adhesions may also involve cadherin associations (see, Thompson et al., 2005, supra).

As used herein, the term "mesenchymal-to-epithelial transition" (MET) is a reversible biological process that involves the transition from motile, multipolar or spindle-shaped mesenchymal cells to planar arrays of polarized cells called epithelia. MET is the reverse process of EMT. METs occur in normal development, cancer metastasis, and induced pluripotent stem cell reprogramming.

By "modulating" is meant increasing or decreasing, either directly or indirectly, the level or functional activity of a target molecule. For example, an agent may indirectly modulate the level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably connected" or "operably linked" as used herein means placing a structural gene under the regulatory control of a regulatory element including but not limited to a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The terms "overexpress," "overexpression," or "overexpressed" interchangeably refer to a gene (e.g., a LSD gene) that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 10%, 20%, 30%, 40%, 50%, 60%, 70%, 80%, 90% or more in comparison to a normal cell or comparison cell (e.g., a breast cell).

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. In specific embodiments, the subject is a primate such as a human. However, it will be understood that the aforementioned terms do not imply that symptoms are present.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, transfection agents and the like.

Similarly, a "pharmacologically acceptable" salt, ester, amide, prodrug or derivative of a compound as provided herein is a salt, ester, amide, prodrug or derivative that this not biologically or otherwise undesirable.

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

"Phenylalkyl" means alkyl as defined above which is substituted with phenyl, e.g., —$CH_2$phenyl, —$(CH_2)_2$phenyl, —$(CH_2)_3$phenyl, $CH_3CH(CH_3)CH_2$phenyl, and the like and derivatives thereof. Phenylalkyl is a subset of the aralkyl group.

The terms "polynucleotide variant" and "variant" refer to polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally occurring allelic variants.

The terms "polypeptide," "proteinaceous molecule," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogs of an amino acid including, for example, unnatural amino acids or polypeptides with substituted linkages.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative.

As used herein, the terms "prevent," "prevented," or "preventing," refer to a prophylactic treatment which increases the resistance of a subject to developing the disease or condition or, in other words, decreases the likelihood that the subject will develop the disease or condition as well as a treatment after the disease or condition has begun in order to reduce or eliminate it altogether or prevent it from becoming worse. These terms also include within their scope preventing the disease or condition from occurring in a subject which may be predisposed to the disease or condition but has not yet been diagnosed as having it.

As used herein, "racemate" refers to a mixture of enantiomers.

The terms "reduce," "inhibit," "diminish," "suppress," "decrease," and grammatical equivalents when used in reference to the level of a substance and/or phenomenon in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, fatigue, etc. In another embodiment, the reduction may be determined objectively, for example when the number of CSCs and/or non-CSC tumor cells in a sample from a patient is lower than in an earlier sample from the patient. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample. Alternatively, a difference may be expressed as an "n-fold" difference.

The terms "salts," "derivatives" and "prodrugs" includes any pharmaceutically acceptable salt, ester, hydrate, or any other compound which, upon administration to the recipient, is capable of providing (directly or indirectly) a compound of the invention, or an active metabolite or residue thereof. Suitable pharmaceutically acceptable salts include salts of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Also, basic nitrogen-containing groups may be quaternized with such agents as lower alkyl halides, such as methyl, ethyl, propyl, and butyl chlorides, bromides and iodides; dialkyl sulfates like dimethyl and diethyl sulfate; and others. However, it will be appreciated that non-pharmaceutically acceptable salts also fall within the scope of the invention since these may be useful in the preparation of pharmaceutically acceptable salts. The preparation of salts and prodrugs and derivatives can be carried out by methods known in the art. For example, metal salts can be prepared by reaction of a compound of the invention with a metal hydroxide. An acid salt can be prepared by reacting an appropriate acid with a compound of the invention.

The term "selective" refers to compounds that inhibit or display antagonism towards a LSD without displaying substantial inhibition or antagonism towards another LSD or another enzyme such as a monoamine oxidase (MAO) (e.g., MAO A or MAO B). Accordingly, a compound that is selective for LSD1 exhibits a LSD1 selectivity of greater than about 2-fold, 5-fold, 10-fold, 20-fold, 50-fold or greater than about 100-fold with respect to inhibition or antagonism of another LSD (i.e., a LSD other than LSD1 such as LSD2) or of another enzyme (e.g., a MAO). In some embodiments, selective compounds display at least 50-fold greater inhibition or antagonism towards a specified LSD than towards another LSD or another enzyme (e.g., a MAO). In still other embodiments, selective compounds inhibit or display at least 100-fold greater inhibition or antagonism towards a specified LSD than towards another LSD or another enzyme (e.g., a MAO). In still other embodiments, selective compounds display at least 500-fold greater inhibition or antagonism towards L a specified LSD than towards another LSD or another enzyme (e.g., a MAO). In still other embodiments, selective compounds display at least 1000-fold greater inhibition or antagonism towards a specified LSD than towards another LSD or another enzyme (e.g., a MAO).

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table 2.

TABLE 2

| ORIGINAL RESIDUE | EXEMPLARY SUBSTITUTIONS |
| --- | --- |
| Ala | Ser |
| Arg | Lys |
| Asn | Gln, His |

TABLE 2-continued

| ORIGINAL RESIDUE | EXEMPLARY SUBSTITUTIONS |
|---|---|
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology," John Wiley & Sons Inc, 1994-1998, Chapter 15.

As used herein a "small molecule" refers to a composition that has a molecular weight of less than 3 kilodaltons (kDa), and typically less than 1.5 kilodaltons, and suitably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, less than 1.5 kilodaltons, or even less than about 1 kDa.

"Stringency" as used herein refers to the temperature and ionic strength conditions, and presence or absence of certain organic solvents, during hybridization. The higher the stringency, the higher will be the observed degree of complementarity between sequences. "Stringent conditions" as used herein refers to temperature and ionic conditions under which only polynucleotides having a high proportion of complementary bases, preferably having exact complementarity, will hybridize. The stringency required is nucleotide sequence dependent and depends upon the various components present during hybridization, and is greatly changed when nucleotide analogues are used. Generally, stringent conditions are selected to be about 10° C. to 20° C. less than the thermal melting point (Tm) for the specific sequence at a defined ionic strength and pH. The Tm is the temperature (under defined ionic strength and pH) at which 50% of a target sequence hybridizes to a complementary probe. It will be understood that a polynucleotide will hybridize to a target sequence under at least low stringency conditions, preferably under at least medium stringency conditions and more preferably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing 0.5 M sodium phosphate, 7% SDS at 65° C., followed by one or more washes at 0.2×SSC, 1% SDS at 65° C. Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see CURRENT PROTOCOLS IN MOLECULAR BIOLOGY (supra) at pages 2.10.1 to 2.10.16 and MOLECULAR CLONING. A LABORATORY MANUAL (Sambrook, et al., eds.) (Cold Spring Harbor Press 1989) at sections 1.101 to 1.104.

By "substantially complementary" it is meant that an oligonucleotide or a subsequence thereof is sufficiently complementary to hybridize with a target sequence. Accordingly, the nucleotide sequence of the oligonucleotide or subsequence need not reflect the exact complementary sequence of the target sequence. In a preferred embodiment, the oligonucleotide contains no mismatches and with the target sequence.

As used herein, the term "synergistic" means that the therapeutic effect of a LSD inhibitor (e.g., a LSD1 or LSD2 inhibitor) when administered in combination with a cancer therapy or agent (or vice-versa) is greater than the predicted additive therapeutic effects of the LSD inhibitor and the cancer therapy or agent when administered alone. The term "synergistically effective amount" as applied to a LSD inhibitor and a cancer therapy agent refers to the amount of each component in a composition (generally a pharmaceutical composition), which is effective for inhibiting the formation, proliferation, survival, viability or maintenance of CSCs and non-CSC tumor cells, to thereby treat or prevent the cancer, and which produces an effect which does not intersect, in a dose-response plot of the dose of LSD inhibitor versus a dose of the cancer therapy agent versus inhibiting the formation, proliferation, survival, viability or maintenance of CSCs and non-CSC tumor cells, either the dose LSD inhibitor axis or the dose cancer therapy agent axis. The dose response curve used to determine synergy in the art is described for example by Sande et al. (see, p. 1080-1105 in A. Goodman et al., ed., the Pharmacological Basis of Therapeutics, MacMillan Publishing Co., Inc., New York (1980)). The optimum synergistic amounts can be determined, using a 95% confidence limit, by varying factors such as dose level, schedule and response, and using a computer-generated model that generates isobolograms from the dose response curves for various combinations of the LSD inhibitor and the cancer therapy agent. The highest inhibition of formation, proliferation, survival, viability or maintenance of CSCs and non-CSC tumor cells on the dose response curve correlates with the optimum dosage levels.

As used herein, the terms "treatment," "treating," and the like, refer to obtaining a desired pharmacologic and/or physiologic effect. The effect may be therapeutic in terms of a partial or complete cure for a disease or condition (e.g., a hematologic malignancy) and/or adverse affect attributable to the disease or condition. These terms also cover any treatment of a condition or disease in a mammal, particularly in a human, and include: (a) inhibiting the disease or condition, i.e., arresting its development; or (b) relieving the disease or condition, i.e., causing regression of the disease or condition.

The term "tumor," as used herein, refers to any neoplastic cell growth and proliferation, whether malignant or benign, and all pre-cancerous and cancerous cells and tissues. The terms "cancer" and "cancerous" refer to or describe the physiological condition in mammals that is typically characterized in part by unregulated cell growth. As used herein, the term "cancer" refers to non-metastatic and metastatic cancers, including early stage and late stage cancers. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer. By "early stage cancer" is meant a cancer that is not invasive or metastatic or is classified as a Stage 0, I, or II cancer. The term "late stage cancer" generally refers to a Stage III or Stage IV cancer, but can also refer to a Stage II cancer or a substage of a Stage II cancer. One skilled in the art will appreciate that the classification of a Stage II cancer as either an early stage cancer or a late stage cancer depends on the particular type of cancer. Illustrative examples of cancer include, but are not limited to, breast cancer, prostate cancer, ovarian cancer, cervical cancer, pancreatic cancer, colorectal cancer, lung cancer, hepatocellular cancer, gastric cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, rectal cancer, and esophageal cancer. In an exemplary embodiment, the cancer is breast cancer.

The term "tumor sample" as used herein means a sample comprising tumor material obtained from a cancerous patient. The term encompasses clinical samples, for example tissue obtained by surgical resection and tissue obtained by biopsy, such as for example a core biopsy or a fine needle biopsy. The term also encompasses samples comprising tumor cells obtained from sites other than the primary tumor, e.g., circulating tumor cells, as well as well as preserved tumor samples, such as formalin-fixed, paraffin-embedded tumor samples or frozen tumor samples. The term encompasses cells that are the progeny of the patient's tumor cells, e.g., cell culture samples derived from primary tumor cells or circulating tumor cells. The term encompasses samples that may comprise protein or nucleic acid material shed from tumor cells in vivo, e.g., bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene, which confers resistance to the antibiotic hygromycin B.

As used herein, underscoring or italicizing the name of a gene shall indicate the gene, in contrast to its protein product, which is indicated by the name of the gene in the absence of any underscoring or italicizing. For example, "LSD1" shall mean the LSD1 gene, whereas "LSD1" shall indicate the protein product or products generated from transcription and translation and/or alternative splicing of the "LSD1" gene.

Each embodiment described herein is to be applied mutatis mutandis to each and every embodiment unless specifically stated otherwise.

2. Compositions and Methods for Reducing or Abrogating the Formation, Proliferation or Viability of Cancer Stem Cells The present invention is based in part on the determination that breast cancers, including hormone resistant breast cancers, are enriched for CSCs and that LSDs (e.g., LSD1 and LSD2) are overexpressed in those CSCs and in non-CSC tumor cells. Based on these findings, the present inventors treated breast CSCs with LSD (e.g., LSD1 and LSD2) inhibitors and found that they specifically stimulated CSC death as well as MET of CSCs. Without wishing to be bound by any theory or mode of operation, it is proposed that LSDs, including LSD1 and LSD2, play a critical role in transcription of CSC-specific genes by deregulating active chromatin domains across their regulatory regions and that this deregulation stimulates not only the production of breast CSCs but also the production of CSCs generally.

Based on the above observations, the present inventors propose that LSD (e.g., LSD1 and LSD2) inhibition will result in reduced proliferation, survival or viability of CSCs and/or non-CSC tumor cells, and/or in reduced EMT of CSC, and/or in increased MET of CSC, which will in turn result in fewer non-CSC tumor cells differentiating therefrom and in more effective treatment of non-CSC tumor cells with a cancer therapy or agent.

Thus, in accordance with the present invention, methods and compositions are provided that take advantage of a LSD inhibitor (e.g., a LSD1 or LSD2 inhibitor) to reduce or abrogate proliferation, survival or viability of CSCs and non-CSC tumor cells, and/or to reduce or abrogate EMT of CSC, and/or to stimulate or induce MET of CSC for the treatment or prophylaxis of a cancer (e.g., a metastatic cancer). In specific embodiments, the LSD inhibitor (e.g., a LSD1 or LSD2 inhibitor) is used in combination with a cancer therapy or agent that reduces the proliferation, survival or viability of non-CSC tumor cell progeny of those cells. The methods and compositions of the present invention are thus particularly useful in the treatment or prophylaxis of cancers, including metastatic cancers, as described hereafter.

2.1 LSD Inhibitors

The LSD inhibitor includes and encompasses any active agent that reduces the accumulation, function or stability of a LSD; or decrease expression of a LSD gene, and such inhibitors include without limitation, small molecules and macromolecules such as nucleic acids, peptides, polypeptides, peptidomimetics, carbohydrates, polysaccharides, lipopolysaccharides, lipids or other organic (carbon containing) or inorganic molecules.

In some embodiments, the LSD inhibitor is an antagonistic nucleic acid molecule that functions to inhibit the transcription or translation of LSD (e.g., LSD1 or LSD2) transcripts. Representative transcripts of this type include nucleotide sequences corresponding to any one the following sequences: (1) human LSD1 nucleotide sequences as set forth for example in GenBank Accession Nos. NM_015013.3, NP_001009999.1, and NM_001009999.2; human LSD2 nucleotide sequences as set forth for example in GenBank Accession No. NM_153042.3; (2) nucleotide sequences that share at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with any one of the sequences referred to in (1); (3) nucleotide sequences that hybridize under at least low, medium or high stringency conditions to the sequences referred to in (1); (4) nucleotide sequences that encode any one of the following amino acid sequences: human LSD1 amino acid sequences as set forth for example in GenPept Accession Nos. NP_055828.2, NP_001009999.1 and 060341.2; human LSD2 amino acid sequences as set forth for example in GenPept Accession Nos. NP_694587.3; (5) nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity with any one of the sequences referred to in (4); and nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with any one of the sequences referred to in (4).

Illustrative antagonist nucleic acid molecules include antisense molecules, aptamers, ribozymes and triplex forming molecules, RNAi and external guide sequences. The nucleic acid molecules can act as effectors, inhibitors, modulators, and stimulators of a specific activity possessed by a target molecule, or the functional nucleic acid molecules can possess a de novo activity independent of any other molecules.

Antagonist nucleic acid molecules can interact with any macromolecule, such as DNA, RNA, polypeptides, or carbohydrate chains. Thus, antagonist nucleic acid molecules can interact with LSD (e.g., LSD1 or LSD2) mRNA or the genomic DNA of LSD (e.g., LSD1 or LSD2) or they can interact with a LSD polypeptide e.g., LSD1 or LSD2). Often antagonist nucleic acid molecules are designed to interact with other nucleic acids based on sequence homology between the target molecule and the antagonist nucleic acid molecule. In other situations, the specific recognition between the antagonist nucleic acid molecule and the target molecule is not based on sequence homology between the antagonist nucleic acid molecule and the target molecule, but rather is based on the formation of tertiary structure that allows specific recognition to take place.

In some embodiments, anti-sense RNA or DNA molecules are used to directly block the translation of LSD (e.g., LSD1 or LSD2) by binding to targeted mRNA and preventing protein translation. Antisense molecules are designed to interact with a target nucleic acid molecule through either canonical or non-canonical base pairing. The interaction of the antisense molecule and the target molecule may be designed to promote the destruction of the target molecule through, for example, RNAseH mediated RNA-DNA hybrid degradation. Alternatively the antisense molecule may be designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Non-limiting methods include in vitro selection experiments and DNA modification studies using DMS and DEPC. In specific examples, the antisense molecules bind the target molecule with a dissociation constant ($K_d$) less than or equal to $10^{-6}$, $10^{-8}$, $10^{-10}$, or $10^{-12}$. In specific embodiments, antisense oligodeoxyribonucleotides derived from the translation initiation site, e.g., between −10 and +10 regions are employed.

Aptamers are molecules that interact with a target molecule, suitably in a specific way. Aptamers are generally small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with Kds from the target molecule of less than $10^{-12}$ M. Suitably, the aptamers bind the target molecule with a Kd less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is desirable that an aptamer have a $K_d$ with the target molecule at least 10-, 100-, 1000-, 10,000-, or 100,000-fold lower than the $K_d$ with a background-binding molecule. A suitable method for generating an aptamer to a target of interest (e.g., PHD, FIH-1 or vHL) is the "Systematic Evolution of Ligands by EXponential Enrichment" (SELEX™). The SELEX™ method is described in U.S. Pat. No. 5,475,096 and U.S. Pat. No. 5,270,163 (see also WO 91/19813). Briefly, a mixture of nucleic acids is contacted with the target molecule under conditions favorable for binding. The unbound nucleic acids are partitioned from the bound nucleic acids, and the nucleic acid-target complexes are dissociated. Then the dissociated nucleic acids are amplified to yield a ligand-enriched mixture of nucleic acids, which is subjected to repeated cycles of binding, partitioning, dissociating and amplifying as desired to yield highly specific high affinity nucleic acid ligands to the target molecule.

In other embodiments, anti-LSD (e.g., anti-LSD1 or LSD2) ribozymes are used for catalyzing the specific cleavage of LSD (e.g., LSD1 or LSD2) RNA. The mechanism of ribozyme action involves sequence specific hybridization of the ribozyme molecule to complementary target RNA, followed by a endonucleolytic cleavage. There are several different types of ribozymes that catalyze nuclease or nucleic acid polymerase type reactions, which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Representative ribozymes cleave RNA or DNA substrates. In some embodiments, ribozymes that cleave RNA substrates are employed. Specific ribozyme cleavage sites within potential RNA targets are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base pairing. Triplex molecules are preferred because they can bind target regions with high affinity and specificity. It is generally desirable that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNAse P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells.

In other embodiments, RNA molecules that mediate RNA interference (RNAi) of a LSD (e.g., LSD1 or LSD2) gene or LSD (e.g., LSD1 or LSD2) transcript can be used to reduce or abrogate gene expression. RNAi refers to interference with or destruction of the product of a target gene by introducing a single-stranded or usually a double-stranded RNA (dsRNA) that is homologous to the transcript of a target gene. RNAi methods, including double-stranded RNA interference (dsRNAi) or small interfering RNA (siRNA), have been extensively documented in a number of organisms, including mammalian cells and the nematode *C. elegans* (Fire et al., 1998. *Nature* 391, 806-811). In mammalian cells, RNAi can be triggered by 21- to 23-nucleotide (nt) duplexes of small interfering RNA (siRNA) (Chiu et al., 2002 *Mol. Cell.* 10:549-561; Elbashir et al., 2001. *Nature* 411:494-498), or by micro-RNAs (miRNA), functional small-hairpin RNA (shRNA), or other dsRNAs which are expressed in vivo using DNA templates with RNA polymerase III promoters (Zeng et al., 2002. *Mol. Cell* 9:1327-1333; Paddison et al., 2002. *Genes Dev.* 16:948-958; Lee et al., 2002. *Nature Biotechnol.* 20:500-505; Paul et al., 2002. *Nature Biotechnol.* 20:505-508; Tuschl, T., 2002. *Nature Biotechnol.* 20:440-448; Yu et al., 2002. *Proc. Natl. Acad. Sci. USA* 99(9):6047-6052; McManus et al., 2002. *RNA* 8:842-850; Sui et al., 2002. *Proc. Natl. Acad. Sci. USA* 99(6):5515-5520).

In specific embodiments, dsRNA per se and especially dsRNA-producing constructs corresponding to at least a portion of a LSD (e.g., LSD1 or LSD2) gene are used to reduce or abrogate its expression. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a LSD (e.g., LSD1 or LSD2) gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts, which then anneal to form a dsRNA having homology to a target gene.

Absolute homology is not required for RNAi, with a lower threshold being described at about 85% homology for a dsRNA of about 200 base pairs (Plasterk and Ketting, 2000, *Current Opinion in Genetics and Dev.* 10: 562-67). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are suitably at least about 100 nucleotides in length. RNA-encoding constructs that express a single RNA designed to form a dsRNA via internal folding are usually at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In some embodiments, RNA molecules of about 21 to about 23 nucleotides, which direct cleavage of specific mRNA to which they correspond, as for example described by Tuschl et al. in U.S. 2002/0086356, can be utilized for mediating RNAi. Such 21- to 23-nt RNA molecules can comprise a 3' hydroxyl group, can be single-stranded or double stranded (as two 21- to 23-nt RNAs) wherein the dsRNA molecules can be blunt ended or comprise overhanging ends (e.g., 5', 3').

In some embodiments, the antagonist nucleic acid molecule is a siRNA. siRNAs can be prepared by any suitable method. For example, reference may be made to International Publication WO 02/44321, which discloses siRNAs capable of sequence-specific degradation of target mRNAs when base-paired with 3' overhanging ends, which is incorporated by reference herein. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER™ siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which is incorporated herein by reference.

Illustrative RNAi molecules (e.g., LSD (e.g., LSD1 or LSD2) siRNA and shRNA) are described in the art (e.g., Yang, et al., 2010. *Proc. Natl. Acad. Sci. USA* 107: 21499-21504 and He et al., 2012. *Transcription* 3:3:1-16) or available commercially from Santa Cruz Biotechnology, Inc. (Santa Cruz, Calif., USA) and OriGene Technologies, Inc. (Rockville, Md., USA).

The present invention further contemplates peptide or polypeptide based inhibitor compounds. For example, BHC80 (also known as PHD finger protein 21A) forms part of a complex with LSD1 and can inhibit LSD1 demethylase activity. Accordingly, the present invention further contemplates the use of BHC80 or biologically active fragments thereof for inhibiting LSD1 enzymatic activity. Amino acid sequences of BHC80 polypeptides, and nucleotide sequences encoding BHC80 polypeptides, are publicly available. In this regard, reference may be made for example to GenBank Accession No. NP057705 for a *Homo sapiens* BHC80 amino acid sequence; and GenBank NM016621 for a nucleotide sequence encoding the amino acid sequence set forth in GenBank Accession No. NP057705; 2) GenBank Accession No. NP620094 for a *Mus musculus* BHC80 amino acid sequence; and GenBank NM138755 for a nucleotide sequence encoding the amino acid sequence set forth in GenBank Accession No. NP620094; 3) GenBank Accession No. NP00118576.1 for a *Gallus gallus* BHC80 amino acid sequence; and GenBank NM001199647 for a nucleotide sequence encoding the amino acid sequence set forth in GenBank Accession No. NP00118576.1; and 4) GenBank Accession No. DAA21793 for a *Bos taurus* BHC80 amino acid sequence.

Illustrative BHC80 polypeptides are selected from the group consisting of: (1) a polypeptide comprising an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity with the amino acid sequence listed in any one of the GenBank BHC80 polypeptide entries noted above; (2) a polypeptide comprising an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with the amino acid sequence listed in any one of the GenBank BHC80 polypeptide entries noted above; (3) a polypeptide comprising an amino acid sequence that is encoded by a nucleotide sequence that hybridizes under at least low, medium or high stringency conditions to the nucleotide sequence listed in any one of the GenBank BHC80 polynucleotide entries noted above; (4) a polypeptide comprising an amino acid sequence that is encoded by a nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity to the nucleotide sequence listed in any one of the GenBank BHC80 polynucleotide entries noted above; and (5) a fragment of a polypeptide according to any one of (1) to (4), which inhibits LSD1 enzymatic activity.

A BHC80 polypeptide can be introduced into a cell by delivering a polypeptide per se, or by introducing into the cell a BHC80 nucleic acid comprising a nucleotide sequence encoding a BHC80 polypeptide. In some embodiments, a BHC80 nucleic acid comprises a nucleotide sequence selected from: (1) a BHC80 nucleotide sequence listed in any one of the GenBank BHC80 polynucleotide entries noted above; (2) a nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with any one of the sequences referred to in (1); (3) a nucleotide sequence that hybridizes under at least low, medium or high stringency conditions to the sequences referred to in (1); (4) a nucleotide sequence that encodes an amino acid sequence listed in any one of the GenBank BHC80 polypeptide entries noted above; (5) a nucleotide sequence that encodes an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity with any one of the sequences referred to in (4); and a nucleotide sequence that encodes an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with any one of the sequences referred to in (4).

The BHC80 nucleic acid can be in the form of a recombinant expression vector. The BHC80 nucleotide sequence can be operably linked to a transcriptional control element(s), e.g., a promoter, in the expression vector. Suitable vectors include, e.g., recombinant retroviruses, lentiviruses, and adenoviruses; retroviral expression vectors, lentiviral expression vectors, nucleic acid expression vectors, and plasmid expression vectors. In some cases, the expression vector is integrated into the genome of a cell. In other cases, the expression vector persists in an episomal state in a cell.

Suitable expression vectors include, but are not limited to, viral vectors (e.g., viral vectors based on vaccinia virus; poliovirus; adenovirus (see, e.g., Li et al., Invest Opthalmol V is Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol V is Sci 38:2857 2863, 1997; Jomary et al., Gene Ther 4:683 690, 1997, Rolling et al., Hum Gene Ther 10:641 648, 1999; Ali et al., Hum Mol Genet. 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

The present invention also contemplates small molecule agents that reduce enzymatic activity of LSDs (e.g., LSD1 or LSD2).

Small molecule agents that reduce enzymatic activity of LSD1 that are suitable for use in the present invention include monoamine oxidase (MAO) inhibitors that also inhibit LSD1 enzymatic activity; polyamine compounds that inhibit LSD1 enzymatic activity; phenylcyclopropylamine derivatives that inhibit LSD1 enzymatic activity; and the like.

Non-limiting examples of MAO inhibitors include MAO-A-selective inhibitors, MAO-B-selective inhibitors, and MAO non-selective inhibitors. Illustrative examples of MAO inhibitors include reported inhibitors of the MAO-A isoform, which preferentially deaminates 5-hydroxytryptamine (serotonin) (5-HT) and norepinephrine (NE), and/or the MAO-B isoform, which preferentially deaminates phenylethylamine (PEA) and benzylamine (both MAO-A and MAO-B metabolize Dopamine (DA)). In various embodiments, MAO inhibitors may be irreversible or reversible (e.g., reversible inhibitors of MAO-A (RIMA)), and may have varying potencies against MAO-A and/or MAO-B (e.g., non-selective dual inhibitors or isoform-selective inhibitors).

In some embodiments, the MAO inhibitors are selected from: clorgyline; L-deprenyl; isocarboxazid (Marplan™); ayahuasca; nialamide; iproniazide; iproclozide; moclobemide (Aurorix™; 4-chloro-N-(2-morpholin-4-ylethyl)benzamide); phenelzine (Nardil™; (±)-2-phenylethylhydrazine); tranylcypromine (Parnate™; (±)-trans-2-phenylcyclopropan-1-amine) (the congeneric of phenelzine); toloxatone; levo-deprenyl (Selegiline™); harmala; RIMAs (e.g., moclobemide, described in Da Prada et al. (1989. *J Pharmacol Exp Ther* 248:400-414); brofaromine; and befloxatone, described in Curet et al. (1998. *J Affect Disord* 51: 287-30), lazabemide (Ro 19 6327), described in *Ann. Neurol.*, 40(1): 99-107 (1996), and SL25.1131, described in Aubin et al. (2004. *J. Pharmacol. Exp. Ther.* 310: 1171-1182); selegiline hydrochloride (1-deprenyl, ELDEPRYL, ZELAPAR); dimethylselegilene; safinamide; rasagiline (AZILECT); bifemelane; desoxypeganine; harmine (also known as telepathine or banasterine); linezolid (ZYVOX, ZYVOXID); pargyline (EUDATIN, SUPIRDYL); dienolide kavapyrone desmethoxyyangonin; 5-(4-Arylmethoxyphenyl)-2-(2-cyanoethyl)tetrazoles; and the like.

Small molecule LSD1 inhibitors may also be selected from polyamine compounds as described for example by Woster et al. in U.S. Publication No. 2007/0208082, which is incorporated herein by reference in its entirety. Illustrative polyamine inhibitors of LSD1 include compounds according to formula (I):

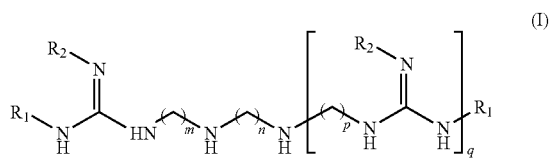

or a salt, solvate, or hydrate thereof, where n is an integer from 1 to 12; m and p are independently an integer from 1 to 5; q is 0 or 1; each $R_1$ is independently selected from the group consisting of $C_1$-$C_8$ alkyl, $C_4$-$C_{15}$ cycloalkyl, $C_3$-$C_{15}$ branched alkyl, $C_6$-$C_{20}$ aryl, $C_6$-$C_{20}$ heteroaryl, $C_7$-$C_{24}$ aralkyl, $C_7$-$C_{24}$ heteroaralkyl, and

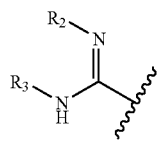

where $R_3$ is selected from the group consisting of $C_1$-$C_8$ alkyl, $C_4$-$C_{15}$ cycloalkyl, $C_3$-$C_{15}$ branched alkyl, $C_6$-$C_{20}$ aryl, $C_6$-$C_{20}$ heteroaryl, $C_7$-$C_{24}$ aralkyl and $C_7$-$C_{24}$ heteroaralkyl; and each $R_2$ is independently selected from hydrogen or a $C_1$-$C_8$ alkyl.

A suitable polyamine compound is a compound of Formula (I), wherein one or both $R_1$ is a $C_6$-$C_{20}$ aryl, such as a single ring aryl, including without limitation, a phenyl. In one embodiment, the compound is of the formula (I) and each $R_1$ is phenyl. In one embodiment, q is I, m and p are 3, and n is 4. In another embodiment, q is I, m and p are 3, and n is 7.

A suitable polyamine compound is a compound of Formula (I), where at least one or both $R_1$ is a $C_8$-$C_{12}$ or a $C_1$-$C_8$ alkyl, such as a linear alkyl. One or both $R_1$ may be a $C_1$-$C_8$ linear alkyl, such as methyl or ethyl. In one embodiment, each $R_1$ is methyl. One or both $R_1$ may comprise or be a $C_4$-$C_{15}$ cycloalkyl group, such as a cycloalkyl group containing a linear alkyl group, where the cycloalkyl group is connected to the molecule either via its alkyl or cycloalkyl moiety. For instance, one or both $R_1$ may be cyclopropylmethyl or cyclohexylmethyl. In one embodiment, one $R_1$ is cyclopropylmethyl or cyclohexylmethyl and the other $R_1$ is a linear alkyl group, such as a linear $C_1$-$C_8$ unsubstituted alkyl group, including without limitation an ethyl group. In one embodiment, $R_1$ is a $C_3$-$C_{15}$ branched alkyl group such as isopropyl. When $R_1$ is a $C_1$-$C_8$ substituted alkyl, the substituted alkyl may be substituted with any substituent, including a primary, secondary, tertiary or quaternary amine. Accordingly, in one embodiment, $R_1$ is a $C_1$-$C_8$ alkyl group substituted with an amine such that $R_1$ may be e.g., alkyl-$NH_2$ or an alkyl-amine-alkyl moiety such as —$(CH_2)_y$NH$(CH_2)_z$CH$_3$ where y and z are independently an integer from 1 to 8. In one embodiment, $R_1$ is —$(CH_2)_3$NH$_2$.

In one embodiment, the compound is of the formula (I) where one or both $R_1$ is a $C_7$-$C_{24}$ substituted or unsubstituted aralkyl, which in one embodiment is an aralkyl connected to the molecule via its alkyl moiety (e.g., benzyl). In one embodiment, both $R_1$ are aralkyl moieties wherein the alkyl portion of the moiety is substituted with two aryl groups and the moiety is connected to the molecule via its alkyl group. For instance, in one embodiment one or both $R_1$ is a $C_7$-$C_{24}$ aralkyl wherein the alkyl portion is substituted with two phenyl groups, such as when $R_1$ is 2,2-diphenylethyl or 2,2-dibenzylethyl. In one embodiment, both $R_1$ of formula (I) is 2,2-diphenylethyl and n is 1, 2 or 5. In one embodiment, each $R_1$ of formula (I) is 2,2-diphenylethyl, n is 1, 2 or 5 and m and p are each 1.

In one embodiment, at least one $R_1$ is hydrogen. When one $R_1$ is hydrogen, the other $R_1$ may be any moiety listed above for $R_1$, including an aryl group such as benzyl. Any of the compounds of formula (I) listed above include compounds where at least one or both of $R_2$ is hydrogen or a $C_1$-$C_8$ substituted or unsubstituted alkyl. In one embodiment, each $R_2$ is an unsubstituted alkyl such as methyl. In another embodiment, each $R_2$ is hydrogen. Any of the compounds of formula (I) listed above may be compounds where q is 1 and m and p are the same. Accordingly, the polyaminoguanidines of formula (I) may be symmetric with reference to the polyaminoguanidine core (e.g., excluding $R_1$). Alternatively, the compounds of formula (I) may be asymmetric, e.g., when q is 0. In one embodiment, m and p are 1. In one embodiment, q is 0. In one embodiment, n is an integer from 1 to 5.

In some embodiments, the compound is a polyaminobiguanide or N-alkylated polyaminobiguanide. An N-alkylated polyaminobiguanide intends a polyaminobiguanide where at least one imine nitrogen of at least one biguanide is alkylated. In one embodiment, the compound is a polyaminobiguanide of the formula (I), or a salt, solvate, or hydrate thereof, where q is 1, and at least one or each $R_1$ is of the structure:

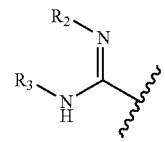

where each $R_3$ is independently selected from the group consisting of $C_1$-$C_8$ alkyl, $C_6$-$C_{20}$ aryl, $C_6$-$C_{20}$ heteroaryl, $C_7$-$C_{24}$ aralkyl, and $C_7$-$C_{24}$ heteroaralkyl; and each $R_2$ is independently hydrogen or a $C_1$-$C_8$ alkyl.

In one embodiment, in the polyaminobiguanide compound, at least one or each $R_3$ is a $C_1$-$C_8$ alkyl. For instance, when $R_3$ is a $C_1$-$C_8$ alkyl, the alkyl may be substituted with any substituent, including a primary, secondary, tertiary or quaternary amine. Accordingly, in one embodiment, $R_3$ is a $C_1$-$C_8$ alkyl group substituted with an amine such that $R_3$ may be e.g., alkyl-$NH_2$ or an alkyl-amine-alkyl moiety such as —$(CH_2)_y$NH$(CH_2)_z$CH$_3$ where y and z are independently an integer from 1 to 8. In one embodiment, $R_3$ is —$(CH_2)_3$NH$_2$. $R_3$ may also be a $C_4$-$C_{15}$ cycloalkyl or a $C_3$-$C_{15}$ branched alkyl. In one embodiment, at least one or each $R_3$ is a $C_6$-$C_{20}$ aryl. In one embodiment, q is I, m and p are 3, and n is 4. In another embodiment, q is I, m and p are 3, and n is 7.

In one embodiment, the compound is a polyaminobiguanide of formula (I) where at least one $R_3$ is a $C_7$-$C_{24}$ aralkyl, which in one embodiment is an aralkyl connected to the molecule via its alkyl moiety. In one embodiment, each $R_3$ is an aralkyl moiety where the alkyl portion of the moiety is substituted with one or two aryl groups and the moiety is connected to the molecule via its alkyl moiety. For instance, in one embodiment at least one or each $R_3$ is an aralkyl where the alkyl portion is substituted with two phenyl or benzyl groups, such as when $R_3$ is 2,2-diphenylethyl or 2,2-dibenzylethyl. In one embodiment, each $R_3$ is 2,2-diphenylethyl and n is 1, 2 or 5. In one embodiment, each $R_3$ is 2,2-diphenylethyl and n is 1, 2 or 5 and m and p are each 1.

Any of the polyaminobiguanide compounds of formula (I) listed above include compounds where at least one or both of $R_2$ is hydrogen or a $C_1$-$C_8$ alkyl. In one embodiment, each $R_2$ is an unsubstituted alkyl, such as methyl. In another embodiment, each $R_2$ is a hydrogen.

Any of the polyaminobiguanide compounds of formula (I) listed above include compounds where q is 1 and m and p are the same. Accordingly, the polyaminobiguanides of formula (I) may be symmetric with reference to the polyaminobiguanide core. Alternatively, the compounds of formula (I) may be asymmetric. In one embodiment, m and p are 1. In one embodiment, q is 0. In one embodiment, n is an integer from 1 to 5. In one embodiment, q, m and p are each 1 and n is 1, 2 or 5.

It is understood and clearly conveyed by this disclosure that each $R_1$, $R_2$, $R_3$, m, n, p and q disclosed in reference to formula (I) intends and includes all combinations thereof the same as if each and every combination of $R_1$, $R_2$, $R_3$, m, n, p and q were specifically and individually listed.

Representative compounds of the formula (I) include, e.g.:

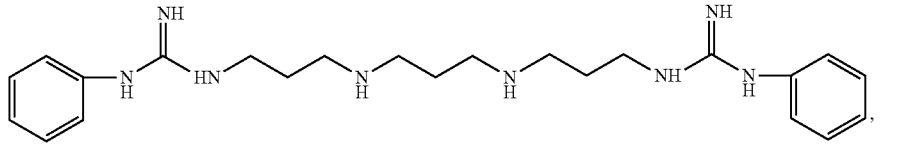
B188-2

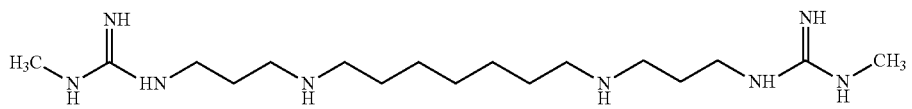
B181

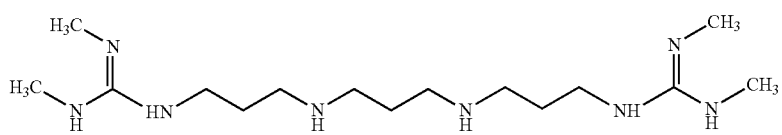
B182

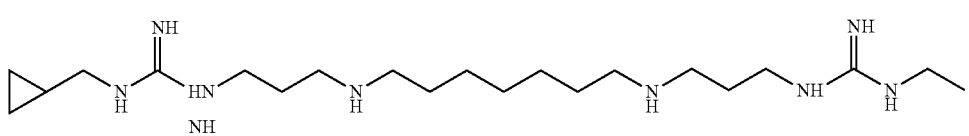
B291

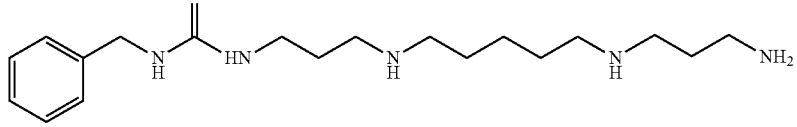

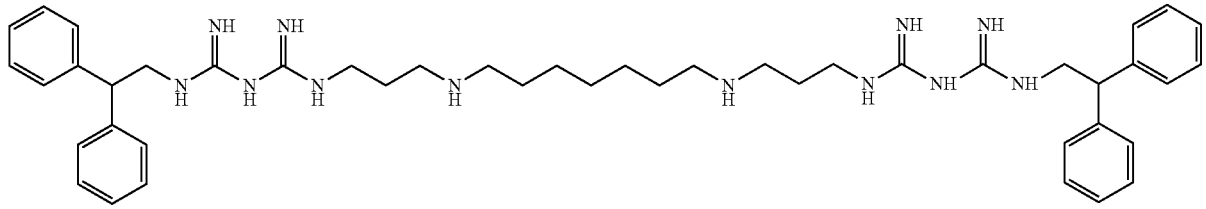

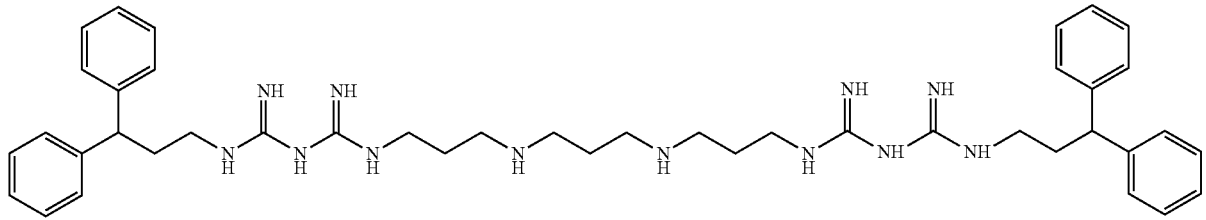

In certain embodiments, the polyamine compound is represented by the structure according to formula (II):

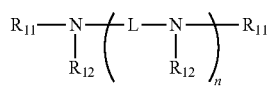

or a salt, solvate or hydrate thereof, where n is 1, 2 or 3;

each L is independently a linker of from about 2 to 14 carbons in length, for example of about 2, 3, 4, 5, 6, 8, 10, 12 or 14 carbon atoms in length, where the linker backbone atoms may be saturated or unsaturated, usually not more than one, two, three, or four unsaturated atoms will be present in a tether backbone, where each of the backbone atoms may be substituted or unsubstituted (for example with a $C_1$-$C_8$ alkyl), where the linker backbone may include a cyclic group (for example, a cyclohex-1,3-diyl group where 3 atoms of the cycle are included in the backbone);

each $R_{12}$ is independently selected from hydrogen and a $C_1$-$C_8$ alkyl; and each $R_{11}$ is independently selected from hydrogen, $C_2$-$C_8$ alkenyl, $C_1$-$C_8$ alkyl or $C_3$-$C_8$ branched alkyl (e.g., methyl, ethyl, tert-butyl, isopropyl, pentyl, cyclobutyl, cyclopropylmethyl, 3-methylbutyl, 2-ethylbutyl, 5-$NH_2$-pent-1-yl, propyl-1-ylmethyl(phenyl)phosphinate, dimethylbicyclo[3.1.1]heptyl)ethyl, 2-(decahydronaphthyl)ethyl and the like), $C_6$-$C_{20}$ aryl or heteroaryl, $C_1$-$C_{24}$aralkyl or heteroaralkyl (2-phenylbenzyl, 4-phenylbenzyl, 2-benzylbenzyl, 3-benzylbenzyl, 3,3-diphenylpropyl, 3-(benzoimidazolyl)-propyl, 4-isopropylbenzyl, 4-fluorobenzyl, 4-tert-butylbenzyl, 3-imidazolyl-propyl, 2-phenylethyl and the like), —C(=O)—$C_1$-$C_8$ alkyl, —C(=O)—$C_1$-$C_8$alkenyl, —C(=O)—$C_1$-$C_8$ alkynyl, an amino-substituted cycloalkyl (e.g., a cycloalkyl group substituted with a primary, secondary, tertiary or quaternary amine, such as 5-$NH_2$-cycloheptyl, 3-$NH_2$-cyclopentyl and the like) and a $C_2$-$C_8$ alkanoyl (e.g., an alkanoyl substituted with a methyl and an alkylazide group).

In certain embodiments, each L is independently selected from: —$CHR_{13}$—$(CH_2)_m$—, —$CHR_{13}$—$(CH_2)_n$—$CHR_{13}$—, —$(CH_2)$—$CHR_{13}$—, —$CH_2$-A-$CH_2$— and —$(CH_2)_p$—
where:
m is an integer from 1 to 5;
A is $(CH_2)_m$, ethane-1,1-diyl or cyclohex-1,3-diyl;
p is an integer from 2 to 14, such as 1, 2, 3, 4 or 5;
n is an integer from 1 to 12; and
$R_{13}$ is a $C_1$-$C_8$alkyl.

A substituted aralkyl or heteroaralkyl with reference to formula (II) intends and includes alkanoyl moieties substituted with an aryl or heteroaryl group, i.e., —C(=O)-aryl, —C(=O)-aralkyl, —C(=O)-heteroaryl, and —C(=O)-heteroaralkyl. In one embodiment, the alkyl portion of the aralkyl or heteroaralkyl moiety is connected to the molecule via its alkyl moiety. For instance at least one or both of $R_{11}$ may be an aralkyl moiety such as 2-phenylbenzyl, 4-phenylbenzyl, 3,3,-diphenylpropyl, 2-(2-phenylethyl)benzyl, 2-methyl-3-phenylbenzyl, 2-napthylethyl, 4-(pyrenyl)butyl, 2-(3-methylnapthyl)ethyl, 2-(1,2-dihydroacenaphth-4-yl)ethyl and the like. In another embodiment, at least one or both of $R_{11}$ may be a heteroaralkyl moiety such as 3-(benzoimidazolyl)propanoyl, 1-(benzoimidazolyl)methanoyl, 2-(benzoimidazolyl)ethanoyl, 2-(benzoimidazolyl)ethyl and the like.

In certain embodiments, the compound of formula (II) comprises at least one moiety selected from the group consisting of t-butyl, isopropyl, 2-ethylbutyl, 1-methylpropyl, 1-methylbutyl, 3-butenyl, isopent-2-enyl, 2-methylpropan-3-olyl, ethylthiyl, phenylthiyl, propynoyl, 1-methyl-1H-pyrrole-2-yl; trifluoromethyl, cyclopropanecarbaldehyde, halo-substituted phenyl, nitro-substituted phenyl, alkyl-substituted phenyl, 2,4,6-trimethylbenzyl, halo-5-substituted phenyl (such as para-($F_3$S)-phenyl, azido and 2-methylbutyl.

In certain embodiments, in formula (II), each $R_{11}$ is independently selected from hydrogen, n-butyl, ethyl, cyclohexylmethyl, cyclopentylmethyl, cyclopropylmethyl, cycloheptylmethyl, cyclohexyleth-2-yl, and benzyl.

In certain embodiments, the polyamine compound is of the structure of formula (II), where n is 3, such that the compound has a structure according to formula (III):

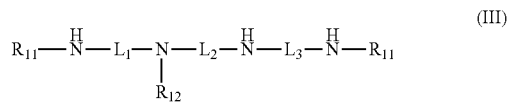

(III)

where $L_1$, $L_2$ and $L_3$ are independently selected from —$CHR_{13}$—$(CH_2)_m$—, —$CHR_{13}$—$(CH_2)_n$—$CHR_{13}$—, —$(CH_2)_m$—$CHR_{13}$—, —$CH_2$-A-$CH_2$— and —$(CH_2)_p$—
where m, A, p, n and $R_{13}$ are as defined above.

In certain embodiments, the polyamine compound is of the structure of Formula (III) where: $L_1$ is —$CHR_{13}$—$(CH_2)_m$—; $L_2$ is —$CHR_{13}$—$(CH_2)_n$—$CHR_{13}$—; and $L_3$ is —$(CH_2)_m$—$CHR_{13}$—; where $R_{11}$, $R_{12}$, $R_{13}$, m and n are as defined above.

In certain embodiments, the polyamine compound is of the structure of Formula (III) where: $L_1$, $L_2$ and $L_3$ are independently —$CH_2$-A-$CH_2$—; and $R_{12}$ is hydrogen; where $R_{11}$ and A are as defined above. In particular embodiments, at least one of an A and an $R_{11}$ comprises an alkenyl moiety.

In certain embodiments, the polyamine compound is of the structure of Formula (III) where: $L_1$, $L_2$ and $L_3$ are independently —$(CH_2)_p$— where p is as defined above; and $R_{12}$ is hydrogen. In particular embodiments, for $L_1$ and $L_3$, p is an integer from 3 to 7, and for $L_3$ p is an integer from 3 to 14.

In certain embodiments, the polyamine compound is of the structure of Formula (III) where: $L_1$, and $L_3$ are independently —$(CH_2)_p$—; $L_2$ is —$CH_2$-A-$CH_2$—; and $R_{12}$ is hydrogen; where $R_{12}$, p and A are as defined above. In particular embodiments, for $L_1$ and $L_3$, p is an integer from 2 to 6, and for $L_3$ A is $(CH_2)^x$ where x is an integer from 1 to 5, or cyclohex-1,3-diyl.

In certain embodiments, the polyamine compound is of the structure of Formula (II), where n is 2, such that the compound has a structure according to formula (IV):

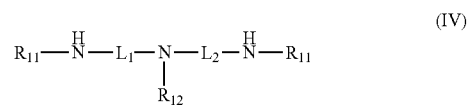

(IV)

where $L_1$ and $L_2$ are independently selected from —$CHR_{13}$—$(CH_2)_m$—$CHR_{13}$—$(CH_2)_n$—$CHR_{13}$—, —$(CH_2)_n$, $CHR_{13}$—, —$CH_2$-A-$CH_2$— and —$(CH_2)_p$—
where m, A, p, n, and $R_{13}$ are as defined above.

In certain embodiments, the polyamine compound is of the structure of Formula (IV) where: $L_1$ is —$(CH_2)_p$—; and $L_2$ is —$(CH_2)_m$—$CHR_{13}$—; where $R_{13}$, m and p are as defined above. In particular embodiments, for $L_1$ p is an integer from 3 to 10, and for $L_2$ n is an integer from 2 to 9.

In certain embodiments, the polyamine compound is of the structure of Formula (IV) where: $L_1$ and $L_2$ are —$(CH_2)_p$—; where p is as defined above. In particular embodiments, p is an integer from 3 to 7.

In certain embodiments, the polyamine compound is of the structure of Formula (II), where n is 1, such that the compound has a structure according to formula (V):

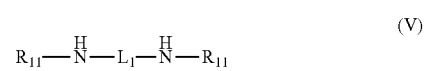

(V)

where $L_1$ is —$(CH_2)_p$— where p is as defined above. In particular embodiments, p is an integer from 2 to 6.

In particular embodiments, in formula (V), one $R_{11}$ is an amino-substituted cycloalkyl (e.g., a cycloalkyl group substituted with a primary, secondary, tertiary or quaternary amine) or a $C_2$-$C_8$ alkanoyl (which alkanoyl may be substituted with one or more substituents such as a methyl or an alkylazide group); and the other $R_{11}$ is a $C_1$-$C_8$ alkyl or a $C_7$-$C_{24}$ aralkyl.

Representative compounds of the formula (II) include, e.g.:

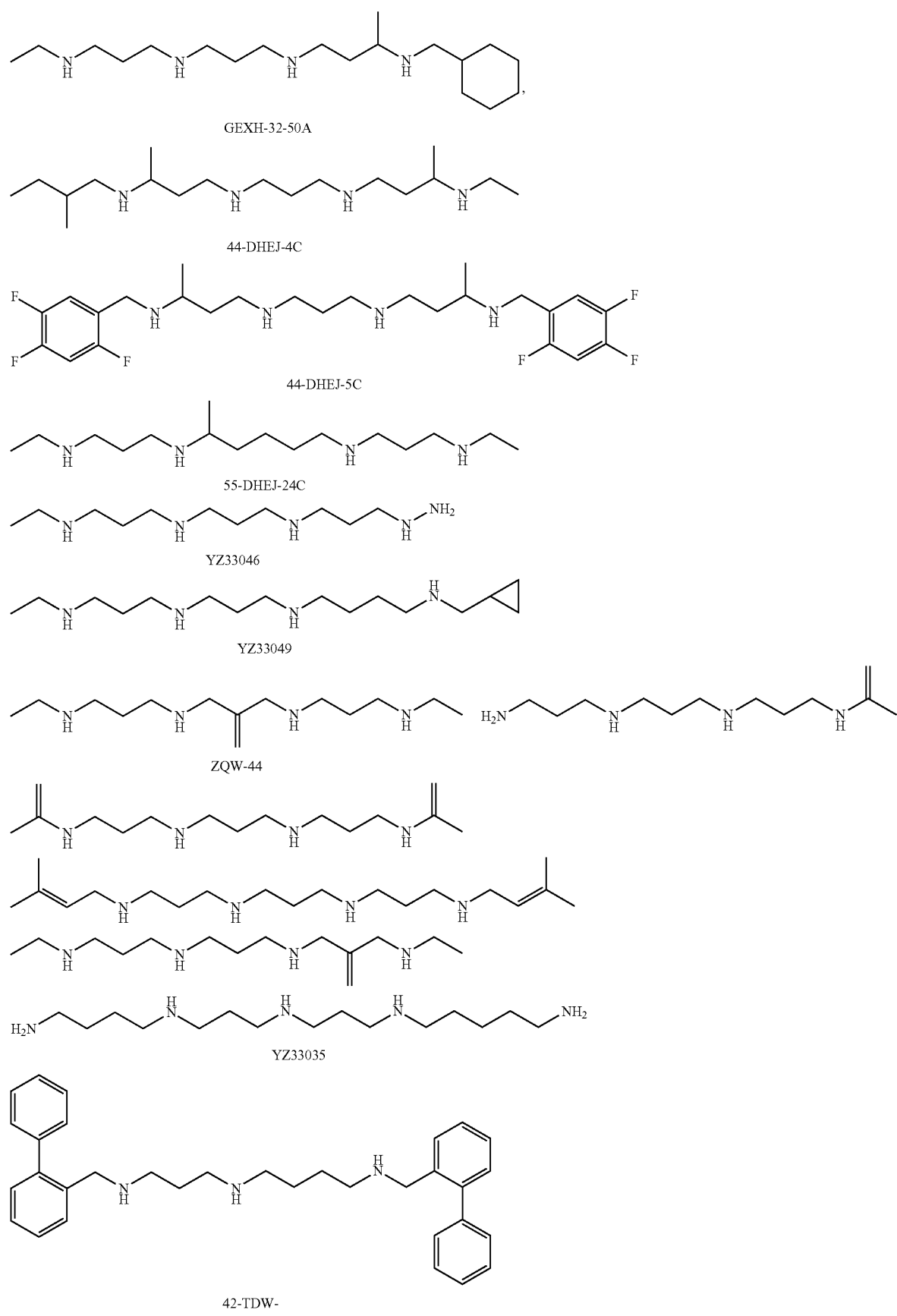

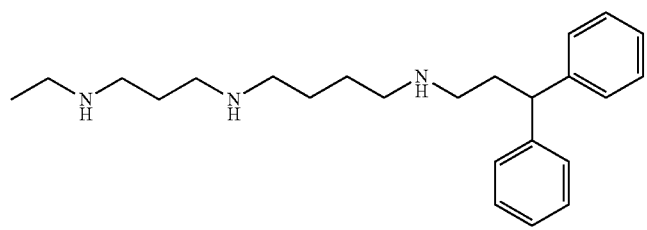
42-TDW-
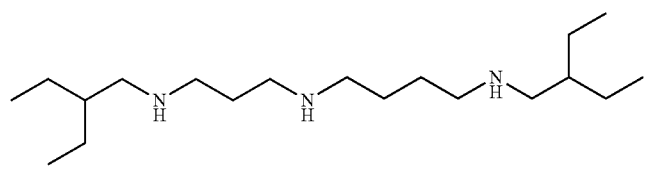
46-TDW-12
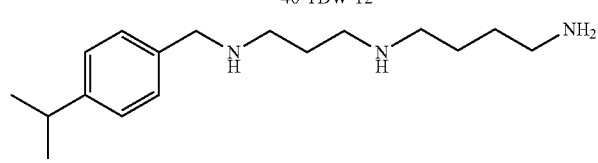
46-TDW-17C
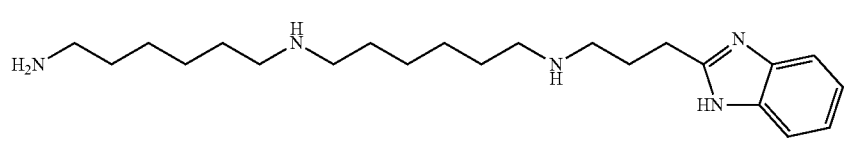
50-DHEJ-3C
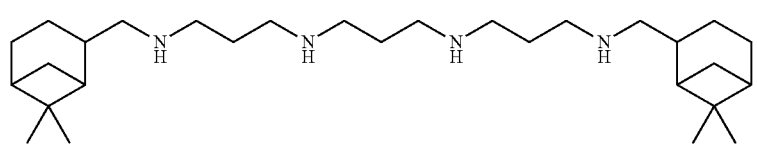
ZQW-35
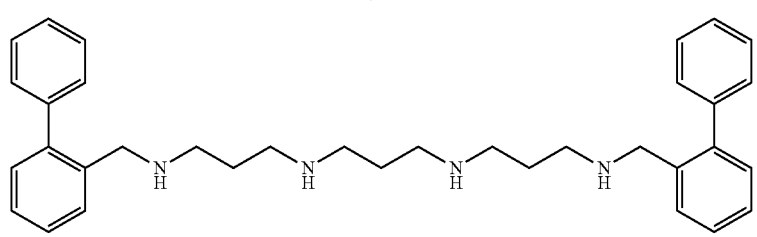
39-TDW-3
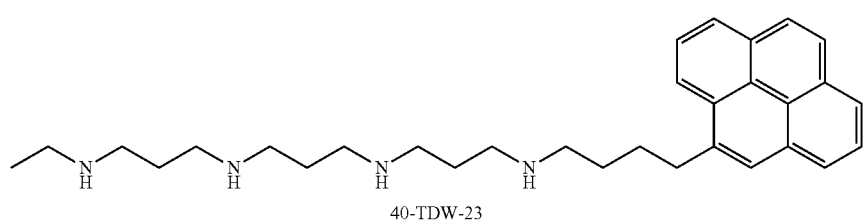
40-TDW-23
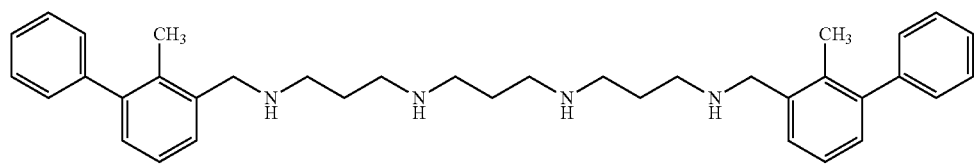
40-TDW-48

-continued
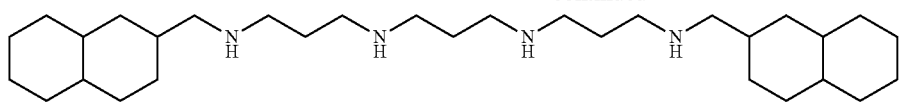
YZ-3312C
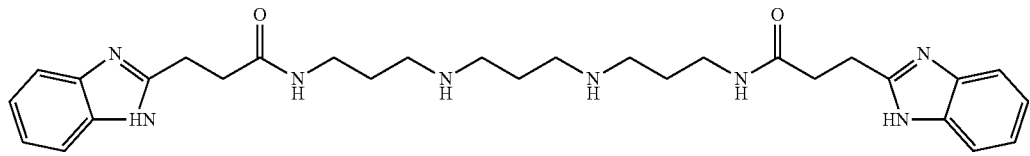
44-DHEJ-38
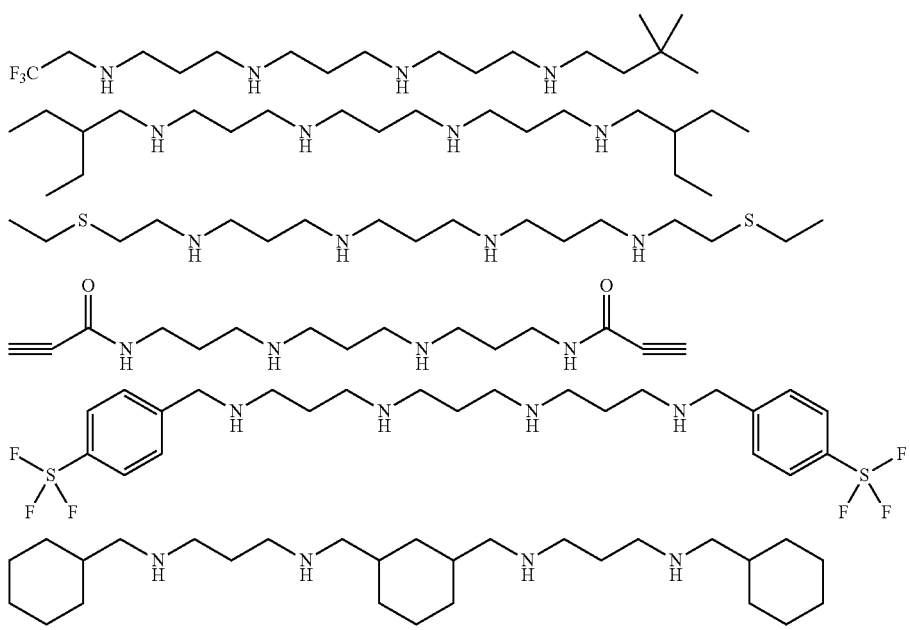
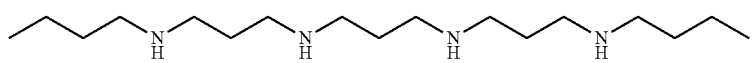
UNS-31-7A
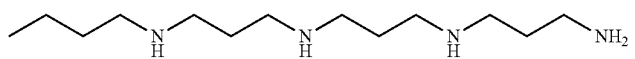
ZQW-14c
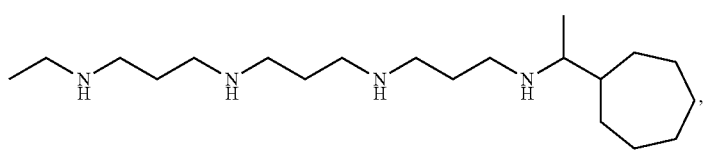
ZQW-16c
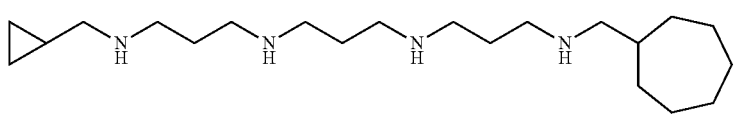
α-methyl CHENspm
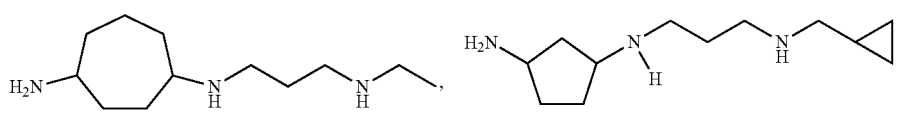
CPCHENspm
UNS-31-18
UNS-31-19c

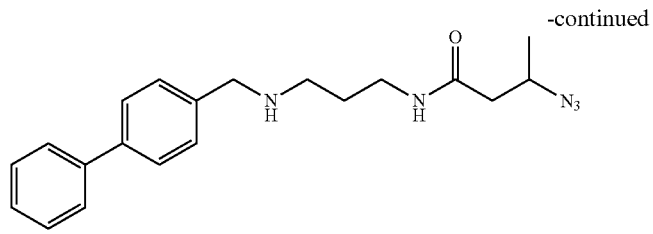

Phenylcyclopropylamine derivatives that are inhibitors of include compounds represented by formula (VI):

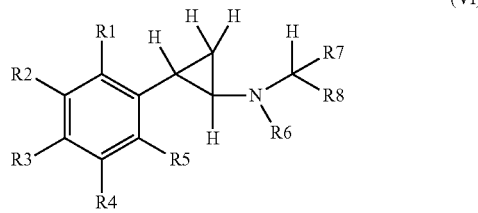

wherein:

each of R1-R5 is independently selected from H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanate, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

R6 is H or alkyl;

R7 is H, alkyl, or cycloalkyl;

R8 is an -L-heterocyclyl wherein the ring or ring system of the -L-heterocyclyl has from 0 to 3 substituents selected from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanate, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido; or R8 is -L-aryl wherein the ring or ring system of the -L-aryl has from 1 to 3 substituents selected from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanate, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

where each L is independently selected from $-(CH_2)_n-$ $(CH_2)_n-$, $-(CH_2)_nNH(CH_2)_n-$, $-(CH_2)_nO(CH_2)_n-$, and $-(CH_2)_nS(CH_2)_n-$, and where each n is independently chosen from 0, 1, 2, and 3;

or a pharmaceutically acceptable salt thereof.

In some cases, L is a covalent bond. In some cases, R6 and R7 are hydro. In some cases, one of R1-R5 is selected from -L-aryl, -L-heterocyclyl, and -L-carbocyclyl.

In some embodiments of the compound of Formula VI, the substituent or substituents on the R8 ring or ring system is/are selected from hydroxyl, halo, alkyl, alkoxy, cycloalkoxy, haloalkyl, haloalkoxy, $-N(C_1-3$ alkyl$)_2$, $-NH(C_1-3$ alkyl$)$, $-C(=O)NH_2$, $-C(=O)NH(C_1-3$ alkyl$)$, $-C(=O)N(C_1-3$ alkyl$)_2$, $-S(=O)_2(C_1-3$ alkyl$)$, $-S(=O)_2NH_2$, $-S(O)_2NH_2$, $-S(O)_2N(C_1-3$ alkyl$)_2$, $-S(=O)_2NH(C_1-3$ alkyl$)$, $-CN$, $-NH_2$, and $-NO_2$.

In certain embodiments, a compound of the invention is of formula (VI) where:

each R1-R5 is optionally substituted and independently chosen from $-H$, halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

R6 is chosen from $-H$ and alkyl;

R7 is chosen from $-H$, alkyl, and cycloalkyl;

R8 is chosen from $-C(=O)NRxRy$ and $-C(=O)Rz$;

Rx when present is chosen from $-H$, alkyl, alkynyl, alkenyl, -L-carbocyclyl, -L-aryl, and -L-heterocyclyl, all of which are optionally substituted (except $-H$);

Ry when present is chosen from $-H$, alkyl, alkynyl, alkenyl, -L-carbocyclyl, -L-aryl, and -L-heterocyclyl, all of which are optionally substituted (except $-H$), where Rx and Ry may be cyclically linked;

Rz when present is chosen from $-H$, alkoxy, -L-carbocyclyl, -L-heterocyclyl, -L-aryl, wherein the aryl, heterocyclyl, or carbocyclyl are optionally substituted; each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of $-(CH_2)_n-(CH_2)_n-$, $-(CH_2)_nC(=O)(CH_2)-$, $-(CH_2)_nC(=O)NH(CH_2)_n-$, $-(CH_2)_nNHC(O)O(CH_2)_n-$, $-(CH_2)_nNHC(=O)NH(CH_2)_n-$, $-(CH_2)_nNHC(=S)S(CH_2)_n-$, $-(CH_2)_nOC(=O)S(CH_2)_n-$, $-(CH_2)_nNH(CH_2)_n-$, $-(CH_2)_n-O-(CH_2)_n-$, $-(CH_2)_nS(CH_2)_n-$, and $-(CH_2)_nNHC(=S)NH(CH_2)_n-$, where each n is independently chosen from 0, 1, 2, 3, 4, 5, 6, 7, and 8. According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, 0-carbamyl, N-carbamyl, 0-thiocarbamyl, N-thiocarbamyl, and C-amido. In a more specific aspect of this embodiment, the optional substituents are 1 or 2 optional substituents chosen from halo, alkyl, aryl, and arylalkyl.

In certain embodiments, in formula (VI), R8 is —CORz, such that the compound is of the following structure:

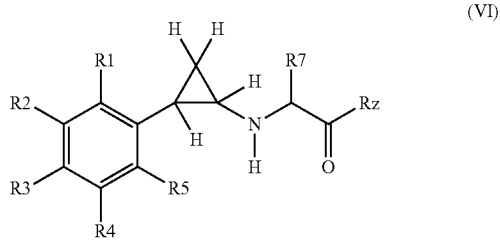

where: R1-R7 are described above; and Rz is -L-heterocyclyl which is optionally substituted with from 1-4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido, and wherein said -L- is independently chosen from —(CH$_2$)$_n$—(CH$_2$)$_n$—, —(CH$_2$)$_n$NH(CH$_2$)$_n$—, —(CH$_2$)$_n$—O—(CH$_2$)$_n$—, and —(CH$_2$)$_n$S(CH$_2$)$_n$—, where each n is independently chosen from 0, 1, 2, and 3.

In a specific aspect of this embodiment, each L is independently chosen from —(CH$_2$)$_n$—(CH$_2$)$_n$— and —(CH$_2$)$_n$—O—(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

Exemplary compounds of Formula VI include:

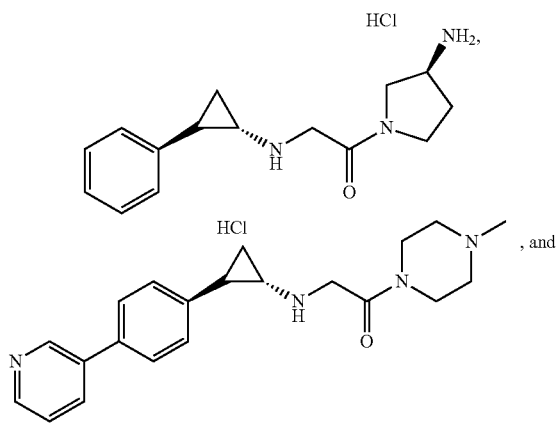

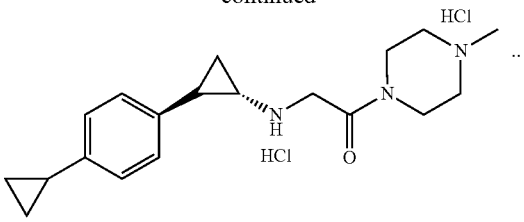

Exemplary compounds of Formula VI include: N-cyclopropyl-2-{[(trans)-2-phenylcyclopropyl]amino}acetamide; 2-{[(trans)-2-phenylcyclopropyl]amino acetamide; N-cyclopropyl-2-{[(trans)-2-phenylcyclopropyl]amino}propanamide; 2-{[(trans)-2-phenylcyclopropyl]amino}-N-prop-2-ynylacetamide; N-isopropyl-2-{[(trans)-2-phenylcyclopropyl]amino}acetamide; N-(tert-butyl)-2-{[(trans)-2-phenylcyclopropyl]amino}acetamide; N-(2-morpholin-4-yl-2-oxoethyl)-N-[(trans)-2-phenylcyclopropyl]amine; 2-{[(trans)-2-phenylcyclopropyl]amino}propanamide; methyl 2-{[(trans)-2-phenylcyclopropyl]amino}propanoate; N-cyclopropyl-2-{methyl[(trans)-2-phenylcyclopropyl]amino}acetamide; 2-{methyl[(trans)-2-phenylcyclopropyl]amino}acetamide; N-methyl-trans-2-(phenylcyclopropylamino)propanamide; 1-(4-methylpiperazin-1-yl)-2-((trans)-2-phenylcyclopropylamino)ethanone; 1-(4-ethylpiperazin-1-yl)-2-((trans)-2-phenylcyclopropylamino)ethanone; 1-(4-benzylpiperazin-1-yl)-2-((trans)-2-phenylcyclopropylamino)-ethanone; 2-((trans)-2-phenylcyclopropylamino)-1-(4-phenylpiperazin-1-yl)ethanone; 2-((trans)-2-(4-(benzyloxy)phenyl)cyclopropylamino)-1-(4-methylpiperazin-1-yl)ethanone; 2-((trans)-2-(4-(benzyloxy)phenyl)cyclopropylamino)-N-cyclopropylacetamide; 2-((trans)-2-(4-(3-fluorobenzyloxy)phenyl)cyclopropylamino)-1-(4--methylpiperazin-1-yl)ethanone; 2-((trans)-2-(4-(3-chlorobenzyloxy)phenyl)cyclopropylamino)-1-(4-methylpiperazin-1-yl)ethanone; 2-((trans)-2-(biphenyl-4-yl)cyclopropylamino)-1-(4-methylpiperazin-1-yl)ethanone; 1-(4-methylpiperazin-1-yl)-2-((trans)-2-(4-phenethoxyphenyl)cyclopropylamino)ethanone; 2-((trans)-2-(4-(4-fluorobenzyloxy)phenyl)cyclopropylamino)-1-(4-methylpiperazin-1-yl)ethanone; 2-((trans)-2-(4-(biphenyl-4-ylmethoxy)phenyl)cyclopropylamino)-1-(4-methylpiperazin-1-yl)ethanone; (trans)-N-(4-fluorobenzyl)-2-phenylcyclopropanamine; (trans)-N-(4-fluorobenzyl)-2-phenylcyclopropanaminium; 4-(((trans)-2-phenylcyclopropylamino)methyl)benzonitrile; (trans)-N-(4-cyanobenzyl)-2-phenylcyclopropanaminium; (trans)-2-phenyl-N-(4-(trifluoromethyl)benzyl)cyclopropanamine; (trans)-2-phenyl-N-(4-(trifluoromethyl)benzyl)cyclopropanaminium; (trans)-2-phenyl-N-(pyridin-2-ylmethyl)cyclopropanamine; (trans)-2-phenyl-N-(pyridin-3-ylmethyl)cyclopropanamine; (trans)-2-phenyl-N-(pyridin-4-ylmethyl)cyclopropanamine; (trans)-N-((6-methylpyridin-2-yl)methyl)-2-phenylcyclopropanamine; (trans)-2-phenyl-N-(thiazol-2-ylmethyl)cyclopropanamine; (trans)-2-phenyl-N-(thiophen-2-ylmethyl)cyclopropanamine; (trans)-N-((3-bromothiophen-2-yl)methyl)-2-phenylcyclopropanamine; (trans)-N-((4-bromothiophen-2-yl)methyl)-2-phenylcyclopropanamine; (trans)-N-(3,4-dichlorobenzyl)-2-phenylcyclopropanamine; (trans)-N-(3-fluorobenzyl)-2-phenylcyclopropanaminium; (trans)-N-(2-fluorobenzyl)-2-phenylcyclopropanamine; (trans)-2-phenyl-N-(quinolin-4-ylmethyl)cyclopropanaraine; (trans)-N-(3-methoxybenzyl)-2-phenylcyclopropanamine; (trans)-2-phenyl-N-((6-(trifluoromethyl)pyridin-3-yl)methyl)cyclopropanamine;

(trans)-N-((6-chloropyridin-3-yl)methyl)-2-phenylcyclopropanamine; (trans)-N-((4-methylpyridin-2-yl)methyl)-2-phenylcyclopropanamine; (trans)-N-((6-methoxypyridin-2-yl)methyl)-2-phenylcyclopropanamine; 2-(((trans)-2-phenylcyclopropylamino)methyl)pyridin-3-ol; (trans)-N-((6-bromopyridin-2-yl)methyl)-2-phenylcyclopropanamine; 4-(((trans)-2-(4(benzyloxy)phenyl)cyclopropylamino)methyl)benzonitrile; (trans)-N-(4-(benzyloxy)benzyl)-2-phenylcyclopropanamine; (trans)-N-benzyl-2-(4-(benzyloxy)phenyl)cyclopropanamine; (trans)-2-(4-(benzyloxy)phenyl)-N-(4-methoxybenzyl)cyclopropanamine; (trans)-2-(4-(benzyloxy)phenyl)-N-(4-fluorobenzyl)cyclopropanamine-; (trans)-2-phenyl-N-(quinolin-2-ylmethyl)cyclopropanamine; (trans)-2-phenyl-N-((5-(trifluoromethyl)pyridin-2-yl)methyl)cyclopropanamine; (trans)-N-((3-fluoropyridin-2-yl)methyl)-2-phenylcyclopropanamine; (trans)-2-phenyl-N-(quinolin-3-ylmethyl)cyclopropanamine; (trans)-N-((6-methoxypyridin-3-yl)methyl)-2-phenylcyclopropanamine; (trans)-N-((5-methoxypyridin-3-yl)methyl)-2-phenylcyclopropanamine-; (trans)-N-((2-methoxypyridin-3-yl)methyl)-2-phenylcyclopropanamine; (trans)-N-((3H-indol-3-yl)methyl)-2-phenylcyclopropanamine; 3-(((trans)-2-phenylcyclopropylamino)methyl)benzonitrile; (trans)-N-(2-methoxybenzyl)-2-phenylcyclopropanamine; 3-(((trans)-2-phenylcyclopropylamino)methyl)pyridin-2-amine; (trans)-N-((2-chloropyridin-3-yl)methyl)-2-phenylcyclopropanamine; (trans)-N-(3,4-dimethoxybenzyl)-2-phenylcyclopropanamine; (trans)-N-((2,3-dihydrobenzofuran-5-yl)methyl)-2-phenylcyclopropanamine; (trans)-N-(benzo[d][1,3]dioxol-5-ylmethyl)-2-phenylcyclopropanamine; (trans)-N-((2,3-dihydrobenzo[b][1,4]dioxin-6-yl)methyl)-2-phenyl-cyclopropanamine; (trans)-N-(2,6-difluoro-4-methoxybenzyl)-2-phenylcyclopropanamine; (trans)-2-phenyl-N-(4-(trifluoromethoxy)benzyl)cyclopropanamine; (trans)-N-(5-fluoro-2-methoxybenzyl)-2-phenylcyclopropanamine; (trans)-N-(2-fluoro-4-methoxybenzyl)-2-phenylcyclopropanamine; (trans)-N-((4-methoxynaphthalen-1-yl)methyl)-2-phenylcyclopropanamine; (trans)-N-(2-fluoro-6-methoxybenzyl)-2-phenylcyclopropanamine; (trans)-N-((2-methoxynaphthalen-1-yl)methyl)-2-phenylcyclopropanamine; (trans)-N-((4,7-dimethoxynaphthalen-1-yl)methyl)-2-phenylcyclopropanamine-; (trans)-N-(4-methoxy-3-methylbenzyl)-2-phenylcyclopropanamine; (trans)-N-(3-chloro-4-methoxybenzyl)-2-phenylcyclopropanamine; (trans)-N-(3-fluoro-4-methoxybenzyl)-2-phenylcyclopropanamine; (trans)-N-(4-methoxy-2-methylbenzyl)-2-phenylcyclopropanamine; (trans)-N-((3,4-dihydro-2H-benzo[b][1,4]dioxepin-6-yl)methyl)-2-phenylcyclopropanamine; (trans)-N-((3,4-dihydro-2H-benzo[b][1,4]dioxepin-7-yl)methyl)-2-phenylcyclopropanamine; (trans)-N-((2,2-dimethylchroman-6-yl)methyl)-2-phenylcyclopropanamine; (trans)-N-(4-methoxy-2,3-dimethylbenzyl)-2-phenylcyclopropanamine; (trans)-N-(4-methoxy-2,5-dimethylbenzyl)-2-phenylcyclopropanamine; (trans)-N-(2-fluoro-4,5-dimethoxybenzyl)-2-phenylcyclopropanamine; (trans)-N-(3-chloro-4,5-dimethoxybenzyl)-2-phenylcyclopropanamine; (trans)-N-(2-chloro-3,4-dimethoxybenzyl)-2-phenylcyclopropanamine; (trans)-N-(2,4-dimethoxy-6-methylbenzyl)-2-phenylcyclopropanamine; (trans)-N-(2,5-dimethoxybenzyl)-2-phenylcyclopropanamine; (trans)-N-(2,3-dimethoxybenzyl)-2-phenylcyclopropanamine; (trans)-N-(2-chloro-3-methoxybenzyl)-2-phenylcyclopropanamine; (trans)-N-((1H-indol-5-yl)methyl)-2-phenylcyclopropanamine; (trans)-2-(4-(benzyloxy)phenyl)-N-(pyridin-2-ylmethyl)cyclopropanamine; (trans)-2-(4-(benzyloxy)phenyl)-N-(2-methoxybenzyl)cyclopropanamine; (trans)-N-(1-(4-methoxyphenyl)ethyl)-2-phenylcyclopropanaraine; (trans)-N-(1-(3,4-dimethoxyphenyl)ethyl)-2-phenylcyclopropanamine; (trans)-N-(1-(2,3-dihydrobenzo[b][1,4]dioxin-6-yl)ethyl)-2-phenylcyclopropanamine; (trans)-N-(1-(5-fluoro-2-methoxyphenyl)ethyl)-2-phenylcyclopropanamine; (trans)-N-(1-(3,4-dimethoxyphenyl)propan-2-yl)-2-phenylcyclopropanamine; (trans)-N-((3-methyl-1,2,4-oxadiazol-5-yl)methyl)-2-phenylcyclopropanamine;

and pharmaceutically acceptable salts thereof.

Alternative small molecule LSD inhibitor compounds may be selected from selective LSD1 and LSD1/MAOB dual inhibitors disclosed for example in WO2010/043721 (PCT/EP2009/063685), WO2010/084160 (PCT/EP2010/050697), PCT/EP2010/055131; PCT/EP2010/055103; and EP application number EP10171345 all of which are explicitly incorporated herein by reference in their entireties to the extent they are not inconsistent with the instant disclosure. Representative compounds of this type include phenylcyclopropylamine derivatives or homologs, illustrative examples of which include phenylcyclopropylamine with one or two substitutions on the amine group; phenylcyclopropylamine with zero, one or two substitutions on the amine group and one, two, three, four, or five substitution on the phenyl group; phenylcyclopropylamine with one, two, three, four, or five substitution on the phenyl group; phenylcyclopropylamine with zero, one or two substitutions on the amine group wherein the phenyl group of PCPA is substituted with (exchanged for) another ring system chosen from aryl or heterocyclyl to give an aryl- or heteroaryl-cyclopropylamine having zero, one or two substituents on the amine group; phenylcyclopropylamine wherein the phenyl group of PCPA is substituted with (exchanged for) another ring system chosen from aryl or heterocyclyl to give an aryl- or heterocyclyl-cyclopropylamine wherein said aryl- or heterocyclyl-cyclopropylamine on said aryl or heterocyclyl moiety has zero, one or two substitutions on the amine group and one, two, three, four, or five substitution on the phenyl group; phenylcyclopropylamine with one, two, three, four, or five substitution on the phenyl group; or any of the above described phenylcyclopropylamine analogs or derivatives wherein the cyclopropyl has one, two, three or four additional substituents. Suitably, the heterocyclyl group described above in this paragraph is a heteroaryl.

Non-limiting embodiments of phenylcyclopropylamine derivatives or analogs include "cyclopropylamine amide" derivatives and "cyclopropylamine" derivatives. Specific examples of "cyclopropylamine acetamide" derivatives include, but are not limited to: N-cyclopropyl-2-{[(trans)-2-phenylcyclopropyl]amino}acetamide; 2-{[(trans)-2-phenylcyclopropyl]amino}acetamide; N-cyclopropyl-2-{[(trans)-2-phenylcyclopropyl]amino}propanamide; 2-{[(trans)-2-phenylcyclopropyl]amino}-N-prop-2-ynylacetamide; N-isopropyl-2-{[(trans)-2-phenylcyclopropyl]amino}acetamide; N-(tert-butyl)-2-{[(trans)-2-phenylcyclopropyl]amino}acetamide; N-(2-morpholin-4-yl-2-oxoethyl)-N-[(trans)-2-phenylcyclopropyl]amine; 2-{[(trans)-2-phenylcyclopropyl]amino}propanamide; Methyl 2-{[(trans)-2-phenylcyclopropyl]amino}propanoate; 1-(4-methylpiperazin-1-yl)-2-((trans)-2-phenylcyclopropylamino)ethanone; 1-(4-ethylpiperazin-1-yl)-2-((trans)-2-phenylcyclopropylamino)ethanone; 1-(4-benzylpiperazin-1-yl)-2-((trans)-2-phenylcyclopropylamino)ethanone; 2-((trans)-2-phenylcyclopropylamino)-1-(4-phenylpiperazin-1-yl)

ethanone; 2-((trans)-2-(4-(benzyloxy)phenyl)cyclopropylamino)-1-(4-methylpiperazin-1-yl)ethanone; 2-((trans)-2-(1,1'-biphenyl-4-yl)cyclopropylamino)-1-(4-methylpiperazin-1-yl)ethanone; 2-((trans)-2-(4-(benzyloxy)phenyl)cyclopropylamino)-N-cyclopropylacetamide; 2-((trans)-2-(4-(3-fluorobenzyloxy)phenyl)cyclopropylamino)-1-(4--methylpiperazin-1-yl)ethanone; 2-((trans)-2-(4-(4-fluorobenzyloxy)phenyl)cyclopropylamino)-1-(4-methylpiperazin-1-yl)ethanone; 2-((trans)-2-(4-(3-chlorobenzyloxy)phenyl)cyclopropylamino)-1-(4-methylpiperazin-1-yl)ethanone; 1-(4-methylpiperazin-1-yl)-2-((trans)-2-(4-phenethoxyphenyl)cyclopropylamino)ethanone; 2-((trans)-2-(biphenyl-4-yl)cyclopropylamino)-1-(4-methylpiperazin-1-yl)ethanone; N-cyclopropyl-2-{[(trans)-2-phenylcyclopropyl]amino}acetamide; N-methyl-trans-2-(Phenylcyclopropylamino)propanamide; 2-{methyl[(trans)-2-phenylcyclopropyl]amino}acetamide; N-[2-(4-methylpiperazin-1-yl)ethyl]-N-[(trans)-2-phenylcyclopropyl]amine; N-cyclopropyl-N'-[(trans)-2-phenylcyclopropyl]ethane-1,2-diamine; N,N-dimethyl-N'-(2-{[(trans)-2-phenylcyclopropyl]amino}ethyl)ethane-1,2-diamine; (3R)-1-(2-{[(trans)-2-phenylcyclopropyl]amino}ethyl)pyrrolidin-3-amine; (3S)—N,N-dimethyl-1-(2-{[(trans)-2-phenylcyclopropyl]amino}ethyl)pyrrolidin-3-amine; (3R)—N,N-dimethyl-1-(2-{[(trans)-2-phenylcyclopropyl]amino}ethyl)pyrrolidin-3-amine; N-[(trans)-2-phenylcyclopropyl]-N-(2-piperazin-1-ylethyl)amine; N,N-diethyl-N'-[(trans)-2-phenylcyclopropyl]ethane-1,2-diamine; N-[(trans)-2-phenylcyclopropyl]-N-(2-piperidin-1-ylethyl)amine; (trans)-2-(4-(benzyloxy)phenyl)-N-(2-(4-methylpiperazin-1-yl)ethyl)cyclopropanamine; (trans)-N-(2-(4-methylpiperazin-1-yl)ethyl)-2-(3'-(trifluoromethyl)biphenyl-4-yl)cyclopropanamine; (trans)-2-(3'-chlorobiphenyl-4-yl)-N-(2-(4-methylpiperazin-1-yl)ethyl)cyclopropanamine; (R)-1-(2-((trans)-2-(3'-(trifluoromethyl)biphenyl-4-yl)cyclopropylamino)ethyl)pyrrolidin-3-amine; and $N^1$-cyclopropyl-$N^2$-((trans)-2-(3'-(trifluoromethyl)biphenyl-4-yl-)cyclopropyl)ethane-1,2-diamine.

Specific examples of "cyclopropylamine" derivatives, include, but are not limited to: N-4-fluorobenzyl-N-{(trans)-2-[4-(benzyloxy)phenyl]cyclopropyl}amine, N-4-methoxybenzyl-N-{(trans)-2-[4-(benzyloxy)phenyl]cyclopropyl}amine, N-benzyl-N-{(trans)-2-[4-(benzyloxy)phenyl]cyclopropyl}amine, N-[(trans)-2-phenylcyclopropyl]amino-methyl)pyridin-3-ol, N-[(trans)-2-phenylcyclopropyl]-N-(3-methylpyridin-2-ylmethyl)amine, N-[(trans)-2-phenylcyclopropyl]-N-(4-chloropyridin-3-ylmethyl)amine, N-[(trans)-2-phenylcyclopropyl]-N-(4-trifluoromethylpyridin-3-yl-methyl)amine, N-(3-methoxybenzyl)-N-[(trans)-2-phenylcyclopropyl]amine, N-[(trans)-2-phenylcyclopropyl]-N-(quinolin-4-ylmethyl)amine, N-(2-fluorobenzyl)-N-[(trans)-2-phenylcyclopropyl]amine, N-(3-fluorobenzyl)-N-[(trans)-2-phenylcyclopropyl]amine, N-[(trans)-2-phenylcyclopropyl]-N-(3,4-dichloro-1-phenyl-methyl)amine, N-[(trans)-2-phenylcyclopropyl]-N-(5-bromo-thiophen-2-ylmethyl)amine, N-[(trans)-2-phenylcyclopropyl]-N-(3-bromo-thiophen-2-ylmethyl)-amine, N-[(trans)-2-phenylcyclopropyl]-N-(thiophen-2-ylmethyl)amine, N-[(trans)-2-phenylcyclopropyl]-N-(1,3-thiazol-2-ylmethyl)amine, N-[(trans)-2-phenylcyclopropyl]-N-(3-methyl-pyridin-2-ylmethyl)amine, N-[(trans)-2-phenylcyclopropyl]-N-(pyridin-4-ylmethyl)amine, N-[(trans)-2-phenylcyclopropyl]-N-(pyridin-3-ylmethyl)amine, N-[(trans)-2-phenylcyclopropyl]-N-(pyridin-2-ylmethyl)amine, [(trans)-2-phenylcyclopropyl]-N-[4-(trifluoromethyl)benzyl]amine, ({[(trans)-2-phenylcyclopropyl]amino}methyl)benzonitrile, N-(4-fluorobenzyl)-N-[(trans)-2-phenylcyclopropyl]amine, N-[(trans)-2-phenylcyclopropyl]-N-(3-bromo-pyridin-2-ylmethyl)amine, N-4-cyanobenzyl-N-{(trans)-2-[4-(benzyloxy)phenyl]cyclopropyl}amine, N-4-[(benzyloxy)-benzyl]-N-[(trans)-2-(4-phenyl)cyclopropyl]amine; 2-((trans)-2-(4-(4-cyanobenzyloxy)phenyl)cyclopropylamino)acetamide, 2-((trans)-2-(4-(3-cyanobenzyloxy)phenyl)cyclopropylamino)acetamide, 2-((trans)-2-(4-(benzyloxy)phenyl)cyclopropylamino)acetamide, 2-((trans)-2-(4-(4-fluorobenzyloxy)phenyl)cyclopropylamino)acetamide, 2-((trans)-2-(4-(3-fluorobenzyloxy)phenyl)cyclopropylamino)acetamide, 2-((trans)-2-(4-(3-chlorobenzyloxy)phenyl)cyclopropylamino)acetamide, 2-((trans)-2-(4-(4-chlorobenzyloxy)phenyl)cyclopropylamino)acetamide, 2-((trans)-2-(4-(3-bromobenzyloxy)phenyl)cyclopropylamino)acetamide, 2-((trans)-2-(4-(3,5-difluorobenzyloxy)phenyl)cyclopropylamino)acetamide, 2-((trans)-2-(4-phenethoxyphenyl)cyclopropylamino)acetamide, 2-((trans)-2-(3'-(trifluoromethyl)biphenyl-4-yl)cyclopropylamino)acetamide, and 2-((trans)-2-(3'-chlorobiphenyl-4-yl)cyclopropylamino)acetamide.

Other examples of LSD1 inhibitors are, e.g., phenelzine or pargyline (propargylamine) or a derivative or analog thereof. Derivatives and analogs of phenelzine and pargyline (propargylamine) include, but are not limited to, compounds where the phenyl group of the parent compound is replaced with a heteroaryl or optionally substituted cyclic group or the phenyl group of the parent compound is optionally substituted with a cyclic group. In one aspect, the phenelzine or pargyline derivative or analog thereof has selective LSD1 or dual LSD1/MAOB inhibitory activity as described herein. In some embodiments, the phenelzine derivative or analog has one, two, three, four or five substituents on the phenyl group. In one aspect, the phenelzine derivative or analog has the phenyl group substituted with (exchanged for) an aryl or heterocyclyl group wherein said aryl or heterocyclyl group has zero, one, two, three, four or five substituents. In one aspect, the pargyline derivative or analog has one, two, three, four or five substituents on the phenyl group. In one aspect, the pargyline derivative or analog has the phenyl group substituted with (exchanged for) an aryl or heterocyclyl group wherein said aryl or heterocyclyl group has zero, one, two, three, four or five substituents. Methods of preparing such compounds are known to the skilled artisan.

The present invention also contemplates tranylcypromine derivatives as described for example by Binda et al. (2010. J. Am. Chem. Soc. 132:6827-6833, which is hereby incorporated by reference herein in its entirety) as inhibitors of LSD (e.g., LSD1 and/or LSD2) enzymatic function. Non-limiting example of such compounds include:

13a

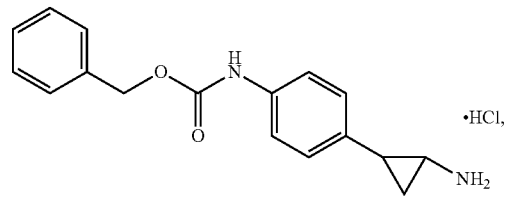

-continued

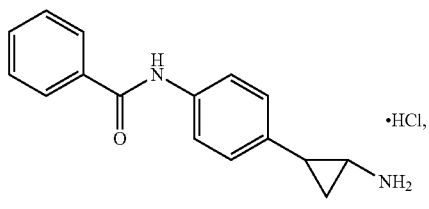

13b

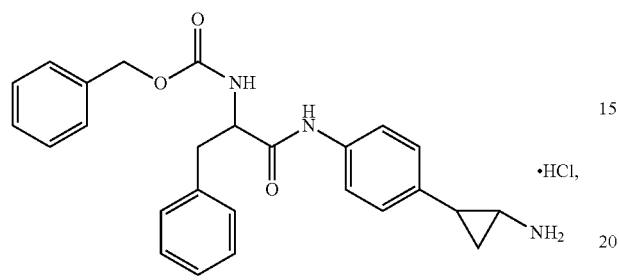

14e

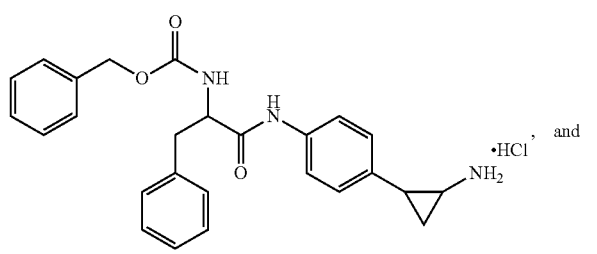

15

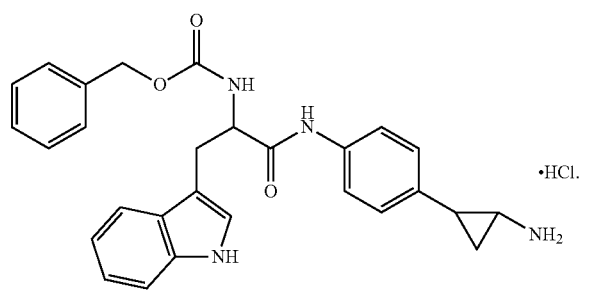

14l

Alternatively, LSD1 inhibitor compounds may be selected from tranylcypromine analogs described by Benelkebir et al. (2011. *Bioorg. Med. Chem.* doi:10.1016/j.bmc.2011.02.017, which is hereby incorporated by reference herein in its entirety), Representative analogs of this type, including o-, m- and p-bromo analogues include: (1R,2S)-2-(4-bromophenyl)cyclopropanamine hydrochloride (Compound 4c), (1R,2S)-2-(3-bromophenyl)cyclopropanamine hydrochloride (Compound 4d), (1R,2S)-2-(2-bromophenyl)cyclopropanamine hydrochloride (Compound 4e), (1R,2S)-2-(biphenyl-4-yl)cyclopropanamine hydrochloride (Compound 4f).

Reference also may be made to peptide scaffold compounds disclosed by Culhane et al. (2010. *J. Am. Chem. Soc.* 132:3164-3176, which is hereby incorporated by reference herein in its entirety), which include chlorovinyl, endocyclopropylamine, and hydrazine functionalities. Non-limiting compounds disclosed by Culhane et al. include propargyl-Lys-4, N-methylpropargyl-Lys-4 H3-21, cis-3-chloroallyl-Lys-4 H3-21, trans-3-chloroallyl-Lys-4 H3-21, exo-cyclopropyl-Lys-4 H3-21, endo-cyclopropyl-Lys-4 H3-21, endo-dimethylcyclopropyl-Lys-4, hydrazino-Lys-4 H3-21 and hydrazino-Lys-4 H3-21.

Alternative cyclopropylamine compounds that are useful for inhibiting LSD1 include those disclosed by Fyfe et al. in U.S. Publication No. 2013/0197013, which is incorporated herein by reference in its entirety. Illustrative cyclopropylamine inhibitors of LSD1, which are disclosed as being selective for inhibiting LSD1, include compounds according to formula VII:

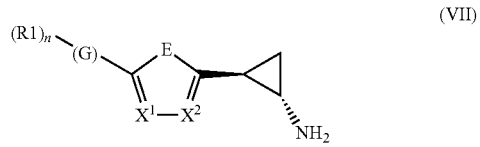

(VII)

wherein:

E is —N(R3)-, —O—, or —S—, or is —X$^3$=X$^4$—;

X$^1$ and X$^2$ are independently C(R2) or N;

X$^3$ and X$^4$, when present, are independently C(R2) or N;

(G) is a cyclyl group (as shown in formula VII, the cyclyl group (G) has n substituents (R1));

each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;

R3 is —H or a (C$_1$-C$_6$)alkyl group;

each L1 is independently alkylene or heteroalkylene; and n is 0, 1, 2, 3, 4 or 5, or an enantiomer, a diastereomer, or a mixture thereof, or a pharmaceutically acceptable salt or solvate thereof.

In some embodiments, compounds of formula VII are represented by formula VIII:

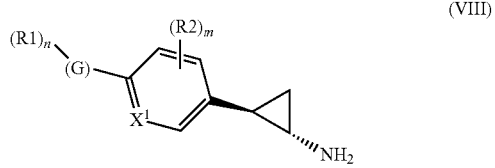

(VIII)

wherein:

X$^1$ is CH or N; (G) is a cyclyl group;

each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;

each L1 is independently alkylene or heteroalkylene;

m is 0, 1, 2 or 3; and n is 0, 1, 2, 3, 4 or 5, provided that n and m are chosen independently such that n+m is greater than zero when $X^1$ is —CH— and (G) is an aryl, or an enantiomer, a diastereomer, or a mixture thereof, or a pharmaceutically acceptable salt or solvate thereof.

In other embodiments, compounds of formula VII are represented by formula IX:

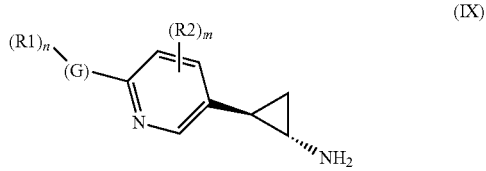

(IX)

wherein:

(G) is a cyclyl group;

each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 0, 1, 2, or 3 optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;

each L1 is independently alkylene or heteroalkylene; m is 0, 1, 2 or 3; and n is 0, 1, 2, 3, 4 or 5, or an enantiomer, a diastereomer, or a mixture thereof, or a pharmaceutically acceptable salt or solvate thereof.

In still other embodiments, compounds of formula VII are represented by formula X:

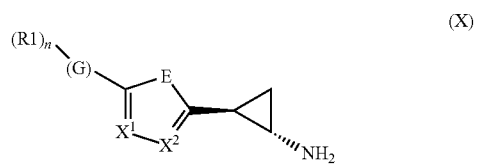

(X)

wherein:

E is —N(R3)-, —O—, or —S—, or is —$X^3$=$X^4$—;

$X^1$, $X^2$, $X^3$ and $X^4$ are independently C(R2) or N, provided that at least one of $X^1$, $X^2$, $X^3$ and $X^4$ is N when E is —$X^3$=$X^4$—;

(G) is a cyclyl group; each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;

R3 is —H or a ($C_1$-$C_6$)alkyl group; each L1 is alkylene or heteroalkylene; and n is 0, 1, 2, 3, 4 or 5, or an enantiomer, a diastereomer, or a mixture thereof, or a pharmaceutically acceptable salt or solvate thereof.

In still other embodiments, compounds of formula VII are represented by formula XI:

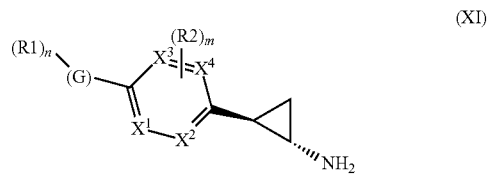

(XI)

wherein:

$X^1$, $X^2$, $X^3$ and $X^4$ are independently CH or N, provided that at least one of $X^1$, $X^2$, $X^3$ and $X^4$ is N;

(G) is a cyclyl group; each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate; each L1 is alkylene or heteroalkylene;

m is 0, 1, 2 or 3; and n is 0, 1, 2, 3, 4 or 5, or an enantiomer, a diastereomer, or a mixture thereof, or a pharmaceutically acceptable salt or solvate thereof.

Representative compounds according to formula VII are suitably selected from: (trans)-2-(3'-(trifluoromethyl)biphenyl-4-yl)cyclopropanamine; (trans)-2-(terphenyl-4-yl)cyclopropanamine; 4'-((trans)-2-aminocyclopropyl)biphenyl-4-ol; 4'-((trans)-2-aminocyclopropyl)biphenyl-3-ol; (trans)-2-(6-(3-(trifluoromethyl)phenyl)pyridin-3-yl)cyclopropanamine; (Trans)-2-(6-(3,5-dichlorophenyl)pyridin-3-yl)cyclopropanamine; (trans)-2-(6-(4-chlorophenyl)pyridin-3-yl)cyclopropanamine; (trans)-2-(6-(3-chlorophenyl)pyridin-3-yl)cyclopropanamine; (trans)-2-(6-(4-(trifluoromethyl)phenyl)pyridin-3-yl)cyclopropanamine; (trans)-2-(6-(4-methoxyphenyl)pyridin-3-yl)cyclopropanamine; (trans)-2-(6-(3-methoxyphenyl)pyridin-3-yl)cyclopropanamine; 4-(5-((trans)-2-aminocyclopropyl)pyridin-2-yl)benzonitrile; 3-(5-((trans)-2-aminocyclopropyl)pyridin-2-yl)benzonitrile; (Trans)-2-(6-p-tolylpyridin-3-yl)cyclopropanamine; (Trans)-2-(6-m-tolylpyridin-3-yl)cyclopropanamine; 4-(5-((trans)-2-aminocyclopropyl)pyridin-2-yl)phenol; 3-(5-((trans)-2-aminocyclopropyl)pyridin-2-yl)phenol; 4-(5-((trans)-2-aminocyclopropyl)pyridin-2-yl)benzamide; 3-(5-((trans)-2-aminocyclopropyl)pyridin-2-yl)benzamide; 2-(5-((trans)-2-aminocyclopropyl)pyridin-2-yl)phenol; 3-(5-((trans)-2-aminocyclopropyl)pyridin-2-yl)phenol; (Trans)-2-(6-(3-methoxy-4-methylphenyl)pyridin-3-yl)cyclopropanamine; 5-(5-((trans)-2-aminocyclopropyl)pyridin-2-yl)-2-fluorophenol; 3-(5-((trans)-2-aminocyclopropyl)pyridin-2-yl)-5-fluorophenol; 3-(5-((trans)-2-aminocyclopropyl)pyridin-2-yl)-4-fluorophenol; 3-(5-((trans)-2-aminocyclopropyl)pyridin-2-yl)-2-fluorophenol; 3-(5-((trans)-2-aminocyclopropyl)pyridin-2-yl)-2,4-difluorophenol; 3-(5-((trans)-2-aminocyclopropyl)pyridin-2-yl)-2,4,6-trifluorophenol; 3-(5-((trans)-2-aminocyclopropyl)pyridin-2-yl)-5-chlorophenol; (Trans)-2-(6-(2-fluoro-3-(trifluoromethyl)phenyl)pyridin-3-yl)cyclopropanamine; (Trans)-2-(6-(5-chlorothiophen-2-yl)pyridin-3-yl)cyclopropanamine; (Trans)-2-(6-(5-methylthiophen-2-yl)pyridin-3-yl)cyclopropanamine; (Trans)-2-(6-(1H-indol-6-yl)pyridin-3-yl)cyclopropanamine; (Trans)-2-(6-(benzo[b]thiophen-5-yl)pyridin-3-yl)cyclopropanamine; 3-(5-((trans)-2-aminocyclopropyl)-3-methylpyridin-2-yl)phenol; (trans)-2-(6-(3-chlorophenyl)-5-methylpyridin-3-yl)cyclopropanamine; (trans)-2-(5-methyl-6-(3-(trifluoromethyl)phenyl)pyridin-3-yl)cyclopropanamine; (trans)-2-(6-(4-fluoro-3-methoxyphenyl)pyridin-3-yl)cyclopropanamine, (trans)-2-(6-(3-fluoro-5-methoxyphenyl)pyridin-3-yl)cyclopropanamine; (trans)-2-(6-(2-fluoro-5-methoxyphenyl)pyridin-3-yl)cyclopropanamine, (trans)-2-(6-(2-fluoro-3-methoxyphenyl)pyridin-3-yl)cyclopropanamine; (trans)-2-(6-(3-chloro-5-methoxyphenyl)pyridin-3-yl)cyclopropanamine; (trans)-2-(6-(2-chloro-5-methoxyphenyl)pyridin-3-yl)cyclopropanamine; (trans)-2-(6-(3-methoxy-5-(trifluoromethyl)phenyl)pyridin-3-yl)cyclopropanamine; 3-(5-((trans)-2-aminocyclopropyl)pyridin-2-yl)-5-methoxybenzonitrile; 5-(5-((trans)-2-aminocyclopropyl)pyridin-2-yl)-2-methylphenol; 3-(5-((trans)-2-aminocyclopropyl)pyridin-2-yl)-4-chlorophenol; 3-(5-((trans)-2-aminocyclopropyl)pyridin-2-yl)-5-(trifluoromethyl)phenol; (trans)-2-(6-(2-fluoro-5-(trifluoromethyl)phenyl)pyridin-3-yl)cyclopropanamine; (trans)-2-(6-(2-chloro-5-(trifluoromethyl)phenyl)pyridin-3-yl)cyclopropanamine; (trans)-2-(6-(3,5-bis(trifluoromethyl)phenyl)pyridin-3-yl)cyclopropanamine; N-(3-(5-((trans)-2-aminocyclopropyl)pyridin-2-yl)phenyl)acetamide; N-(3-(5-((trans)-2-aminocyclopropyl)pyridin-2-yl)phenyl)methanesulfonamide; (trans)-2-(6-(benzo[b]thiophen-2-yl)pyridin-3-yl)cyclopropanamine; (trans)-2-(6-(benzo[b]thiophen-3-yl)pyridin-3-yl)cyclopropanamine; 5-(5-((trans)-2-aminocyclopropyl)pyridin-2-yl)thiophene-2-carbonitrile; (trans)-2-(6-(4-methylthiophen-3-yl)pyridin-3-yl)cyclopropanamine; (trans)-2-(2-chloro-6-(3-(trifluoromethyl)phenyl)pyridin-3-yl)cyclopropanamine; (trans)-2-(2-(4-chlorophenyl)-6-(3-(trifluoromethyl)phenyl)pyridine-3-yl)cyclopropanamine; 4-(3-((trans)-2-aminocyclopropyl)-6-(3-(trifluoromethyl)phenyl)pyridin-2-yl)phenol; 4-(3-((trans)-2-aminocyclopropyl)-6-(3-(trifluoromethyl)phenyl)-pyridin-2-yl)benzamide; (trans)-2-(2-methyl-6-(3-(trifluoromethyl)phenyl)pyridin-3-yl)cyclopropanamine; 3-(5-((trans)-2-aminocyclopropyl)pyridin-2-yl)-5-hydroxybenzonitrile; (trans)-2-(6-(3,4-difluoro-5-methoxyphenyl)pyridin-3-yl)cyclopropanamine; 5-(5-((trans)-2-aminocyclopropyl)pyridin-2-yl)-2,3-difluorophenol; (trans)-2-(6-(3-chloro-4-fluoro-5-methoxyphenyl)pyridin-3-yl)cyclopropanamine; 5-(5-((trans)-2-aminocyclopropyl)pyridin-2-yl)-3-chloro-2-fluorophenol; (trans)-2-(6-(1H-indazol-6-yl)pyridin-3-yl)cyclopropanamine; (trans)-2-(6-(9H-carbazol-2-yl)pyridin-3-yl)cyclopropanamine; 6-(5-((trans)-2-aminocyclopropyl)pyridin-2-yl)indolin-2-one; 6-(5-((trans)-2-aminocyclopropyl)pyridin-2-yl)benzofuran-2(3H)-one; 4-(5-((trans)-2-aminocyclopropyl)pyridin-2-yl)pyridin-2(1H)-one; N-(3-(5-((trans)-2-aminocyclopropyl)pyridin-2-yl)phenyl)benzenesulfonamide; N-(3-(5-((trans)-2-aminocyclopropyl)pyridin-2-yl)phenyl)propane-2-sulfonamide; 4'-((trans)-2-aminocyclopropyl)-4-fluorobiphenyl-3-ol; 4'-((trans)-2-aminocyclopropyl)-5-chlorobiphenyl-3-ol; 4'-((trans)-2-aminocyclopropyl)-5-chloro-4-fluorobiphenyl-3-ol; N-(4'-((trans)-2-aminocyclopropyl)biphenyl-3-yl)benzenesulfonamide; N-(4'-((trans)-2-aminocyclopropyl)biphenyl-3-yl)propane-2-sulfonamide; N-(4'-((trans)-2-aminocyclopropyl)biphenyl-3-yl)methanesulfonamide; N-(2-(5-((trans)-2-aminocyclopropyl)pyridin-2-yl)phenyl)methanesulfonamide; 3-(5-((trans)-2-aminocyclopropyl)pyridin-2-yl)-4-methoxybenzonitrile; N-(4'-((trans)-2-aminocyclopropyl)biphenyl-2-yl)methanesulfonamide; 4'-((trans)-2-aminocyclopropyl)-6-methoxybiphenyl-3-carbonitrile; N-(4'-((trans)-2-aminocyclopropyl)-6-methoxybiphenyl-3-yl)methanesulfonamide; 4'-((trans)-2-aminocyclopropyl)-6-hydroxybiphenyl-3-carbonitrile; N-(4'-((trans)-2-aminocyclopropyl)-6-hydroxybiphenyl-3-yl)methanesulfonamide; 3-(5-((trans)-2-aminocyclopropyl)pyridin-2-yl)-4-hydroxybenzonitrile; N-(3-(5-((trans)-2-aminocyclopropyl)pyridin-2-yl)-4-hydroxyphenyl)methane-sulfonamide; N-(3-(5-((trans)-2-aminocyclopropyl)pyridin-2-yl)-5-(trifluoromethyl)phenyl)ethanesulfonamide; N-(3-(5-((trans)-2-aminocyclopropyl)pyridin-2-yl)-5-(trifluoromethyl)phenyl)methanesulfonamide; 3-(6-((trans)-2-aminocyclopropyl)pyridin-3-yl)phenol; (Trans)-2-(5-(3-methoxyphenyl)pyridin-2-yl)cyclopropanamine; 4-(6-((trans)-2-aminocyclopropyl)pyridin-3-yl)phenol; 2-(6-((trans)-2-aminocyclopropyl)pyridin-3-yl)phenol; 2-(5-((trans)-2-aminocyclopropyl)thiophen-2-yl)phenol; 3-(5-((trans)-2-aminocyclopropyl)thiophen-2-yl)phenol; 4-(5-((trans)-2-aminocyclopropyl)thiophen-2-yl)phenol; 2-(5-((trans)-2-aminocyclopropyl)thiazol-2-yl)phenol; 3-(5-((trans)-2-aminocyclopropyl)thiazol-2-yl)phenol; 4-(5-((trans)-2- aminocyclopropyl)thiazol-2-yl)phenol; 2-(2-((trans)-2-aminocyclopropyl)thiazol-5-yl)phenol; 3-(2-((trans)-2-aminocyclopropyl)thiazol-5-yl)phenol; 2-(2-((trans)-2-aminocyclopropyl)thiazol-5-yl)phenol; 3-(2-((trans)-2-aminocyclopropyl)thiazol-5-yl)phenol; 3-(5-((trans)-2-aminocyclopropyl)pyrimidin-2-yl)phenol; 4-(5-((trans)-2-aminocyclopropyl)pyrimidin-2-yl)phenol; N-(3-(5-((trans)-2-aminocyclopropyl)pyridin-2-yl)-4-methoxyphenyl)methane-sulfonamide; N-(4'-((trans)-2-aminocyclopropyl)-5-chloro-[1,1'-biphenyl]-3-yl)methanesulfonamide; N-(3-(5-((trans)-2-aminocyclopropyl)pyridin-2-yl)-5-chlorophenyl)methanesulfonamide; N-(4'-((trans)-2-aminocyclopropyl)-4-fluoro-[1,1'-biphenyl]-3-yl)methanesulfonamide; N-(5-(5-((trans)-2-aminocyclopropyl)pyridin-2-yl)-2-fluorophenyl)methanesulfonamide; N-(3-(5-((trans)-2-aminocyclopropyl)pyridin-2-yl)phenyl)ethanesulfonamide-; N-(3-(5-((trans)-2-aminocyclopropyl)pyridin-2-yl)phenyl)-4-cyanobenzenesulfonamide; N-(3-(5-((trans)-2-aminocyclopropyl)pyridin-2-yl)phenyl)-3-cyanobenzenesulfonamide; N-(3-(5-((trans)-2-aminocyclopropyl)pyridin-2-yl)phenyl)-2-cyanobenzenesulfonamide; N-(3-(5-((trans)-2-aminocyclopropyl)pyridin-2-yl)-5-(trifluoromethyl)phenyl)-4-cyanobenzenesulfonamide; N-(4'-((trans)-2-aminocyclopropyl)-[1,1'-biphenyl]-3-yl)-1,1,1-trifluoromethanesulfonamide; 4'-((trans)-2-aminocyclopropyl)-6-hydroxy-[1,1'-biphenyl]-3-carbonitrile; 4'-((trans)-2-aminocyclopropyl)-[1,1'-biphenyl]-2-ol, 4'-((trans)-2-aminocyclopropyl)-3'-methoxy-[1,1'-biphenyl]-3-ol; N-(3-(5-((trans)-2-aminocyclopropyl)thiazol-2-yl)phenyl)-2-cyanobenzenesulfonamide; or a pharmaceutically acceptable salt or solvate thereof.

In other embodiments, LSD1 inhibitor compounds are selected from phenylcyclopropylamine derivatives, as described for example by Ogasawara et al. (2013, *Angew. Chem. Int. Ed.* 52:8620-8624, which is hereby incorporated by reference herein in its entirety). Representative compounds of this type are represented by formula XII:

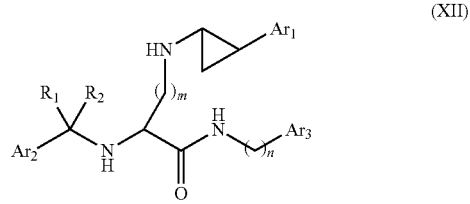

(XII)

wherein $Ar_1$ is a 5 to 7 membered aryl or heteroaryl ring;

$Ar_2$ and $Ar_3$ are each independently selected from a 5 to 7 membered aryl or heteroaryl ring, optionally substituted with 1 to 3 substituents;

$R_1$ and $R_2$ are independently selected from hydrogen and hydroxyl or taken together $R_1$ and $R_2$ form =O, =S or =$NR_3$;

$R_3$ is selected from hydrogen, —$C_{1-6}$alkyl or —OH;

m is an integer from 1 to 5; and n is an integer from 1 to 3;

or a pharmaceutically acceptable salt thereof.

In particular embodiments of formula (VII), one or more of the following applies:

$Ar_1$ is a six membered aryl or heteroaryl ring, especially phenyl, pyridine, pyrimidine, pyrazine 1,3,5-triazine, 1,2,4-trazine and 1,2,3-triazine, more especially phenyl;

$Ar_2$ is a six membered aryl or heteroaryl ring, especially phenyl, pyridine, pyrimidine, pyrazine 1,3,5-triazine, 1,2,4-trazine and 1,2,3-triazine, especially phenyl; especially where the six membered aryl or heteroaryl ring is optionally substituted with one optional substituent, especially in the 3 or 4 position;

$Ar_3$ is a six membered aryl or heteroaryl ring, especially phenyl, pyridine, pyrimidine, pyrazine 1,3,5-triazine, 1,2,4-trazine and 1,2,3-triazine, especially phenyl;

especially where the six membered aryl or heteroaryl ring is optionally substituted with one optional substituent, especially in the 3 or 4 position.

Particular optional substituents for $Ar_1$ and $Ar_2$ include —$C_{1-6}$alkyl, —$C_{2-6}$alkenyl, —$CH_2F$, —$CHF_2$, —$CF_3$, halo, aryl, heteroaryl, —C(O)NH$C_{1-6}$alkyl, —C(O)NH$C_{1-6}$alkylN$H_2$, —C(O)-heterocyclyl, especially methyl, ethyl, propyl, butyl, t-butyl, —$CH_2F$, —$CHF_2$, —$CH_3$, Cl, F, phenyl, —C(O)NH($CH_2)_{1-4}NH_2$ and —C(O)-heterocyclyl;

$R_1$ and $R_2$ taken together form =O, =S or =$NR_3$, especially =O or =S, more especially =O;

$R_3$ is H, —$C_{1-3}$alkyl or —OH, especially H, —$CH_3$ or —OH.

m is 2 to 5, especially 3 to 5, more especially 4, n is 1 or 2, especially 1.

In some embodiments the compounds of formula (XII) are compounds of formula (XIIa):

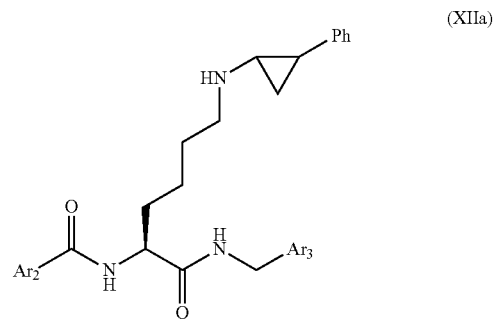

(XIIa)

wherein $Ar_2$ and $Ar_3$ are as defined for formula (XII).

Non-limiting compounds represented by formula XII include the following:

| Compound | $Ar_2$ | $Ar_3$ |
| --- | --- | --- |
| 1b | phenyl | phenyl |
| 1c | 4-methylphenyl | phenyl |
| 1d | 4-t-butylphenyl | phenyl |
| 1e | 4-chlorophenyl | phenyl |
| 1f | 4-fluorophenyl | phenyl |
| 1g | 4-phenyl-phenyl | Phenyl |
| 1h | 4-trifluoromethylphenyl | Phenyl |
| 1i | 3-(2-aminoethylcarbamoyl)phenyl | Phenyl |
| 1j | 3-(piperazine-1-carbonyl)phenyl | Phenyl |
| 1k | 4-phenyl-phenyl | 4-methylphenyl |
| 1l | 4-phenyl-phenyl | 4-fluorophenyl |
| 1m | 4-phenyl-phenyl | 4-phenyl-phenyl |
| 1n | 4-phenyl-phenyl | 4-t-butylphenyl |
| 1o | 4-phenyl-phenyl | 3-methylphenyl |
| 1p | 4-phenyl-phenyl | 3-fluorophenyl |
| 1q | 4-phenyl-phenyl | 3-phenyl-phenyl |

The synthesis and inhibitory activity of the compounds of formula (VII) are described by Ogasawara et al. (2013, supra).

Other LSD1 inhibitors include, but are not limited to those, e.g., disclosed in Ueda et al. (2009. *J. Am. Chem. Soc.*

131(48):17536-17537) including; Mimasu i (2010. *Biochemistry* June 22. [Epub ahead of print] PMID: 20568732 [PubMed—as supplied by publisher].

Other phenylcyclopropylamine derivatives and analogs are found, e.g., in Kaiser et al. (1962, *J. Med. Chem.* 5:1243-1265); Zirkle et al. (1962. *J. Med. Chem.* 1265-1284; U.S. Pat. Nos. 3,365,458; 3,471,522; 3,532,749) and Bolesov et al. (1974. *Zhumal Organicheskoi Khimii* 10:8 1661-1669) and Russian Patent No. 230169 (19681030).

The invention not only encompasses known LSD (e.g., LSD1 or LSD2) inhibitors but LSD inhibitors identified by any suitable screening assay. Accordingly, the present invention extends to methods of screening for modulatory agents that are useful for inhibiting a LSD (e.g., LSD1 or LSD2) and, in turn, for altering at least one of: (i) formation; (ii) proliferation; (iii) survival; (iv) viability; (v) maintenance; (vi) EMT; or (vii) MET of a LSD-overexpressing cell (e.g., a CSC), or for treating or preventing a cancer (e.g., a metastatic cancer). In some embodiments, the screening methods comprise (1) contacting a preparation with a test agent, wherein the preparation comprises (i) a polypeptide comprising an amino acid sequence corresponding to at least a biologically active fragment of a LSD (e.g., LSD1 or LSD2), or to a variant or derivative thereof; or (ii) a polynucleotide comprising a nucleotide sequence from which a transcript of a LSD gene (e.g., LSD1 or LSD2) or portion thereof is producible, or (iii) a polynucleotide comprising at least a portion of a genetic sequence (e.g., a transcriptional element) that regulates the expression of a LSD gene (e.g., LSD1 or LSD2), which is operably linked to a reporter gene; and (2) detecting a change in the level or functional activity of the polypeptide, the polynucleotide or an expression product of the reporter gene, relative to a reference level or functional activity in the absence of the test agent. A detected reduction in the level and/or functional activity of the polypeptide, transcript or transcript portion or an expression product of the reporter gene, relative to a normal or reference level and/or functional activity in the absence of the test agent, indicates that the agent is useful for altering at least one of: (i) formation; (ii) proliferation; (iii) survival; (iv) viability; (v) maintenance; (vi) EMT; or (vii) MET of a LSD-overexpressing cell (e.g., a CSC), or for treating or preventing the cancer. Suitably, this is confirmed by analyzing or determining whether the test agent alters at least one of: (i) formation; (ii) proliferation; (iii) survival; (iv) viability; (v) maintenance; (vi) EMT; or (vii) MET of a LSD-overexpressing cell, or treats or prevents the cancer.

Modulators falling within the scope of the present invention include inhibitors of the level or functional activity of a LSD (e.g., LSD1 or LSD2), including antagonistic antigen-binding molecules, and inhibitor peptide fragments, antisense molecules, ribozymes, RNAi molecules and co-suppression molecules as well as polysaccharide and lipopolysaccharide inhibitors of a LSD (e.g., LSD1 or LSD2).

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, desirably at least two of the functional chemical groups. The candidate agent often comprises cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule modulators of a LSD (e.g., LSD1 or LSD2) are particularly advantageous. In this regard, small molecules are desirable because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (e.g., by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogues.

Screening may also be directed to known pharmacologically active compounds and chemical analogues thereof.

Screening for modulatory agents according to the invention can be achieved by any suitable method. For example, the method may include contacting a cell expressing a polynucleotide corresponding to a gene that encodes a LSD (e.g., LSD1 or LSD2) with an agent suspected of having the modulatory activity and screening for the modulation of the level or functional activity of the LSD (e.g., LSD1 or LSD2), or the modulation of the level of a transcript encoded by the polynucleotide, or the modulation of the activity or expression of a downstream cellular target of the polypeptide or of the transcript (hereafter referred to as target molecules). Detecting such modulation can be achieved utilizing techniques including, but not restricted to, ELISA, cell-based ELISA, inhibition ELISA, Western blots, immunoprecipitation, slot or dot blot assays, immunostaining, RIA, scintillation proximity assays, fluorescent immunoassays using antigen-binding molecule conjugates or antigen conjugates of fluorescent substances such as fluorescein or rhodamine, Ouchterlony double diffusion analysis, immunoassays employing an avidin-biotin or a streptavidin-biotin detection system, and nucleic acid detection assays including reverse transcriptase polymerase chain reaction (RT-PCR).

It will be understood that a polynucleotide from which a LSD (e.g., LSD1 or LSD2) is regulated or expressed may be naturally occurring in the cell which is the subject of testing or it may have been introduced into the host cell for the purpose of testing. In addition, the naturally-occurring or introduced polynucleotide may be constitutively expressed—thereby providing a model useful in screening for agents which down-regulate expression of an encoded product of the sequence wherein the down regulation can be at the nucleic acid or expression product level. Further, to the extent that a polynucleotide is introduced into a cell, that polynucleotide may comprise the entire coding sequence that codes for the a LSD (e.g., LSD1 or LSD2) or it may comprise a portion of that coding sequence (e.g., the active site of the LSD) or a portion that regulates expression of the corresponding gene that encodes the LSD (e.g., a LSD1 promoter or a LSD2 promoter). For example, the promoter that is naturally associated with the polynucleotide may be introduced into the cell that is the subject of testing. In this instance, where only the promoter is utilized, detecting modulation of the promoter activity can be achieved, for example, by operably linking the promoter to a suitable reporter polynucleotide including, but not restricted to, green fluorescent protein (GFP), luciferase, β-galactosidase and catecholamine acetyl transferase (CAT). Modulation of expression may be determined by measuring the activity associated with the reporter polynucleotide.

These methods provide a mechanism for performing high throughput screening of putative modulatory agents such as proteinaceous or non-proteinaceous agents comprising synthetic, combinatorial, chemical and natural libraries. These methods will also facilitate the detection of agents which bind either the polynucleotide encoding the target molecule or which modulate the expression of an upstream molecule, which subsequently modulates the expression of the polynucleotide encoding the target molecule. Accordingly, these methods provide a mechanism of detecting agents that either directly or indirectly modulate the expression or activity of a target molecule according to the invention.

In alternative embodiments, test agents are screened using commercially available assays, illustrative examples of which include EpiQuik Histone Demethylase LSDI Inhibitor Screening Assay Kit (Epigentek Group, Brooklyn, N.Y.) or the LSDI Inhibitor Screening Assay Kit (Cayman Chemical Company, Ann Arbor, Mich.).

Compounds may be further tested in the animal models to identify those compounds having the most potent in vivo effects. These molecules may serve as "lead compounds" for the further development of pharmaceuticals by, for example, subjecting the compounds to sequential modifications, molecular modeling, and other routine procedures employed in rational drug design.

3. Therapeutic and Prophylactic Uses

In accordance with the present invention, it is proposed that agents that inhibit LSD (e.g., LSD1 or LSD2) function are useful as actives for altering at least one of: (i) formation; (ii) proliferation; (iii) survival, (iv) viability, or (v) maintenance of a LSD-overexpressing cell (e.g., a CSC or a non-CSC tumor cell); (vi) EMT of a LSD-overexpressing cell (e.g., a CSC); or (vii) MET of a LSD-overexpressing cell (e.g., a CSC), or for treating or preventing a cancer (e.g., a metastatic cancer). Thus, LSD inhibitor compounds, in accordance with the present invention, are useful, suitably in pharmaceutical compositions, for treating or preventing cancers, including metastatic cancers. As such the present invention contemplates pharmaceutical compositions for treating, preventing and/or relieving the symptoms of a malignancy, particularly a metastatic cancer, wherein the compositions comprise an effective amount of a LSD (e.g., LSD1 and/or LSD2) inhibitor and a pharmaceutically acceptable carrier and/or diluent.

Any LSD inhibitor can be used in the compositions and methods of the present invention, provided that the inhibitor is pharmaceutically active. A "pharmaceutically active" LSD inhibitor is in a form that results in a reduction, impairment, abrogation or prevention in the (i) formation; (ii) proliferation; (iii) survival; (iv) viability; or (v) maintenance of a LSD-overexpressing cell (e.g., a CSC or non-CSC tumor cell); or (vi) EMT of a LSD-overexpressing cell (e.g., a CSC), and/or in the enhancement of (vii) MET of a LSD-overexpressing cell (e.g., a CSC), and/or in the treatment and/or prevention of a malignancy, particularly a metastatic cancer, including the prevention of incurring a symptom, holding in check such symptoms or treating existing symptoms associated with the metastatic cancer, when administered to an individual in need thereof.

Modes of administration, amounts of LSD inhibitor administered, and LSD inhibitor formulations, for use in the methods of the present invention, are routine and within the skill of practitioners in the art. Whether a malignancy, particularly a metastatic cancer, has been treated is determined by measuring one or more diagnostic parameters indicative of the course of the disease, compared to a suitable control. In the case of an animal experiment, a "suitable control" is an animal not treated with the LSD inhibitor, or treated with the pharmaceutical composition without the LSD inhibitor. In the case of a human subject, a "suitable control" may be the individual before treatment, or may be a human (e.g., an age-matched or similar control) treated with a placebo. In accordance with the present invention, the treatment of a metastatic cancer includes and encompasses without limitation: (1) impairing, abrogating, reducing, preventing, or arresting the development of, the (i) formation; (ii) proliferation; (iii) maintenance; or (iv) EMT of a LSD-overexpressing cell (e.g., a CSC), or enhancing MET of a LSD-overexpressing cell (e.g., a CSC), in a patient; (2) treating a cancer (e.g., a metastatic cancer) in a subject; (3) preventing a cancer (e.g., a metastatic cancer) in a subject that has a predisposition to the cancer but has not yet been diagnosed with the cancer and, accordingly, the treatment constitutes prophylactic treatment of the cancer; or (iii) causing regression of a cancer (e.g., a metastatic cancer).

The compositions and methods of the present invention are thus suitable for treating an individual who has been diagnosed with a metastatic cancer, who is suspected of having a metastatic cancer, who is known to be susceptible and who is considered likely to develop a metastatic cancer, or who is considered likely to develop a recurrence of a previously treated metastatic cancer. The metastatic cancer may be hormone receptor positive or hormone receptor negative. In some embodiments, the metastatic cancer is hormone receptor negative and is thus resistant to hormone or endocrine therapy. In some embodiments in which the cancer is breast cancer, the breast cancer (e.g., the non-breast CMC tumor cells) is hormone receptor negative (e.g., estrogen receptor (ER) negative and/or progesterone receptor (PR) negative).

In some embodiments, and dependent on the intended mode of administration, the LSD inhibitor-containing compositions will generally contain about 0.000001% to 90%, about 0.0001% to 50%, or about 0.01% to about 25%, by weight of LSD inhibitor, the remainder being suitable pharmaceutical carriers or diluents etc. The dosage of the LSD inhibitor can depend on a variety of factors, such as mode of administration, the species of the affected subject, age, sex, weight and general health condition, and can be easily determined by a person of skill in the art using standard protocols. The dosages will also take into consideration the binding affinity of the LSD inhibitor to its target molecule, its bioavailability and its in vivo and pharmacokinetic properties. In this regard, precise amounts of the agents for administration can also depend on the judgment of the practitioner. In determining the effective amount of the agents to be administered in the treatment or prevention of a metastatic cancer, the physician or veterinarian may evaluate the progression of the disease or condition over time. In any event, those of skill in the art may readily determine suitable dosages of the LSD inhibitor without undue experimentation. The dosage of the actives administered to a patient should be sufficient to effect a beneficial response in the patient over time such as impairment, abrogation or prevention in the formation, proliferation, survival, viability or maintenance of CMCs (e.g., breast CMCs) and/or non-CMC tumor cells, in inhibition of EMT of non-CMC tumor cells, in stimulating MET of CMCs (e.g., breast CMCs) and/or in the treatment and/or prevention of a metastatic cancer. The dosages may be administered at suitable intervals to ameliorating the symptoms of the hematologic malignancy. Such intervals can be ascertained using routine procedures known to persons of skill in the art and can vary depending on the type of active agent employed and its formulation. For example, the interval may be daily, every other day, weekly, fortnightly, monthly, bimonthly, quarterly, half-yearly or yearly.

Dosage amount and interval may be adjusted individually to provide plasma levels of the active agent, which are sufficient to maintain LSD-inhibitory effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

In accordance with the practice of the present invention, inhibition of LSD (e.g., LSD1 and LSD2) by the LSD inhibitor will result in reduced formation, proliferation, survival, viability or maintenance of CSCs, which will in turn result in fewer non-CSC tumor cells differentiating from the CSCs and in more effective treatment of non-CSC tumor cells with an auxiliary cancer therapy or agent. Thus, the present invention further contemplates administering the LSD inhibitor concurrently with at least one cancer therapy that inhibits the proliferation, survival or viability of non-CMC tumor cells. The LSD inhibitor may be used therapeutically after the cancer therapy or may be used before the therapy is administered or together with the therapy. Accordingly, the present invention contemplates combination therapies, which employ a LSD inhibitor and concurrent administration of an cancer therapy, non-limiting examples of which include radiotherapy, surgery, chemotherapy, hormone abalation therapy, pro-apoptosis therapy and immunotherapy.

3.1 Radiotherapy

Radiotherapies include radiation and waves that induce DNA damage for example, γ-irradiation, X-rays, UV irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half life of the isotope, the strength and type of radiation emitted, and the uptake by the neoplastic cells.

Non-limiting examples of radiotherapies include conformal external beam radiotherapy (50-100 Grey given as fractions over 4-8 weeks), either single shot or fractionated, high dose rate brachytherapy, permanent interstitial brachytherapy, systemic radio-isotopes (e.g., Strontium 89). In some embodiments the radiotherapy may be administered in combination with a radiosensitizing agent. Illustrative examples of radiosensitizing agents include but are not limited to efaproxiral, etanidazole, fluosol, misonidazole, nimorazole, temoporfin and tirapazamine.

3.2 Chemotherapy

Chemotherapeutic agents may be selected from any one or more of the following categories:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyridines like 5-fluorouracil and tegafur, raltitrexed, methotrexate, cytosine arabinoside and hydroxyurea; anti-tumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and docetaxel; and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), UH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) anti-angiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense; and (viii) gene therapy approaches, including for example approaches to replace aberrant genes such as aberrant p53 or aberrant GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

3.3 Immunotherapy

Immunotherapy approaches, include for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies. These approaches generally rely on the use of immune effector cells and molecules to target and destroy cancer cells. The immune effector may be, for example, an antibody specific for some marker on the surface of a malignant cell. The antibody alone may serve as an effector of therapy or it may recruit other cells to actually facilitate cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a malignant cell target. Various effector cells include cytotoxic T cells and NK cells.

3.4 Other Therapies

Examples of other cancer therapies include phototherapy, cryotherapy, toxin therapy or pro-apoptosis therapy. One of skill in the art would know that this list is not exhaustive of the types of treatment modalities available for cancer and other hyperplastic lesions.

It is well known that chemotherapy and radiation therapy target rapidly dividing cells and/or disrupt the cell cycle or cell division. These treatments are offered as part of the treating several forms of cancer, aiming either at slowing their progression or reversing the symptoms of disease by means of a curative treatment. However, these cancer treatments may lead to an immunocompromised state and ensuing pathogenic infections and thus the present invention also extends to combination therapies, which employ both a LSD inhibitor, a cancer therapy and an anti-infective agent that is effective against an infection that develops or that has an increased risk of developing from an immunocompromised condition resulting from the cancer therapy. The anti-infective drug is suitably selected from antimicrobials, which include without limitation compounds that kill or inhibit the growth of microorganisms such as viruses, bacteria, yeast, fungi, protozoa, etc. and thus include antibiotics, amebicides, antifungals, antiprotozoals, antimalarials, antituberculotics and antivirals. Anti-infective drugs also include within their scope anthelmintics and nematocides. Illustrative antibiotics include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperozolid), glycopeptides, aminoglycosides (e.g., amikacin, arbekacin, butirosin, dibekacin, fortimicins, gentamicin, kanamycin, meomycin, netilmicin, ribostamycin, sisomicin, spectinomycin, streptomycin, tobramycin), β-lactams (e.g., imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol.

Illustrative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine.

Non-limiting examples of amebicides or antiprotozoals include atovaquone, chloroquine hydrochloride, chloroquine phosphate, metronidazole, metronidazole hydrochloride, and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine, and streptomycin sulfate.

As noted above, the present invention encompasses co-administration of an LSD inhibitor in concert with an additional agent. It will be understood that, in embodiments comprising administration of the LSD inhibitor with other agents, the dosages of the actives in the combination may on their own comprise an effective amount and the additional agent(s) may further augment the therapeutic or prophylactic benefit to the patient. Alternatively, the LSD inhibitor and the additional agent(s) may together comprise an effective amount for preventing or treating the metastatic cancer. It will also be understood that effective amounts may be defined in the context of particular treatment regimens, including, e.g., timing and number of administrations, modes of administrations, formulations, etc. In some embodiments, the LSD inhibitor and optionally the cancer therapy are administered on a routine schedule. Alternatively, the cancer therapy may be administered as symptoms arise. A "routine schedule" as used herein, refers to a predetermined designated period of time. The routine schedule may encompass periods of time which are identical or which differ in length, as long as the schedule is predetermined. For instance, the routine schedule may involve administration of the LSD inhibitor on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve concurrent administration of the LSD inhibitor and the cancer therapy on a daily basis for the first week, followed by a monthly basis for several months, and then every three months after that. Any particular combination would be covered by the routine schedule as long as it is determined ahead of time that the appropriate schedule involves administration on a certain day.

Additionally, the present invention provides pharmaceutical compositions for reducing or abrogating the proliferation, survival or viability of CMCs cells and for preventing or treating malignancies, particularly metastatic cancers, which comprise a LSD inhibitor and optionally a cancer therapy agent useful for treating malignancies. The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. Depending on the specific conditions being treated, the formulations may be administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the active agents or drugs of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

The drugs can be formulated readily using pharmaceutically acceptable carriers well known in the art into dosages suitable for oral administration. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more drugs as described above with the carrier, which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments may be added to the tablets or dragee coatings for identification or to characterize different combinations of active compound doses.

Pharmaceutical which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the drugs of the invention may also include injecting or implanting controlled releasing devices designed specifically for this purpose or other forms of implants modified to act additionally in this fashion. Controlled release of an agent of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes or microspheres.

The drugs of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (e.g., the concentration of an active agent, which achieves a half-maximal inhibition in activity of a LSD polypeptide). Such information can be used to more accurately determine useful doses in humans.

Toxicity and therapeutic efficacy of such drugs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See for example Fingl et al., 1975, in "The Pharmacological Basis of Therapeutics", Ch. 1 p1).

Alternately, one may administer the compound in a local rather than systemic manner, for example, via injection of the compound directly into a tissue, which is preferably subcutaneous or omental tissue, often in a depot or sustained release formulation.

Furthermore, one may administer the drug in a targeted drug delivery system, for example, in a liposome coated with tissue-specific antibody. The liposomes will be targeted to and taken up selectively by the tissue.

In cases of local administration or selective uptake, the effective local concentration of the agent may not be related to plasma concentration.

In order that the invention may be readily understood and put into practical effect, particular preferred embodiments will now be described by way of the following non-limiting examples.

EXAMPLES

Example 1

CSCs and Epigenetic Regulation

CSCs have several important in vitro properties. First, breast CSCs are characterized by the key surface markers $CD44^{high}$ $CD24^{low}$ (FIG. 1 A). Second, CSC-enriched populations have the ability to form spherical colonies in suspension cultures (termed mammospheres for breast CSCs) (FIG. 1 C). Third, CSC-enriched populations show enhanced resistance to chemotherapy and ionizing radiation. Fourth, they display a distinct transcriptome profile (FIG. 1 B). Therefore, CSCs represent a distinct population of cancer cells with distinct molecular mechanisms maintaining their unique in vitro properties.

Example 2

LSD1 Functions as an Epigenetic Regulator of Human Breast CSCs

Figure 2:
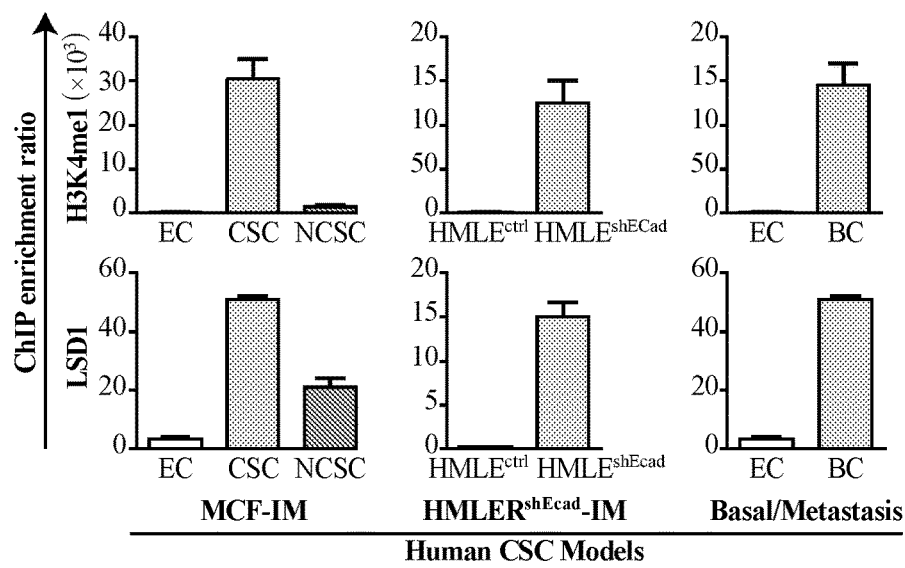
FIG. 2 is a graphical representation showing the results of H3K4me1 and LSD1 ChIP assays across the CD44 promoter region in three human CSC models. (EC, MCF-7 epithelial cell line; BC, MDA-MB 231 basal cell line).

H3K4me1 and LSD1 ChIP assays were conducted across the CD44 promoter region in three human CSC models. (EC, MCF-7 epithelial cell line; BC, MDA-MB 231 basal cell line). The results presented in FIG. 2 show that LSD1, H3K4me1 and H3K9me1 histone modification are enriched across key genes whose transcripts are predominantly enriched in breast CSCs (e.g., CD44, UPAR, laminin).

Example 3

Nuclear Staining of LSD1 in Human Normal and Breast Cancer Tissue

Figure 3:
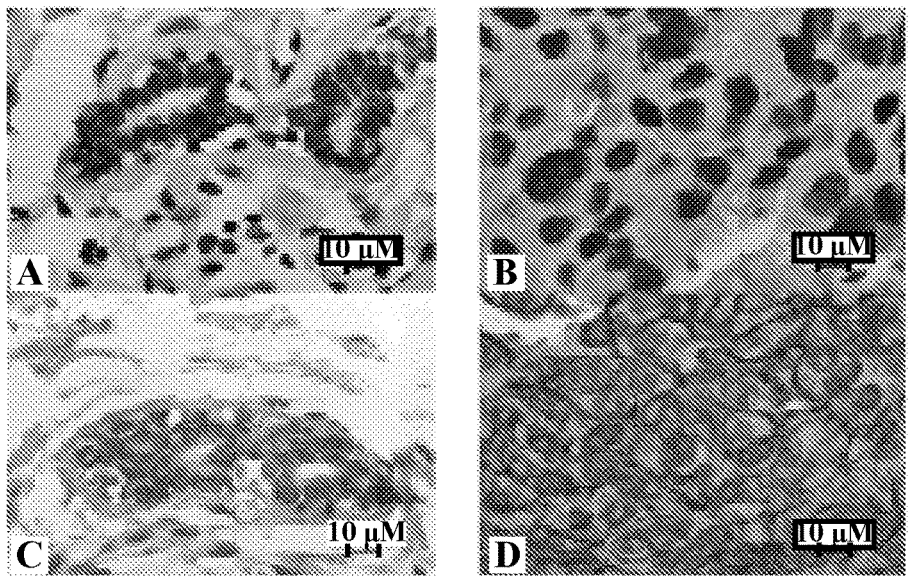
FIG. 3 is a photographic representation showing nuclear staining of LSD1 in human normal (A) and breast cancer tissue (B) and surface marker CD44 in human normal (C) and breast cancer tissue (D)

Nuclear staining of normal and human breast cancer tissue was carried out using an anti-LSD1 antibody. The results presented in FIG. 3 reveal: that normal breast tissue shows strong nuclear immunoreactivity for LSD1 (Abcam; 1/50 dilution) in normal ductal epithelium and adjacent stromal cells (see Panel A in FIG. 3); and that Grade 3 invasive ductal carcinoma (ER/PR$^-$Her2$^+$) shows strong nuclear immunoreactivity for LSD1 (see Panel B in FIG. 3). Inspection of a photomicrograph of normal breast tissue (see Panel C in FIG. 3) shows patchy weak membranous staining for CD44 (BD Pharmingen; 1/50 dilution) in normal ductal epithelium. By contrast, the same grade 3 invasive ductal carcinoma shows strong circumferential membranous staining with an antibody targeted against CD44 (see Panel D in FIG. 3).

Example 4

LSD1 siRNA Knockdown in Human Breast CSC Models Abolishes CSCs

Figure 4:
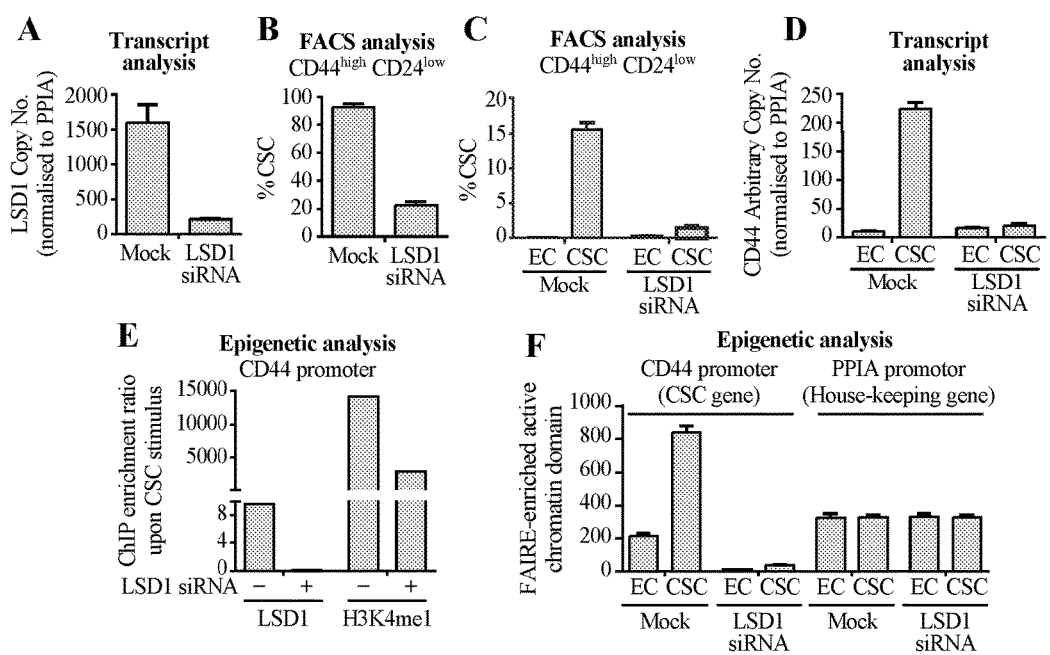
FIG. 4 is a graphical representation showing that LSD1 knockdown by siRNA inhibits the development of breast human $CD44^{high}$ $CD24^{low}$ CSCs in MDA MB-231 basal metastatic model: Transcript analysis (A), FACS analysis (B), MCF-7 IM model: FACS analysis (C), Transcript analysis (D) and by ChIP (E) and FAIRE analysis (F).

The present inventors successfully knocked down LSD1 in all their CSC models (see, FIG. 1) using validated pooled siRNAs (Santa Cruz) according to published protocols. Greater than 85% knockdown of LSD1 was observed in these systems (FIG. 4A). LSD1 knockdown led to: a decrease in CSCs as measured by FACS in the Basal/Metastasis model (FIG. 4B) and MCF-IM model (FIG. 4C); decreased transcription of CSC marker genes such as CD44 (FIG. 4D); reduction in mammospheres as measured by the mammosphere assay (data not shown); decrease in LSD1 and H3K4me1 marks measured by chromatin immunoprecipitation (ChIP) (FIG. 4E); inhibition of CD44 active chromatin domains measured by FAIRE (FIG. 4F).

Overall, these data show that LSD1 functions as an epigenetic regulator of human breast CSCs.

Example 5

LSD2 siRNA Knockdown in Human Breast CSC Models Abolishes CSCs

Figure 5:
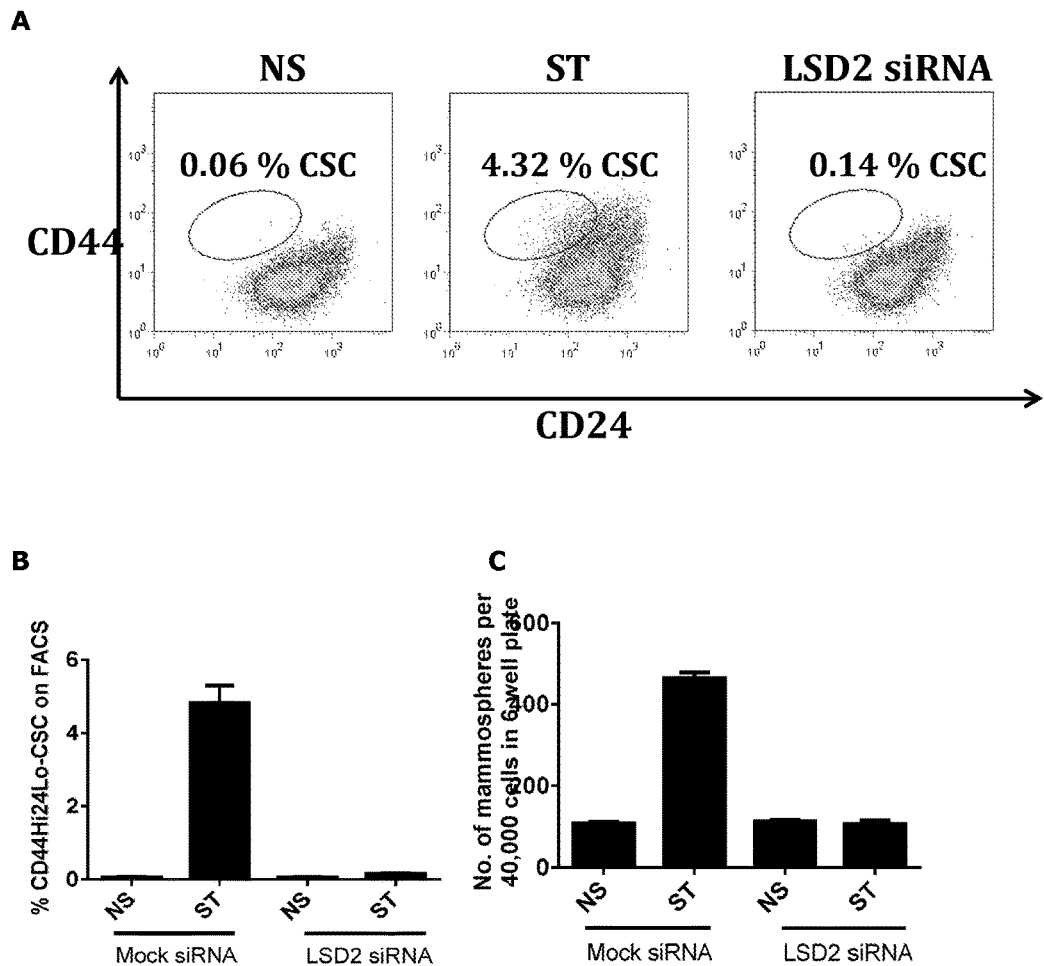
FIG. 5 is a graphical representation showing that LSD2 knockdown by siRNA inhibits the development of breast human $CD44^{high}$ $CD24^{low}$ CSCs using FACS analysis (A and B) and mammosphere assay (C).

The present inventors also successfully knocked down LSD2 in a breast CSC model using validated pooled siRNAs (Santa Cruz). Again, they observed >85% knockdown in $CD44^{high}$ $CD24^{low}$ breast cancer cells as assessed by flow cytometry (see, FIGS. 5A and B). LSD1 knockdown also led to: reduction in mammospheres as measured by the mammosphere assay (FIG. 5C).

Overall, these data show that LSD2 functions as an epigenetic regulator of human breast CSCs.

Example 6

Inhibition of LSD1 by Specific Inhibitor Reduces CSC Formation

Figure 6:
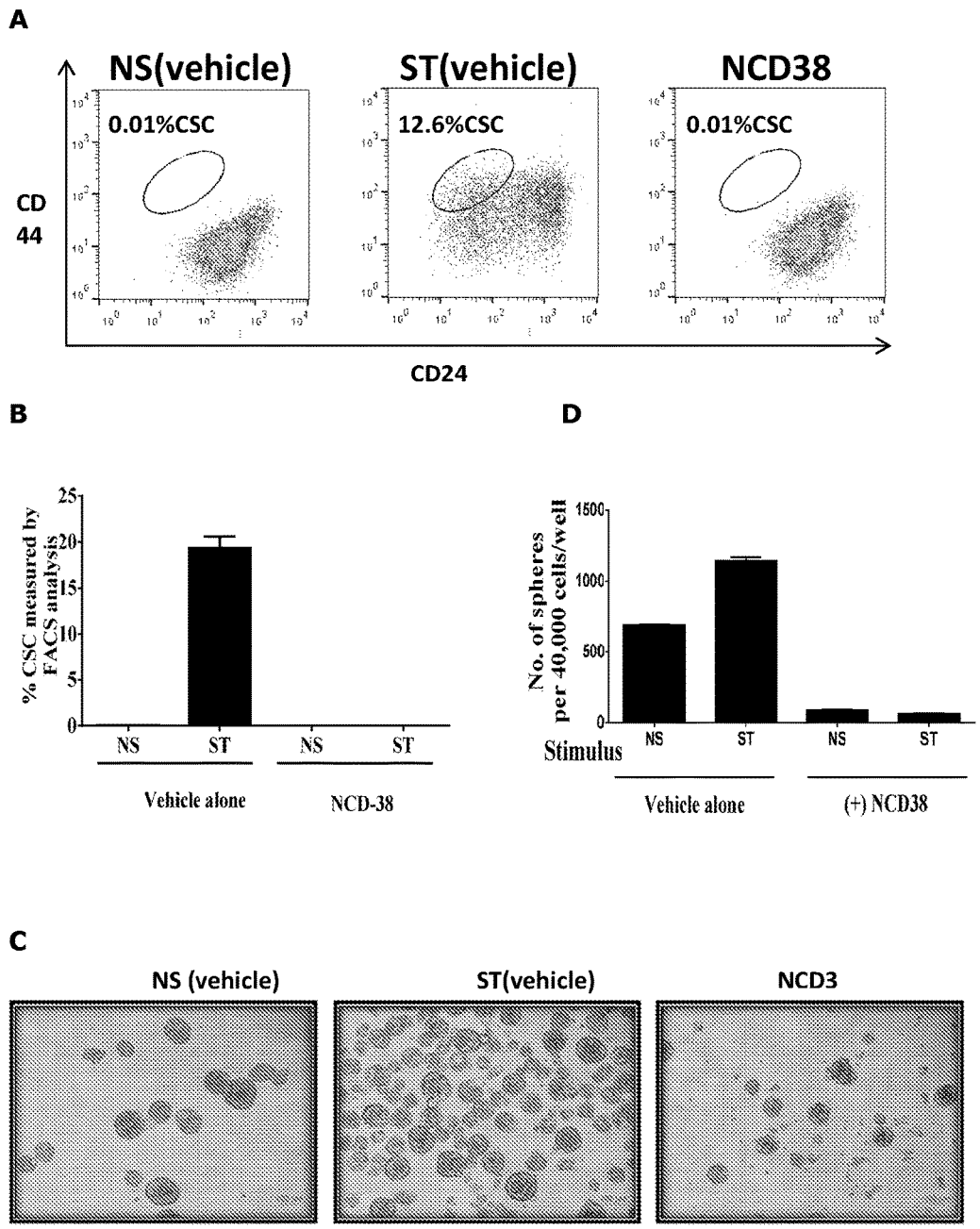
FIG. 6 is a graphical and photographic representation showing that NCD38 inhibits formation of CSCs in MCF-IM model. (A) LSD1 specific inhibitor NCD38 inhibits CD44 high CD24 low-CSC-like subpopulation in MCF-IM model. MCF-7 cells were either pre-incubated with vehicle alone or with NCD38 (5 μM for 17 hr), prior to PMA (0.65 ng/μl for 60 hours) stimulation (ST) or. Cells were subsequently stained with Hoechst 33528, APC-anti-CD44 and PE-anti-CD24 for 20 minutes on ice and subjected to FACS analysis. Circles on FACS plot indicate appropriate gating of $CD44^{high}/CD24^{low}$ CSC-like subpopulation and % CSC-like subpopulation is shown above the gates respectively. (B) Graphical representation of data in FIG. 6A above. Data represent the mean±standard error (SE) of three independent experiments. (C) 5 μM NCD38 reduce mammosphere formation in MCF-IM model. Mammosphere assay was performed with $4 \times 10^4$ MCF-7 cells/well in an ultra low attachment 6 well plates. MCF-7 cells were pre-incubated either with vehicle alone or NCD38 (5 μM for 17 hr) prior to PMA stimulation (0.65 ng/ml for 6 days) (ST) or left non-stimulated (NS). Phase contrast microscopic images of mammospheres were taken after 6 days of assay and only mammospheres larger than 60 μm were counted. (D) Graphical representation of FIG. 6C above. Data represent the mean±standard error (SE) of three independent experiments.

LSD1 specific inhibitor NCD-38 results in inhibition CSC formation in MCF-IM model as monitored by FACS (FIGS. 6A and B) and mammosphere assay (FIGS. 1C and D).

Example 7

Inhibition of LSD1 Results in Mesenchymal to Epithelial Transition (Met)

Figure 7:
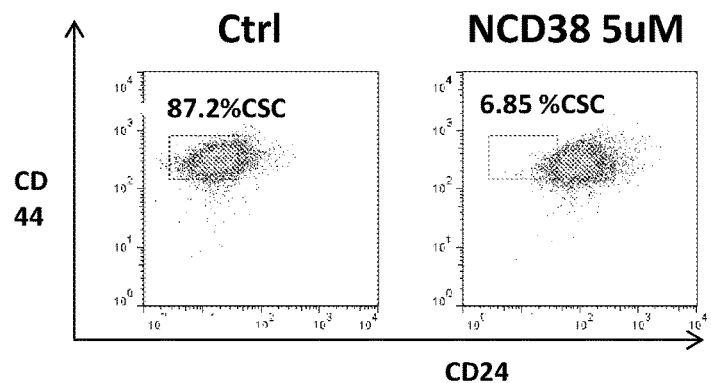
FIG. 7 is a graphical and photographic representation showing that the specific LSD 1 inhibitor NCD38 inhibits maintenance of human metastatic breast cancer cells and converts the cells to an epithelial form. (A) NCD38 inhibits CD44 high CD24 low-CSC-like subpopulation in Basal/metastatic model. MDA-MB 231 cells were either incubated with vehicle alone or with NCD38 (5 μM). Cells were subsequently stained with Hoechst 33528, APC-anti-CD44 and PE-anti-CD24 for 20 minutes on ice and subjected to FACS analysis. Percent CSC-like subpopulation is shown in the bar graph. Data represent the mean±standard error (SE) of three independent experiments. (B) Graphical representation of FIG. 7A above. Data represent the mean±standard error (SE) of three independent experiments. (C) LSD1 inhibitor NCD38 inhibit EMT in Basal/metastatic model. Phase contrast microscopy images of MDA-MB 231 cells were captured either without pre-treatment of LSD1 specific inhibitor (-Control) or with treatment of NCD38 (5 μM) (+NCD38).
Figure 7:
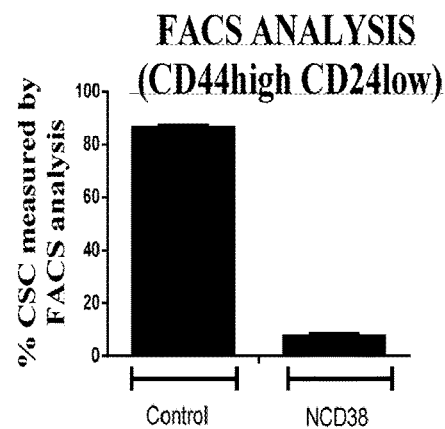
Figure 7:
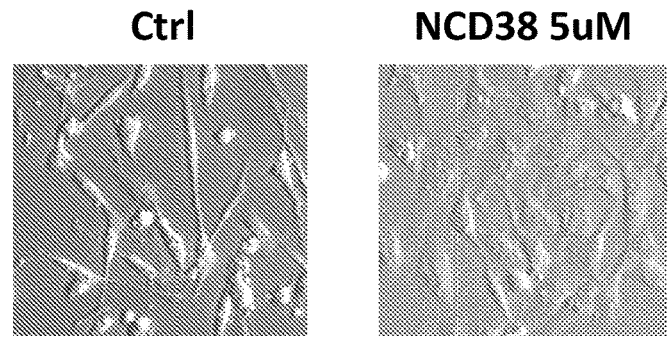

Treatment of basal metastatic model (MDA-MB 231) with LSD1 specific inhibitor NCD-38 results in a decrease of CSC formation (FIGS. 7A and B) and in conversion of mesenchymal cells in to epithelial cells (FIG. 7 C).

Example 8

Figure 8:
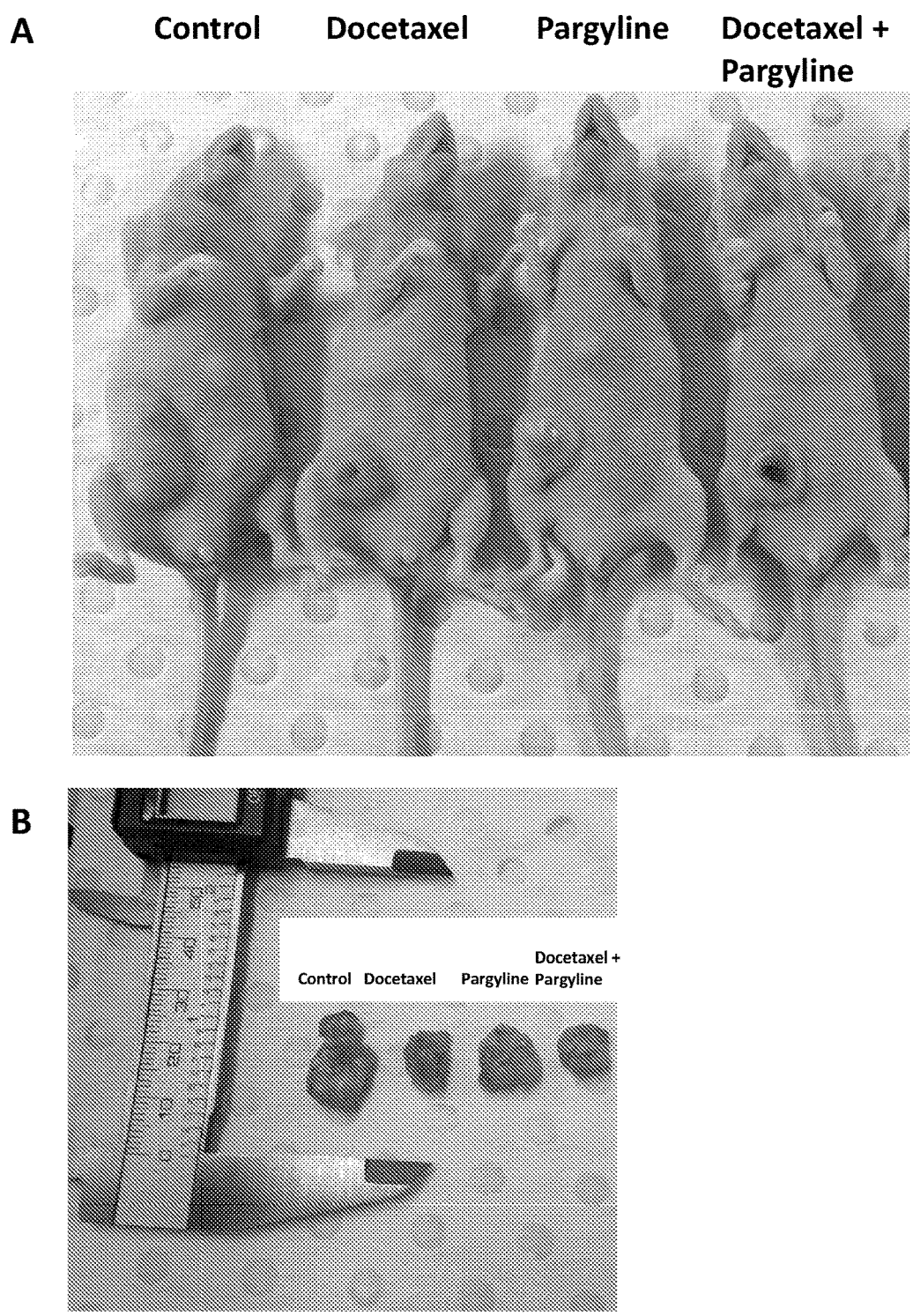
FIG. 8 is a photographic representation showing that the LSD1 inhibitor pargyline in combination with chemotherapeutic agent docetaxel reduces size of tumor in in vivo mice xenograft model. $5 \times 10^6$ MDA-MB-231 cells were injected into the mammary fat pad of each mouse. Treatments were initiated at a tumor volume of 50 mm$^3$ at the stated doses. (A) Representative mice from each treatment group after four weeks of treatment. (B) Weekly tumor sizes of dissected tumors at week four of treatment.
Figure 9:
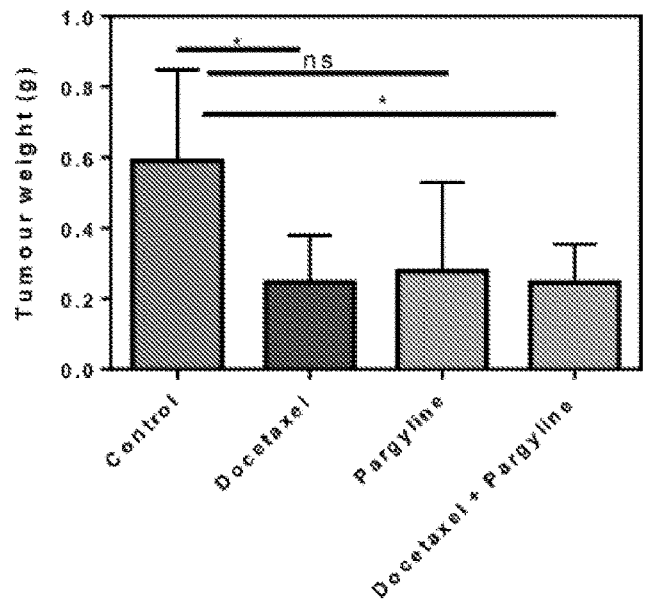
FIG. 9 is a graphical representation showing that pargyline in combination with docetaxel reduces volume and weight of tumor in in vivo mice xenograft model after seven weeks of treatment initiation. $5 \times 10^6$ MDA-MB-231 cells were injected into the mammary fat pad of each mouse. Treatments were initiated at a tumor volume of 50 mm$^3$ at the stated doses. Tumor volumes were measured every week until seven weeks of treatment. (A) Tumor weight in grams from each treatment group after seven weeks of treatment. Tumor weight is mean±standard error (SE) of three mice. (B) Weekly tumor volumes in mm$^3$. Days for chemotherapy treatments has been shown by black arrows on the graph. Tumor volume is mean±standard error (SE) of five or more mice.
Figure 9:
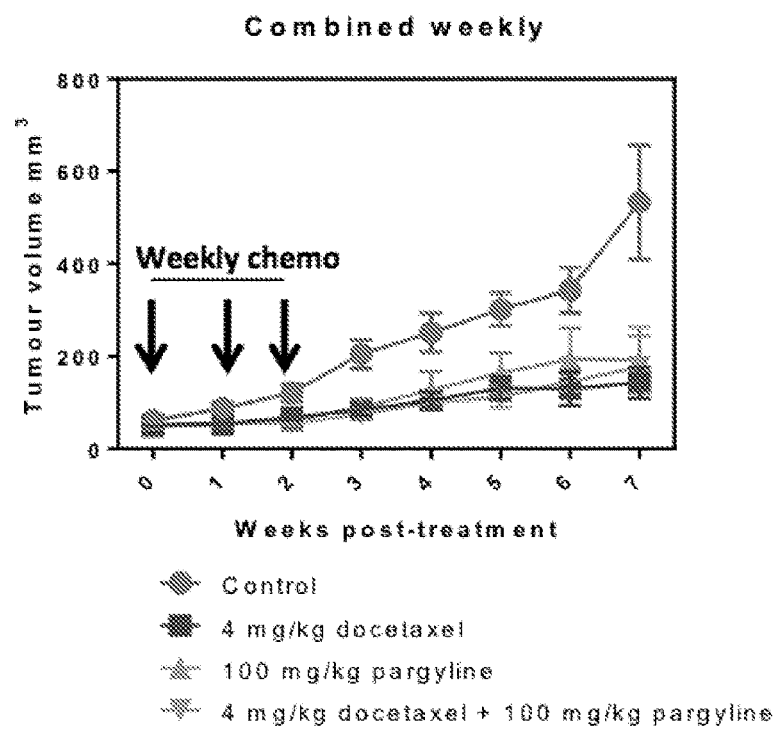

Reduction of Tumor Sizes by LSD1 Inhibitor in Combination with Chemotherapy LSD1 inhibitor pargyline results in reduced tumor size in combination with chemotherapeutic agent Docetaxel in mice xenograft model (FIG. 8A, B, FIG. 9A, B).

Example 9

Figure 10:
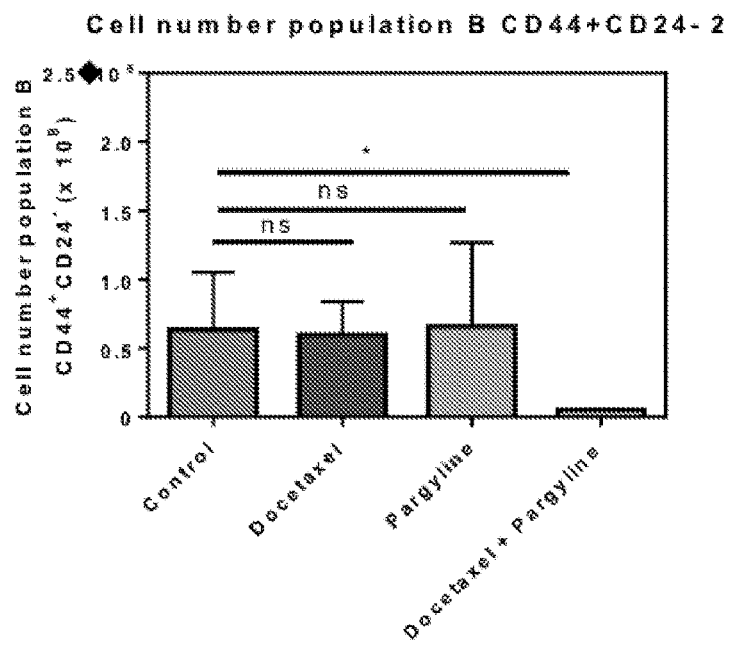
FIG. 10 is a graphical representation showing that pargyline in combination with docetaxel reduces cancer stem cells of in vivo mice tumors. 5×10⁶ MDA-MB-231 cells were injected into the mammary fat pad of each mouse. Treatments were initiated at a tumor volume of 50 mm³ at the stated doses. Mice were sacrificed on seven weeks of treatment. Single cell suspensions were made and cells were subsequently stained with Hoechst 33528, APC-anti-CD44 and PE-anti-CD24 for 20 minutes on ice and subjected to FACS analysis. (A) Percent CSC subpopulation from each treatment group. (B) CD44 mRNA expression of dissected tumors from each group by real-time PCR. Data represent the mean±standard error (SE) of five mice in each group.
Figure 10:
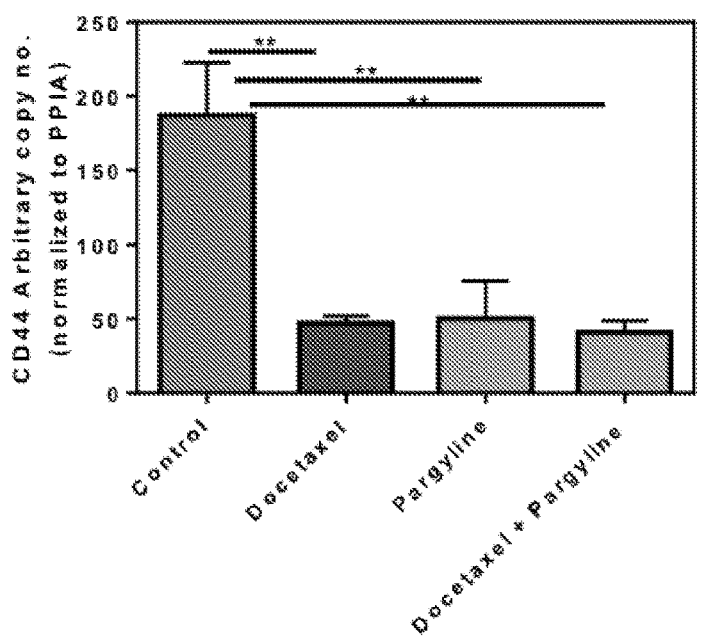

Inhibition of CSC Subpopulation by Combination of Chemotherapy and LSD1 Inhibitor Treatment of mice with LSD1 inhibitor, pargyline along with chemotherapeutic agent Docetaxel resulted in reduced CSC subpopulation as measured by FACS (FIG. 10A) and transcript (FIG. 10B).

Materials and Methods

General Reagents

Chemicals

All the reagents used were either classified molecular biology or analytical grade.

Cell Lines from the American Type Culture Collection (ATCC)

The adherent human mammary adenocarcinoma cell lines including MCF-7 (ATCC® number HTB-22), MDA-MB-231 (ATCC® number HTB-26), MDA-MB-468 (ATCC® number HTB-132), human adherent mammary ductal carcinoma T-47D (ATCC® number HTB-133) and human cervix carcinoma including HeLa (ATCC® number CCL-2) were obtained from ATCC (VA, USA). Stocks were stored at −196° C. in 5×10$^6$ cells/mL aliquots in either RPMI or DMEM Complete medium (containing 45% heat inactivated foetal calf serum (FCS; Sigma-Aldrich, St. Louis, Mo.) and 9% dimethyl sulfoxide (DMSO) solution (Cambridge Isotope Laboratories, Inc., Andover, Mass.). Cell stocks were thawed in complete media, RPMI or DMEM, and checked for mycoplasma contamination. Cell lines were frozen as stocks described in cryotubes (NUNC, Roskilde, Denmark) at −70° C. overnight and removed to long term storage in liquid nitrogen.

Media, Buffers, and Solutions

All media, buffers and solutions were obtained either from JCSMR Media/Wash-up Facility, ANU, Canberra, Australia or purchased from Gibco (Invitrogen Corporation, NY). RPMI-1640 (Gibco #11875-093) or Dulbecco's Modified Eagle Medium (DMEM) (1×, liquid, low glucose, Gibco #12320-32) complete cell culture media were freshly prepared for tissue culture according to experimental demand by supplementing RPMI/DMEM plus HEPES with 10% heat inactivated FCS, 0.1% PSN antibiotics and 2 mM L-glutamine.

Antibiotics

Antibiotic stocks were dissolved in DDW filtered through 0.22 μm filters (Millipore, NSW, Australia) and prepared by the JCSMR Media Facility, ANU, Canberra, Australia. Penicillin, streptomycin and neomycin (PSN) antibiotics (1000× stock): 30.07 g/L Penicillin G Sodium (MP Biomedicals, LLC), 50 g/L Streptomycin Sulphate (Sigma-Aldrich, St. Louis, Mo.) and 50 g/L Neomycin Sulphate (Sigma-Aldrich, St. Louis, Mo.). PSN was added to all RPMI/DMEM Complete medium except where otherwise stated.

Oligonucleotides

Primer/probe sets for gene expression analysis were purchased online from Taqman® Gene expression Assays (Applied Biosystems, Foster City, Calif.). Human TaqMan® probe sets used for quantitative cDNA real-time PCR included laminin-5, Fibronectin, Integrin-β, snail-1, uPAR, E-cadherin, vimentin, MMP-1, Zeb1, CD44, CD24, LSD1, PKC-θ and cyclophilin A. All primer sequences used for quantitative real-time PCR analysis of transcript are listed in Table 3.

All genomic DNA oligonucleotides were purchased online as Guaranteed Oligos from EasyOligoes Australia (Sigma-Aldrich, St. Louis, Mo.) as 100 μM stocks. Primer concentrations were optimized to achieve similar amplification efficiencies between different primer sets for the same gene. All oligonucleotide primer sequences used for quantitative real-time PCR are listed in Table 4.

Antibodies and Conjugates

All antibodies for this study were purchased from commercial sources. Details of all commercially purchased antibodies are listed in Table 5.

Kits 100 mM dNTP set (4×25 μmol) kit (Astral scientific Pty. Ltd., NSW, Australia)

Platinum® Taqman DNA Polymerase (Invitrogen, Carlsbad, Calif.)

QIAmp® Blood Mini Kit (Qiagen, Valencia, Calif.)

Superscript™ III RNaseH-Reverse Transcriptase kit (Invitrogen, Carlsbad, Calif.)

PowerSYBER Green PCR Master Mix (Applied Biosystems, Foster City, Calif.)

Taqman® universal PCR Master Mix (Applied Biosystems, Foster City, Calif.)

Taqman® MicroRNA Reverse Transcription kit

Enzymes and markers

Complete Protease Inhibitor Cocktail Tablets (Roche Diagnostics, Mannheim, Germany)

DNAse I, RNase-free (Roche Diagnostics, Mannheim, Germany)

Proteinase K (solution), RNA grade (Invitrogen, Carlsbad, Calif.)

Superscript™ III RNaseH-Reverse Transcriptase (Invitrogen, Carlsbad, Calif.)

Cell Culture

Mammalian Cell-Lines

The adherent human mammary adenocarcinoma MCF-7 cells lines were grown in DMEM Complete media. After thawing the cells were kept in DMEM Complete media in a sterile 75 cm² flask for 2 days before first splitting. Once confluent (after 2 days), cells were washed with 10 mL pre-warmed D-PBS (Gibco-BRL, Gaitherburg, Mass.) before adding 1 mL of 0.05% trypsin-EDTA (1×) (Gibco-BRL, Gaitherburg, Mass.) on washed cells. Cells were then incubated for 3 minutes at 37° C. in order to detach the cells, followed by addition of another 10 mL DMEM media. Cells were then centrifuged at 300×g for 10 minutes prior to re-suspension in 1 mL of fresh complete DMEM media and counted subsequently by Vi-CELL-XR counter before splitting at desired density of cells. Cells were passaged subsequently every 2-3 days depending on experimental demands and were sub-cultured when reached 80% confluences. For most of the experiments, 4×10⁴ cells/well of a 24 well plate, 4×10⁵ cells/75 cm² flask or 4×10⁶ cells/375 cm² flask were seeded one day before the experiment unless otherwise stated. MDA-MB-231All cells were grown in a humidified atmosphere of 5% $CO_2/O_2$ and incubated at 37° C. in a Hepa-Filtered Infrared (IR) Incubator (Forma Scientific Inc., Materietta, Ohio). All other cell lines used were grown and passaged in same way except using RPMI-1640 Complete media.

TABLE 3

HUMAN PRIMER/PROBE SET FOR REAL-TIME PCR FROM TAQMAN ®

| Gene | NCBI Location Chromosome | Assay details | Accession number | Amplicon size (bp) |
|---|---|---|---|---|
| CD44 | Chr. 11 - 35160417-35253949 | Hs00153304_m1 | NM_000610.3 | 86 |
| CD24 | Chr. Y - 21152526-21154705 | Hs00273561_m1 | NM_013230.2 | 162 |
| uPAR | Chr. 19 - 44150248-44174502 | Hs00182181_m1 | NM_002659.2 NM_001005377.1 NM_001005376.1 | 64 |
| Zeb1 | Chr. 10 - 31608101-31818742 | Hs00611018_m1 | NM_001128128.2 NM_030751.4 | 77 |
| LSD1 | Chr. 1: 23345941-23410184 | Hs01002741_m1 | NM_001009999.2 NM_015013.3 | 63 |
| Laminin-5 | Chr. 1 - 183155174-183214262 | Hs00194333_m1 | NM_005562.2 NM_018891.2 | 132 |

TABLE 4

HUMAN PRIMER/PROBE SET FOR REAL-TIME PCR FROM EASYOLIGO

| Gene | Genomic primer (5'→3') |
|---|---|
| CD44 | OLIGO Seq |
| | FORWARD PRIMER |
| | TGAGCTCTCCCTCTTTCCAC |
| | REVERSE PRIMER |
| | TTGGATATCCTGGGAGAGGA |
| uPAR | OLIGO Seq |
| | FORWARD PRIMER |
| | GGGAAGCAAAGCAAGGGTTA |
| | REVERSE PRIMER |
| | GTTTTGTCAGGAGGGATACTGG |

TABLE 5

ANTIBODY DETAILS

| Antibody | Supplier | Catalogue number | Stock concentration | Final concentration used |
|---|---|---|---|---|
| H3K4Me2 | Millipore | 07-030 | Polyclonal Antibody | 2.5 µg/tube |
| H3K4Me1 | Abcam | ab8895 | 0.3 mg/mL | 2.5 µg/tube |
| LSD1 | Millipore | 07-705 | Polyclonal Antibody | 5 µg/tube |
| Pol-II (c-21) | Abcam | ab817 | 1 mg/mL | 5 µg/tube |
| APC Mouse Anti-Human CD44 | BD Pharmingen | 559942 | Polyclonal Antibody | 1:100 of stock |
| PE Mouse Anti-Human CD24 | BD Pharmingen | 555428 | Polyclonal Antibody | 1:100 of stock |

Cell Viability and Density Counts

Cell viability was determined by using Vi-CELL-XR Counter (Beckman Coulter Ireland Inc., Galway, Ireland). Commercially available Vi-CELL Counter reagent packs were purchased from Beckman Coulter Ireland Inc., Galway, Ireland. A 50 µL aliquot of re-suspended cells (in 1 mL media) was diluted 1:10, in 450 µL media and loaded in the Vi-CELL counter cup to perform cell count and viability check. Cell viability counts were constantly >98% unless otherwise stated.

Mycoplasma Detection

Prior to freezing and after thawing cells were always checked for mycoplasma contamination and only mycoplasma-free cells were used for all the experiments. Mycoplasma detection was performed with MycoAlert Q Mycoplasma detection kit (Lonza, Me. USA).

Stimulation Conditions

MCF-7 cells were seeded one day before stimulation at a set density according to the experimental demand. Potential inducers of EMT were tested including Phorbol 12-Myristate 13-acetate (PMA) (Sigma-Aldrich, St. Louis, Mo.), and TGF β (R&D systems, Minneapolis, Minn.) at various concentrations and incubation length as specified in Table 6.

LSD1 Inhibition Conditions

The commercial LSD1 inhibitors used and supplier information are described in Table 7. Corresponding control samples with equivalent concentration of dissolving media or vehicle, usually DMSO (unless otherwise stated) was also included for each experiment.

Epithelial to Mesenchymal Transition (EMT) Assay

EMT assays were performed in 24-well plates (Costar, Corning Inc., Corning, N.Y., USA). For this assay, usually MCF-7 cells were seeded at $4 \times 10^4$/well/500 µL media one day before the experiment unless otherwise specified. Cells were stimulated with various EMT stimuli prepared in warm media the following day and monitored for EMT changes under the microscope specified below. The percentage of EMT was generally calculated based on phenotype counting 100 cells per field under the microscope. All the potential EMT stimuli used herein are described in Table 6 and they were prepared and stored as per supplier specification.

TABLE 6

DETAILS OF POTENTIAL EMT STIMULI

| EMT Inducer | Supplier & Catalogue number | Stock concentration | Final concentration & stimulation time |
| --- | --- | --- | --- |
| PMA | Sigma-Aldrich (P8139) | 1 mg/mL | 20 ng/mL to 0.2 ng/mL for 2 hour to 60 hour |
| Recombinant human TGF-β | R&D systems (240/b-CF) | 10 µg/mL in PBS | 2.5 ng/mL for 2 hour to 60 hour |

TABLE 7

LSD1 INHIBITOR INFORMATION

| Inhibitor | Supplier & Catalogue number | Final concentration & Pre-incubation time |
| --- | --- | --- |
| Pargyline | Cayman (10007852) | 3 mM for 17 hour |
| Phenelzine | Sigma (P6777) | 500 µM for 17 hour |
| Tranylcypromine | Enzo life sciences (EL-217) | 1 µM for 17 hour |

Mammosphere Assay

The following mammosphere culture media components were purchased from StemCell Technologies Inc., BC, Canada: Mammocult Basal medium (Human) (catalogue number-05621), Mammocult Proliferation Supplements (Human) (catalogue number-05622), heparin (catalogue number-07904) and hydrocortisone (catalogue number-07904). Hydrocortisone powder was freshly dissolved into mammocult basal medium to get $10^{-4}$M solution on the day of experiment. 50 mL of Mammocult complete media was then prepared by addition of 45 mL Mammocult basal medium, 5 mL mammocult proliferation supplements, 100 µL of the 0.2% heparin stock, 500 µL of $10^{-4}$M stock of hydrocortisone and 50 µL of the PNS. Mammocult complete media was either used on same day or stored for not more than 7 days at 4° C.

MCF-7 cells were grown in a 175 cm² cell culture flask and harvested using a cell scraper (Zellschaber, Switzerland) or FACS sorted as specified below. Importantly trypsin treatment was never used for harvesting cells as it interferes with the mammosphere assay. Harvested cells were then re-suspended in 1 mL mammocult complete media and centrifuged at 500×g for 3 minutes at 20° C. The cell pellet was then re-suspended in 1 mL mammocult complete media before counting the cells on the Vi-CELL counter. Cell dilutions were then prepared to stain 40,000 cells/2 mL and 2 mL of cells were seeded in the 6 well-ultra low adherent, flat bottom plates (Costar, Corning Inc, Corning, N.Y., USA). Cells were either stimulated or not treated according to the experimental protocol and incubated at 37° C., under 5% $CO_2$ for 7 days in a Hepa-Filtered Infrared (IR) Incubator (Forma Scientific Inc., Marietta, Ohio). Mammospheres larger than 60 µm were counted per well on day 7 and pictures were taken with an Olympus microscope. All the mammosphere assays were performed in duplicate wells and the entire procedure was repeated at least twice.

Immunofluorescence

Fluorescence-Activated Cell Sorting (FACS)

Cells from each well/flask were harvested by means of trypsin treatment followed by two washes with PBS. Washed cells then re-suspended in an antibody cocktail consisting anti-CD44-APC, anti-CD24-PE antibodies (details in Table 5) and Hoechst 33258 dye (final dilution of 1:1000) (Invitrogen, Carlsbad, Calif.) in 1% FCS-PBS solution. Cells re-suspended in antibody cocktail were incubated for 20 minutes at 4° C. Cells were next washed twice with PBS and re-suspended in 1% FCS-PBS solution (volume based on cell number) and kept on ice until analyzed by FACS. Forward scatter (FSC) and side scatter parameters were selected with FITC fluorochrome excited by 488 nm argonion laser, PE fluorochrome excited by 488 nm and Hoechst fluorochrome excited by 350 nm helium-cadmium UV laser.

Flow Cytometry data was produced using either BD FACS LSR Flow Cytometer (Becton Dickinson Biosciences) or BD FACS Aria™ II Flow Cytometer (Becton Dickinson Biosciences) and analyzed using the data acquisition software CellQuest Pro (Becton Dickinson Biosciences) and FlowJo (Tree Star Inc., Ashland, Oreg.) software at the MCRF facility, JCSMR, ANU, Canberra, Australia. Single colour controls were used to set compensation parameters. Isotype controls were used for all corresponding primary antibodies in each experiment.

CD44 and CD24 Staining Optimization in MCF-7 Cells

The FACS gating strategy used in this thesis is adopted and modified from the pioneer breast cancer stem cell publications (Al-Hajj et al., 2003) which sorted cells based on the $CD44^{high}$ and $CD24^{low}$ expression. Expression of $CD44^{high}$ and $CD24^{low}$ has been shown to be associated with human breast cancer stem cells (Al-Hajj et al., 2003; Sleeman et al., 2006; Mani. et al., 2008). To confirm that anti-CD44-APC and anti-CD24-PE antibodies were specific, isotype control antibodies were used. The isotype (negative controls) used for anti-CD24-PE was PE Mouse-Anti-human IgG2aK and for anti-CD44-APC was APC-Mouse-Anti-human IgG2bK. First, all the cells were stained with Hoechst 33258 to monitor cell viability. In addition cells were stained with varying concentrations of either APC or PE isotypes controls.

Microscopy

Fluorescence Microscopy

Cells were stained as outlined above and mounted on coverslips. Stained cells were viewed under oil immersion at ×100 magnification using Olympus Fluorescence 1×71 microscope (Olympus, Tokyo, Japan) or 60× magnification or Leica confocal microscope (Leica microsystems). Images on Olympus Fluorescence 1×71 microscope were captures using DPController camera software version 1.2.1.108 (2002 Olympus optical Co., LTD) and images on Leica confocal microscope were captured using Leica application suite, 2.0.0 program. Images were analyzed using Photoshop CS3 (Adobe Systems Inv., San Jose, Calif.). GFP/FAM vector transfected wells or flasks were viewed under Olympus Fluorescence 1×71 microscope using FITC excitation filter 406-495 nM filter (WIB).

Phase-Contrast Microscopy

Phase contrast microscopy was utilized for EMT and wound healing assays under 10× or 20× magnification of Olympus Fluorescence 1×71 microscope. Images were captured and analyzed as described above except that wound healing assay pictures were also analyzed by Image J software (Free software in Public domain developed by NIH).

Transfection

DNA Transfection

Conditions were optimized for DNA transfection in MCF-7 and T-47D cells by using commercially available transfection agents, FuGENE 6 (Roche Diagnostics, Mannheim, Germany) (the detailed method for FuGENE 6 is described below). To achieve the maximum transfection efficiency, initially, the transfection reagents were examined at varying ratio of reagent: DNA/oligo (GFP-expression vector for optimization). For all the DNA transfections cells were seeded at $1 \times 10^5$ cells per well in 500 μL of antibiotic-free media 24 hour prior to the commencement of transfection in 24 well plate and transfections were performed as per the manufacture's guidelines. The dilution medium used for transfections, was OptiMEM® I Reduced-Serum Medium (1×), liquid (Invitrogen, Carlsbad, Calif.). Transfection percentage was checked after 36-48 hours by FACS as described above.

DNA Transfection Using FuGENE 6 Reagent

For a single reaction in 500 μL total volume (per well of 24 well plate), 0.9 μL FuGENE 6 was added into a 1.5 mL Eppendorf tube containing 10 μL of OptiMEM® I Reduced-Serum Medium, mixed well and incubated for 5 minutes at room temperature. After 5 minutes, either 0.4 μg or 0.3 μg GFP tagged DNA (volume of DNA was calculated depending upon the concentration of specific DNA oligonucleotide used) was added into the tube to get a 2.25:1 or 3:1 ratio of FuGENE 6 respectively. DNA and the complex were then incubated for 45 minutes at room temperature. After 45 minutes, 20 μL of the FuGENE-DNA complex was added on top of the cells drop wise and mixed by swirling the plate and plates were incubated at 37° C. for 36-48 hours.

siRNA Transfection

Lyophilized Silencer® FITC Conjugate negative control siRNA (Mock) (sc-36869); validated LSD1 siRNA (sc-60970) and LSD2 siRNA (sc-95467) was purchased from Santa Cruz Biotechnologies, California. The specificity of these siRNAs has been previously published (Sutcliffe et al., 2011. Molecular Cell 6:704-719; Yang et al., 2010. Proc. Natl. Acad. Sci. USA 107: 21499-21504. Forward transfections with 10 nM siRNA were performed in MCF-7 cells by using Lipofectamine 2000 (Invitrogen, Carlsbad, Calif.). Forward transfection methods were performed in 24 well plates ($4 \times 10^4$ cells) for EMT assays and for transcript analysis, while for Chromatin Immuno-Precipitation (ChIP) assays where large quantities of cells were required, transfections were performed in 25 cm² flasks ($4 \times 10^5$ cells).

Briefly, for setting up forward transfection reactions in 24 well plates, $4 \times 10^4$ MCF-7 cells per well were seeded in 500 μL of antibiotic free media 24 hours prior to transfection. 250 μL DEPC-water was added in the 20 nmol lyophilized siRNA stock to get a 20 μM concentration stock. To achieve a final siRNA concentration of 10 nM (for one reaction in total volume of 500 μL media in one well of 24 well plate), 3 μL of 20 μM siRNA stock was further diluted in 50 μL Opti-MEM® I and incubated for 5 minutes at room temperature. This step was immediately followed by a further dilution of Lipofectamine by adding 1 μL Lipofectamine (for one reaction) in 50 μL Opti-MEM® I, followed by 5 minutes incubation at room temperature. 50 μL of diluted siRNA and 50 μL of diluted Lipofectamine solutions were then mixed together to get 100 μL of the siRNA-Lipofectamine complex. This complex was subsequently incubated in the dark, at room temperature for 20 minutes. The resultant siRNA-Lipofectamine complex was carefully pipette onto the surface of the cells and mixed by gently rocking the plate back and forth. Plates were incubated for 48-72 hours and transfection efficiency was checked by flow cytometry (refer above for detailed method of flow cytometry analysis). The knockdown was checked with three methods: (1) transcript analysis on gene of interest was carried out to confirm the knockdown of specific gene, for example, LSD1 knockdown by LSD1 directed siRNA using LSD1 oligonucleotide (described in Table 3) for real-time PCR from TaqMan. (2) at the ChIP level (please refer to ChIP results for specific genes) (3) optimization experiments were carried out for each siRNA to confirm maximal transfection efficiency (70-80%) in MCF-7. Therefore, the results presented herein are reproducible. Each mock (control) and gene specific siRNA knockdown experiment was performed three independent times and only one representative experiment is shown in this section.

Molecular Biology Techniques

For RNA isolation procedure, all the pipettes, tube holders and gloves were always pre-treated with RNase Zap (Ambion, VIC, Australia). RNAse, DNAse, pyrogen free, sterile microtubes (Axygen Scientific, Inc., Union City) and Pre-sterile aerosol resistant tips and fresh bench coat were routinely used for all the molecular biology work described in this section.

Total RNA Isolation

For most of the experiments, total RNA was extracted from $5 \times 10^5$ to $1 \times 10^6$ MCF-7 cells unless otherwise specified. Cells were first thawed in 1 mL of Trizol® Reagent (Invitrogen, Carlsbad, Calif.) for 5 minutes at room temperature to inactivate RNases, followed by trituration to dislodge the cell pellet. The dissociated cells suspended in Tizol (1 mL) were transferred into a 1.5 mL Eppendorf tube for 5 minutes for homogenization. RNA was then extracted by addition of 200 μL chloroform and mixing was done vigorously before centrifuging the samples at 8,000×g for 30 minutes at 4° C. The aqueous layer was then collected into a fresh 1.5 mL Eppendorf tube and an equal volume of isopropanolol was added to the aqueous layer and mixed gently. After 5 minutes at room temperature, samples were either snap frozen on dry ice and stored at −70° C. overnight or until the isolation procedure could be re-commenced. After thawing the samples quickly, the samples were again centrifuged at 8,000×g for 30 minutes at 4° C. to precipitate the RNA. To remove all traces of isopropanolol, next the RNA pellets were washed with 1 mL of ice cold 80% ethanol (Analytical UNIVAR, Seattle, Wash.) before centrifuging at 3,600×g for 10 minutes at 4° C. All ethanol then was removed and pellets were allowed to air dry for 5 minutes. RNA samples were then solubilized by re-suspending them in 50 μL of nuclease-free DEPC (Diethylpyrocarbonate treated) water (Ambion, VIC, Australia). Next, 2 μL of the sample was taken out to measure RNA quality and quantity on Nano-Drop® Spectrophotometer ND 1000 (Nanodrop Technologies, Inc., Wilmington, Del., USA) using ND-1000 V3.30 software. All the RNA samples were found pure as they had $A_{260}/A_{280}$ ratio of 1.9-2.1 and this ratio provides an estimate of RNA purity with respect to contaminants such as proteins that absorb in the UV spectrum.

First Stand cDNA Synthesis

Superscript™® III kit (Invitrogen, Carlsbad, Calif.) was used for cDNA synthesis. Master mix-1 was prepared by adding 1 μL of 5 μM oligo (dT) and 1 μL of 100 mM dNTPs and mixed by flicking. Mastermix-2 was prepared by adding 2 μL of RT buffer, 2 μL of 3 mM mgCl$_2$, 2 μL of DTT mix, 1 μL of RNAse out, 1 μL of superscript III and mixed by flicking. For 1 μg RNA, 2 μL of the master mix-1 was added to the samples, mixed and incubated at 65° C. for 5 minutes and then samples were placed on ice to stop the reaction. This step was followed by addition of 10 μL of the master mix-2 per sample and incubation of samples at 50° C. for 50 minutes. The reaction was then stopped by incubating samples at 85° C. for 5 minutes followed by placing the samples on the ice for 2 minutes. Finally 1 μL of RNaseH was added to each sample and samples were incubated at 37° C. for 20 minutes. All the samples were either snap frozen on dry ice or used immediately for quantitative Real-Time PCR analysis.

Quantitative Real-Time PCR (qRT-PCR) Analysis

TaqMan® Gene expression Assays (Applied Biosystems, Foster City, Calif.) were used to perform qRT-PCR on an ABI PRISM 7900 HT fast Real-Time PCR sequence detector (PerkinElmer/PE, Applied Biosystems, Foster City, Calif.) using the FAM probe channel. A total reaction volume of 10 μL was used with cDNA diluted at 1:20 with DEPC water for the PCR, as detailed in the manufacture's guidelines (PerkinElmer/PE, Applied Biosystems, protocol PN 4333458). For all genomic DNA, Power SYBR Green real-time PCR (PerkinElmer/PE, Applied Biosystems, Foster City, Calif.) reactions were performed and the ChIP samples were diluted at 1:5. Each PCR was performed in duplicate wells using thermocycler conditions as follows: stage 1-50° C. for 2 minutes for 1 cycle; stage 2-95° C. for 10 minutes for 1 cycle; stage 3-95° C. for 15 seconds and 60° C. for 1 minute for 40 cycles. For all the primers sets, no template controls were always included to test for PCR amplification of any contaminating DNA within the PCR mix. Dissociation curves were performed for each primer set to confirm amplification of a single product using the following PCR conditions: stage 1-95° C. for 15 seconds; stage 2-60° C. for 20 seconds; with a minimum ramp speed to reach stage 3-95° C. for 15 seconds. PCR reactions were performed using Optical PCR 384 well reaction plates (Applied Biosystems, Foster City, Calif.).

Data Analysis of cDNA Experiments

All the threshold cycle ($C_t$) values from the PCR amplification plots were converted to arbitrary copy number using the formula $100000/2^{(C_t-17)}$ in Microsoft excel spread sheet, where a $C_t$ value of 17 was set to $10^5$ copies and assuming that each cycle increase equated to a 2 fold increase in input DNA. All the primers were checked against an amplicon standard curve to show that above formula produced results that were similar to results obtained with amplification standard curve method. Cyclophilin A primer (section 0) PCR reactions were performed concurrently for each experiment to normalize for differences in RNA input and cDNA synthesis. All experiments were performed in duplicate.

cDNA Synthesis for MicroRNA

The TaqMan® MicroRNA Reverse Transcription Kit (Applied Biosystems, Foster City, Calif.) was used to convert total RNA into cDNA for microRNA analysis with specific TaqMan® miRNA primers assays. Reagents of TaqMan® MicroRNA Reverse Transcription Kit were allowed thawing completely on ice before preparing RT master mix by adding following components per 15 μL reaction volume; 0.15 μL dNTP mix (100 mM), 1 μL Multiscribe™ RT enzyme (50 U/μL), 1.5 μL 10×RT Buffer, 0.19 μL RNase Inhibitor (20 U/μL) and 4.16 μL Nuclease free water to get a total volume of 7 μL. All the components were mixed gently, centrifuged briefly and then this RT master mix was placed on ice until the RT reaction plate was prepared. RT reaction plate was then prepared; by first combining total RNA (1-10 ng per 15 μL reaction) with the RT master mix in a ratio of 5 μL RNA:7 μL RT master mix. MicroRNA RT primers were then thawed on ice and tubes to be used for RT reaction were labeled with appropriate numbers. Next, 12 μL of the RT master mix containing total RNA was dispensed into each tube before adding 3 μL of 5×RT primers to the appropriate tubes to bring the total volume 15 μL per tube. All the tubes were then mixed gently, centrifuged briefly and incubated on ice for 5 minutes or until ready to load on thermal cycler for reverse transcription at following thermal cycles at 15 μL reaction volume—Hold for 16° C. for 30 minutes for 1 cycle; Hold for 42° C. for 30 minutes for cycle 2; Hold for 85° C. for 5 minutes for cycle 3 and 4° C. for ∞ for cycle 4. After completion of the run, samples were either saved at −20° C. or used immediately for qPCR.

qPCR Amplification for MicroRNA cDNA qPCR reaction was performed by preparing the 20 μL qPCR reaction mix by addition of following components into appropriate tubes: 1 μL of TaqMan® small RNA Assay (20×); 1.33 μL of product from RT reaction; 10 μL of TaqMan® Universal PCR master Mix II (2×, no UNG) and 7.67 μL nuclease free water. Components were then mixed gently and centrifuged briefly. All the qPCR reactions were performed in triplicate. 20 μL of the complete qPCR reaction mix (including assay and RT product) were then transferred into each of three wells of a 384-well plate. Plate was then sealed, centrifuged briefly and PCR amplification was performed as described in section 2.5.2.

Chromatin Assays

Chromatin Immunoprecipitation (ChIP) Assay

Between 1-5×10$^6$ Cells were harvested following various treatments according to the experimental requirement and re-suspended in 10 mL DMEM completer media at room temperature after counting then at Vi-CELL counter. Cells were then cross linked with freshly prepared 1% paraformaldehyde (PFA) (Analytical UNIVAR, Seattle, Wash.) for 10 minutes at room temperature with continuous but slow rotations on rotary wheel. Next, the reaction was quenched by the addition of 2M glycine solution (AnalaR, Merck, Darmstadt, Germany) to a get a final concentration of 125 mM and mixed further for 10 minutes at room temperature on the rotary wheel. Cells were then washed three times with 10 mL ice cold PBS and the cell pellet was either snap frozen on dry ice or used immediately afterwards. SDS Lysis Buffer (Upstate Biotechnology, Billerica, Mass.) was prepared by addition of 1× complete protease inhibitor solution (1 tablet dissolved in 1 mL DEPC water) (Roche Diagnostics, Mannheim, Germany) and cell pellet was then re-suspended in 250 μL of the in the SDS lysis buffer for 10 minutes at room temperature. Cells were sonicated (10 sec pulses for 2 minutes on 1 liter ice cold water mixed with ice, 70% maximum output) to shear the chromatin to obtain an average DNA fragment size of 250-500 bp using a Cole Palmer Ultrasonic processor (Cole Plamer, Vernon Hills, Ill.). After the sonication, samples were centrifuged at 10,2000×g for 5 minutes at room temperature to clear cellular debris and the supernatant was then diluted to 1:10 with ChIP dilution buffer (Upstate Biotechnology, Billerica, Mass.). Antibodies as per the experiment requirement were aliquoted to the 1.5 mL Eppendorf tubes before adding sonicated chromatin from 0.5-1×10⁶ cells diluted in the dilution buffer and the ChIP mixture was then incubated with antibodies overnight at 4° C. on rotary wheel. For all the experiments total genomic DNA without any antibody (named Total Inputs) for each condition was snap frozen and stored at −70° C., also a sample without any antibody (named No antibody) was processed in parallel with the ChIP samples. Next, immune complexes were bound by addition of 60 μL of salmon sperm DNA/Protein A agarose beads at 4° C. for 1 hour at rotary wheel. Samples were then centrifuged at 2500×g for 2 minutes at 4° C. and the supernatant was discarded before washing beads at 4° C. for 5 minutes on a rotary wheel with each of the following washing buffers from Upstate Biotechnology (Billerica, Mass.) in the same order as described; first wash—500 μL of low salt immune complex wash buffer; second wash— 500 μL of high salt immune complex wash buffer; third wash-500 μL of LiCi immune complex wash buffer; fourth wash-500 μL of low salt immune complex wash buffer and fourth wash—1 mL TE buffer (10 mM Tris-HCl pH 8.0, 1 mM EDTA). Protease Inhibitor-complete, 1× (Roche Diagnostics, Mannheim, Germany) was added to all the wash buffers immediately before use. DNA-protein complexes were then eluted from the beads with 400 μL of the freshly made elution buffer (1% (w/v) SDS, 100 mM NaHCo₃) for 30 minutes at room temperature on rotary wheel. Samples and total input controls were then incubated to hydrolyze cross links (or reverse-cross link) at 66° C. overnight after adding 16 μL of 5M sodium Chloride (Sigma-Aldrich, St. Louis, Mo.). Next day, samples were treated with 1 μL of Protease K solution (20 μg/μL) (Invitrogen, Carlsbad, Calif.) for 1 hour at 45° C. Digested protein was removed from the ChIP samples by addition of equal volume of phenol-chloroform-isoamyl alcohol (25:24:1) saturated with 10 mM Tris, pH 8.0, 1 mM EDTA (Sigma-Aldrich, St. Louis, Mo.), mixing the samples and subsequent centrifugation at 10,200×g for 20 minutes at room temperature for collection of the aqueous layer. Genomic DNA was precipitated from aqueous fraction by the addition of 2.5 volumes of ice-cold absolute ethanol (Analytical UNIVAR, Seattle, Wash.), 0.1 volume of 3 M sodium acetate buffer solution pH 5.2 (Sigma-Aldrich, St. Louis, Mo.) and 25 μg of GeneElute™ linear polyacrylamide (Sigma-Aldrich, St. Louis, Mo.) for at least 24 hours at −20° C. Next, samples were pelleted by centrifugation and washing with 80% ice cold ethanol and pellets were allowed to air dry prior to suspension in 20 μL of the DEPC water for real time PCR analysis. The oligonucleotides used for performing real-time PCR on ChIP samples have been listed in Table 4.

Sequential ChIP

Primary ChIP of was performed as described above until the TE buffer washing step. Thus, immunoprecipitates from the primary ChIP were dissolved in 60 μL elution buffer containing 10 mM DTT (Superscript™ III RNaseH-Reverse Transcriptase kit (Invitrogen, Carlsbad, Calif.) in DEPC water and incubated for 1 hour in a 37° C. water bath. Tubes were flicked every 15 minutes during this incubation period. Next, samples were diluted with 1:40 of ChIP dilution buffer before taking 400 μL of the samples to be frozen at −70° C. to use as a total genomic input for secondary ChIP. The second antibody was added to these samples and immunoprecipitation was carried out again as the ChIP protocol (as defined above.) except that immune complexes were bound to 60 μL of the salmon sperm DNA/Protein A agarose beads for 2 hour at 4° C. Sequential ChIP samples were then eluted, the cross-linking was reversed and the genomic DNA was precipitated as method described in above. Sequential ChIP analysis was carried out using the ChIP enrichment ratio method described below and then expressed as a fold change with respect to the non-stimulated samples.

Data Analysis for ChIP Experiments

All ChIP assays were carried out in the presence of a non-antibody control as well as an isotype specific control antibody. The negative control is a non-antibody control and the enrichment values from these are routinely low and are included as background subtractions in the calculations of ChIP enrichment ratio. $C_t$ values from the real time PCR amplification plots were first converted to arbitrary copy number using formula the $100000/2^{(C_t-17)}$. Sample data were normalized to the corresponding total input arbitrary copy number. Fold change above the no antibody control was then calculated to get ChIP enrichment ratio. ChIP enrichment ratio values were multiplied by a factor of 10 except the ChIP enrichment ratio values for histone modifications. This method of analysis was adopted from Pokholok et al. (2006. *Science* 313: 533-536) who established that the ChIP enrichment ratio presented on the linear scale better emphasizes signal versus noise in the display of ChIP-on-ChIP data over a logarithmic scale (Pokholok et al., supra). Consequently, all the ChIP data in this thesis is presented on a linear scale. All chip assays represent mean±standard error (SE) of three independent experiments and analyzed in duplicate by real-time PCR. In some cases fold change was calculated with respect to the non-stimulated sample, which was set as 1. Statistical significance was determined by two-tailed Paired-t test using GraphPad Prism 5.03 for Windows.

All the chip samples were always normalized with the Total input (TI) of each corresponding sample. If the recovery of the ChIP samples was low in the stimulated cells and CSC subset, then the arbitrary copies achieved in the real-time PCR analysis would be low but this was not the case and arbitrary copies from the samples were in same Ct range as the others. Since the "ChIP enrichment ratio" method has been used for analysis, of the recoveries of the ChIP DNA across the different samples did not affect the analysis and interpretation of the data. This ChIP analysis method by using "ChIP enrichment ratio" is considered as the best method for calculating ChIP data (Pokholok et al., supra). Therefore, the results were not likely to be effected due to poor ChIP recoveries.

For sequential ChIP analysis, the genomic DNA recovered from the sequential ChIP experiments was quantified by SYBR Green real-time PCR using primers specific for the promoter regions of the uPAR or miR 200c. The $C_t$ values from the PCR amplification plots were converted to arbitrary copy number using the formula $100000/2^{(C_t-17)}$. The no antibody control was subtracted from the data for each sample, which were then normalized to the corresponding total input (TI-1) that was taken prior to the first immunoprecipitation. Data generated were then normalized to their respective $2^{nd}$ total immunoprecipitation input (TI-2). Finally, fold change was then calculated with respect to the non-stimulated sample, which was set as 1. These values were then used to prepare the sequential ChIP plots shown in Figures. This method of sequential ChIP analysis has been adopted from Sutcliffe et al., 2009. Statistical significance was determined by two-tailed Paired-t test using GraphPad Prism 5.03 for Windows. This method of sequential ChIP analysis has been adopted from Sutcliffe et al., 2009.

In Vivo Murine Xenograft Model

To monitor the effect of LSD1 inhibitors in vivo on tumor recurrence, in vivo murine xenograft model of breast cancer recurrence was used. The MDA-MB 231 cell line model, which is one of the most robust and well-established models was used in 6 weeks old BALB/c female nude mice. $5\times10^6$ MDA MB 231 cells were injected in the mammary fat pad of each mouse. Mice were observed for the tumor appearance and growth. Once the tumors reach 50 mm$^3$ volume size (determined by caliper measurement), treatments were initiated. Mice were monitored until tumors reach 500 mm$^3$ and sacrificed for collection of tumors. Each treatment group consisted 14 mice each (5 mice for tumor growth curve+3 mice each for tumor collection at 3 time points-treatment start day-week 0, chemotherapy tumor reduction-approx. week 4 and until tumor reach 500 mm$^3$ approx. week 7). Tumor volumes were measured every week and three mice from each group were sacrificed for IHC, FACS, and RNA extraction at above mentioned three time points.

Generation of Tumors

1. Cells were thawed from lot labeled MDA-MB-231 (Sep. 2, 2014).
2. Cells were expanded to 54×150 cm$^2$ flasks.
3. Cell suspension was then spun down at 1500 rpm for 5 min. at room temperature.
4. Supernatant were then discarded and cell pellet resuspended in 2.5 mL of cold PBS and 2.5 mL cold Matrigel™ (NOTE: Matrigel is in liquid state only when kept on ice).
5. Mice were then injected with 50 μL of the Matrigel™+ $5\times10^6$ cell suspension in PBS using 26" needles and isoflurane as an anesthetic. Each 50 μL of the mixture contains $2\times10^6$ MDA-MB-231 cells.
6. Mice were monitored and weighed and monitored daily till 15 May 2014.
7. Measurements for tumor volume began at day 7 post injection of MDA-MB-231. Then the tumor volumes were measured daily till 15 May 2014.

Treatment of mice started at day 16 post injection of MDA-MB-231, where tumors roughly reached a volume of 50 mm$^3$.

Treatment of Mice

Group A: Control—20 μl of DMSO
Group B: 4 mg/kg of docetaxel (11 mice)
Group C: 100 mg/kg of pargyline (11 mice)
Group D: 4 mg/kg of docetaxel+100 mg/kg of pargyline (11 mice)

Collection of Samples

Tumor, spleen, liver, lungs and kidneys were collected into (1) fixative agent for IHC and (2) 2 different RNase free 1.5 ml Eppendorf tubes to be frozen down in the −80 freezer at Day 0 (1 mouse/group A-C).

At week four post treatment, tumor samples were collected (3 mice/group; taking the largest, smallest and average sized tumor) for flow cytometry with CD44, CD24 and Hoechst staining. 1 ml from each single cell suspension from each sample was spun down and the cell pellets collected for RNA.

At week 7 post treatment, the remaining tumor samples were collected for flow cytometry with CD44, CD24 and Hoechst staining. Remaining sample was used for RNA extraction.

Single Cell Suspension and Flow Cytometry Staining

1. Tumors were collected in 5 mL of DMEM supplemented with 2.5% FCS in 15 mL tubes.
2. Tumors were then weighed individually to determine the amount of collagenase to add. NOTE: use 1 mg of collagenase/1 g of tumor, concentration of collagenase=100 mg/mL in DMEM.
3. Tumors were chopped up finely using surgical blades in a petri dish and then transferred back into 15 mL tube with appropriate amount of media e.g. if tumor was 1 g, then the media is topped up to 10 mL and 100 μL of collagenase stock is added.
4. Samples were then incubated at 37° C. for 1 hour with shaking/tipping of tubes every 5 min.
5. After 1 hour, samples were then spun down at 500×g for 5 min. at room temperature.
6. Cells were then resuspended in 10 mL of 2.5% FCS+ DMEM and filtered using a 0.2 □m filter into a 50 mL tube.
7. Cells were then counted using trypan blue staining.
8. A total number of $2\times10^5$ cells were stained for CD44-APC, CD24-PE and Hoechst.

Staining was done with 100 mL of CD44-APC (1:50), CD24 (1:50) and Hoechst (1:1000), in the dark in 1.5 ml Eppendorf tubes with rotation for 35 min. at 4° C.

Cells were then washed with 1 mL of FACS buffer (1% FCS+PBS) and resuspended in 100 μL into small FACS tubes for acquisition.

Flow cytometry was done using LSR II at JCSMR, ANU.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for inhibiting proliferation, survival or viability of a cancer stem cell (CSC) in a human subject, the method comprising contacting the CSC with a proliferation-, survival- or viability-inhibiting amount of a lysine specific demethylase-1 (LSD1) inhibitor, wherein the CSC has been determined to be CD44$^{high}$, CD24$^{low}$, and to express Sox2 mRNA or SOX2 polypeptide at a level that is less than ⅕ of the level of Sox2 mRNA or SOX2 polypeptide of a pluripotent stem cell.

2. A method according to claim 1, wherein the CSC has been determined to express the pluripotent stem cell marker Oct4 at a level that is less than ⅕ of the level of Oct4 on a pluripotent stem cell.

3. A method according to claim 1, wherein the CSC has been determined to express one or more CSC markers selected from ABCB5, ALDH1, ABCG2, α6 integrin, α2 β1 integrin, β-catenin activity, CD15, CD13, CD20, CD24, CD26, CD29, CD44, CD90, CD133, CD166, CD271, c-Met, Hedgehog, Gli, Nestin, CXCR4, LGR5, Trop2, Nodal and Activin.

4. A method according to claim 1, wherein the CSC is a breast CSC.

5. A method according to claim 1, wherein the CSC is a hormone receptor negative CSC.

6. A method according to claim 1, wherein the LSD1 inhibitor is a selective LSD1 inhibitor.

7. A method according to claim 1, wherein the LSD1 inhibitor is a Pan-LSD inhibitor.

8. A method according to claim 1, further comprising detecting overexpression of a LSD1 gene in the CSC prior to contacting the CSC with the LSD1 inhibitor, wherein the overexpression is relative to the expression of the LSD gene in a non-CSC tumor cell.

9. A method for treating a cancer in a human subject, wherein the cancer comprises cancer stem cells (CSCs) that have been determined to be $CD44^{high}$, $CD24^{low}$ and to express Sox2 mRNA or Sox2 polypeptide at a level that is less than ⅕ of the level of Sox2 mRNA or Sox2 polypeptide of a pluripotent stem cell and non-CSC tumor cells, the method comprising administering to the subject an LSD1 inhibitor in an effective amount to inhibit the proliferation, survival or viability of the CSCs, thereby treating the cancer in the subject.

10. A method according to claim 9, further comprising identifying that the subject has or is at risk of developing a cancer comprising CSCs and non-CSC tumor cells prior to the administration of the LSD1 inhibitor.

11. A method according to claim 9, wherein the cancer is breast cancer.

12. A method according to claim 9, wherein the CSCs are capable of giving rise to non-CSC tumor cells that are hormone-resistant.

13. A method according to claim 12, wherein the non-CSC tumor cells are hormone receptor negative for at least one hormone receptor selected from an estrogen receptor (ER) and a progesterone receptor (PR).

14. A method according to claim 9, further comprising detecting overexpression of an LSD1 gene in a tumor sample obtained from the subject, wherein the overexpression is relative to the expression of the LSD gene in a non-CSC tumor cell, and wherein the tumor sample comprises CSCs that have been determined to be $CD44^{high}$ $CD24^{low}$ and to express Sox2 mRNA or Sox2 polypeptide at a level that is less than ⅕ of the level of Sox2 mRNA or Sox2 polypeptide of a pluripotent stem cell prior to administering the LSD inhibitor to the subject.

15. A method for treating or preventing a cancer in a human subject, wherein the cancer comprises cancer stem cells (CSCs) that have been determined to be $CD44^{high}$, $CD24^{low}$ and to express Sox2 mRNA or Sox2 polypeptide at a level that is less than ⅕ of the level of Sox2 mRNA or Sox2 polypeptide of a pluripotent stem cell and non-CSC tumor cells, the method comprising concurrently administering to the subject a LSD inhibitor in an effective amount to inhibit the proliferation, survival or viability of the CSCs of the cancer and a cancer therapy or agent that inhibits the proliferation, survival or viability of the non-CSC tumor cells, to thereby treat or prevent the cancer.

16. A method according to claim 15, wherein the cancer therapy or agent is selected from radiotherapy, surgery, chemotherapy, hormone ablation therapy, pro-apoptosis therapy and immunotherapy.

17. A method according to claim 15, wherein the cancer therapy or agent targets rapidly dividing cells or disrupts the cell cycle or cell division.

* * * * *